US010561405B2

(12) United States Patent
Pizer et al.

(10) Patent No.: US 10,561,405 B2
(45) Date of Patent: Feb. 18, 2020

(54) METHOD FOR MANUFACTURING A BIOLOGICAL FLUID SENSOR

(71) Applicant: CoreSyte, Inc., Great Falls, VA (US)

(72) Inventors: Adam Pizer, Jeffersonville, IN (US); Dalton Pont, Sterling, VA (US); John V. Chiochetti, Annapolis, MD (US)

(73) Assignee: CORESYTE, INC., Great Falls, VA (US)

( * ) Notice: Subject to any disclaimer, the term of this patent is extended or adjusted under 35 U.S.C. 154(b) by 201 days.

(21) Appl. No.: 15/487,046

(22) Filed: Apr. 13, 2017

(65) Prior Publication Data

US 2017/0223844 A1 Aug. 3, 2017

Related U.S. Application Data

(63) Continuation-in-part of application No. 15/177,703, filed on Jun. 9, 2016, now Pat. No. 9,622,725, which
(Continued)

(51) Int. Cl.
*A61B 10/00* (2006.01)
*B23K 1/00* (2006.01)
(Continued)

(52) U.S. Cl.
CPC ........ *A61B 10/0064* (2013.01); *A61B 5/1477* (2013.01); *A61B 5/14517* (2013.01);
(Continued)

(58) Field of Classification Search
CPC .... H05K 3/3494; H05K 3/341; H05K 3/3468; B23K 26/384; B23K 26/389; B23K 1/08;
(Continued)

(56) References Cited

U.S. PATENT DOCUMENTS 5,310,469 A * 5/1994 Cunningham ......... C12Q 1/001
204/403.09
5,718,816 A * 2/1998 Savage .............. G01N 33/4915
204/400
(Continued)

FOREIGN PATENT DOCUMENTS

WO 1987000286 A1 1/1987
WO 2010045247 A1 4/2010
(Continued)

OTHER PUBLICATIONS

Rose et al., "Adhesive RFID Sensor Patch for Monitoring of Sweat Electrolytes", 2013, IEEE. (Provided by Applicant).*
(Continued)

*Primary Examiner* — Peter Dungba Vo
*Assistant Examiner* — Jeffrey T Carley
(74) *Attorney, Agent, or Firm* — NEO IP

(57) ABSTRACT

The present invention presents a method of fabrication for a physiological sensor with electronic, electrochemical, and chemical components. The fabrication method comprises steps for manufacturing an apparatus comprising at least one electrochemical sensor, a microcontroller, and a transceiver. The fabrication process includes the steps of substrate fabrication, circuit fabrication, pick and place, reflow soldering, electrode fabrication, membrane fabrication, sealing and curing, layer bonding, and dressing. The physiological sensor is operable to analyze biological fluids such as sweat.

19 Claims, 66 Drawing Sheets

Related U.S. Application Data is a continuation of application No. 15/019,006, filed on Feb. 9, 2016, now Pat. No. 9,645,133.

(60) Provisional application No. 62/130,047, filed on Mar. 9, 2015.

(51) Int. Cl.

| | | |
|---|---|---|
| B29C 69/00 | (2006.01) | |
| A61B 5/145 | (2006.01) | |
| A61B 5/1477 | (2006.01) | |
| A61B 5/00 | (2006.01) | |
| B23K 26/402 | (2014.01) | |
| B23K 26/384 | (2014.01) | |
| G01N 33/487 | (2006.01) | |
| B23K 1/008 | (2006.01) | |
| B23K 26/382 | (2014.01) | |
| B23K 26/38 | (2014.01) | |
| B29K 27/06 | (2006.01) | |
| B29L 31/00 | (2006.01) | |
| B29L 31/34 | (2006.01) | |
| B29L 9/00 | (2006.01) | |
| H05K 1/16 | (2006.01) | |
| B23K 101/42 | (2006.01) | |
| B23K 101/36 | (2006.01) | |
| B23K 103/00 | (2006.01) | |
| B23K 103/16 | (2006.01) | |

(52) U.S. Cl.
CPC .......... *A61B 5/4266* (2013.01); *A61B 5/6833* (2013.01); *B23K 1/008* (2013.01); *B23K 1/0016* (2013.01); *B23K 26/38* (2013.01); *B23K 26/384* (2015.10); *B23K 26/389* (2015.10); *B23K 26/402* (2013.01); *B29C 69/00* (2013.01); *G01N 33/48707* (2013.01); *A61B 2562/0295* (2013.01); *A61B 2562/12* (2013.01); *A61B 2562/125* (2013.01); *A61B 2562/164* (2013.01); *A61B 2562/166* (2013.01); *B23K 2101/36* (2018.08); *B23K 2101/42* (2018.08); *B23K 2103/172* (2018.08); *B23K 2103/42* (2018.08); *B29K 2027/06* (2013.01); *B29K 2995/0005* (2013.01); *B29L 2009/008* (2013.01); *B29L 2031/34* (2013.01); *B29L 2031/753* (2013.01); *H05K 1/16* (2013.01); *H05K 2201/10151* (2013.01)

(58) Field of Classification Search
CPC ...... B23K 2201/42; H01L 2021/60007; H01L 23/488; A61B 10/0064; A61B 5/14517; G01N 27/327
See application file for complete search history.

(56) References Cited

U.S. PATENT DOCUMENTS

| | | | |
|---|---|---|---|
| 6,198,953 B1* | 3/2001 | Webster | A61N 1/30 600/345 |
| 7,383,072 B2* | 6/2008 | Edmonson | A61B 5/14521 600/345 |
| 7,575,549 B2 | 8/2009 | Miller | |
| 8,388,534 B2 | 3/2013 | Jang et al. | |
| 2003/0163287 A1 | 8/2003 | Vock et al. | |
| 2006/0253011 A1 | 11/2006 | Edmonson et al. | |
| 2007/0096604 A1 | 5/2007 | Edmonson et al. | |
| 2007/0179371 A1* | 8/2007 | Peyser | A61B 5/14521 600/347 |
| 2008/0039700 A1 | 2/2008 | Drinan et al. | |
| 2009/0159442 A1* | 6/2009 | Collier | C12Q 1/00 204/403.1 |
| 2010/0176006 A1 | 7/2010 | Bickford et al. | |
| 2013/0245388 A1 | 9/2013 | Rafferty et al. | |
| 2014/0330096 A1 | 11/2014 | Brunswick | |
| 2014/0350432 A1 | 11/2014 | Khalfallah et al. | |
| 2015/0019135 A1 | 1/2015 | Kacyvenski et al. | |
| 2015/0057515 A1* | 2/2015 | Hagen | A61B 5/14546 600/346 |
| 2015/0112164 A1 | 4/2015 | Heikenfeld et al. | |
| 2015/0112165 A1 | 4/2015 | Heikenfeld | |
| 2016/0262666 A1* | 9/2016 | Nyberg | A61B 5/1477 |
| 2016/0262667 A1* | 9/2016 | Pizer | A61B 5/1477 |
| 2016/0290952 A1* | 10/2016 | Pizer | H05K 3/10 |

FOREIGN PATENT DOCUMENTS

| | | |
|---|---|---|
| WO | 2013152087 A2 | 10/2013 |
| WO | 2014197822 A2 | 12/2014 |
| WO | 2015058055 A1 | 4/2015 |
| WO | 2015058064 A1 | 4/2015 |
| WO | 2015184072 A1 | 12/2015 |
| WO | 2015184084 A2 | 12/2015 |
| WO | 2015184097 A2 | 12/2015 |
| WO | 2016007944 A2 | 1/2016 |
| WO | 2016049019 A1 | 3/2016 |
| WO | 2016061362 A2 | 4/2016 |
| WO | 2016130905 A1 | 8/2016 |
| WO | 2016134235 A1 | 8/2016 |
| WO | 2016138087 A1 | 9/2016 |

OTHER PUBLICATIONS

Daniel P. Rose, M. Ratterman, Daniel K. Griffin, Linlin Hou, Nancy Kelley-Loughnane, Rajesh R. Naik, Joshua A. Hagen, I. Papautsky, Jason Heikenfeld, Adhesive RFID Sensor Patch for Monitoring of Sweat Electrolytes, IEEE Transactions on Biomedical Engineering, Paper ID # TBME-00773-2014-R1, Manuscript revised Sep. 10, 2014; accepted Nov. 6, 2014.

Jason C. Heikenfeld, Advanced Adhesives for Chronological Sweat Sensors, U.S. Appl. No. 62/074,295, filed Nov. 3, 2014; Specification including the claims, abstract, and drawings.

Jason C. Heikenfeld, Advanced Sweat Sensor Adhesion, Hermetic, and Fluidic Strategies, U.S. Appl. No. 62/023,233, filed Jul. 11, 2014; Specification including the claims, abstract, drawings, and Appendix to the Specification.

Jason C. Heikenfeld, Device Construction for Prolonged and Reliable Sweat Stimulation and Sensing, U.S. Appl. No. 62/003,707, filed May 28, 2014; Specification including the claims, abstract, drawings, and Appendix to the Specification.

Jason C. Heikenfeld, Sweat Sensor With Chronological Assurance, U.S. Appl. No. 62/003,675, filed May 28, 2014; Specification including the claims, abstract, drawings, and Appendix to the Specification.

Jason C. Heikenfeld, Sweat Stimulation for Integrated or Repeated Biosensing, U.S. Appl. No. 61/892,859, filed Oct. 18, 2013; Specification including the claims, abstract, and drawings.

Jason Heikenfeld, "Let Them See You Sweat", IEEE Spectrum, Nov. 2014, p. 46.

Joshua Andrew Hagen, Sweat Simulation, Collection, and Sensing Systems, U.S. Appl. No. 61/620,069, filed Apr. 4, 2012; Specification including the claims, abstract, drawings, and Appendix to the Specification.

Liu, et al. "Implementation of a microfluidic conductivity sensor—A potential sweat electrolyte sensing system for dehydration detection," in Conf Proc IEEE Eng Med Biol Soc, 2014:1678-81, 5 pgs.

Schwartz, Irving L and Jorn Hess Thaysen, Excretion of Sodium and Potassium in Human Sweat, The Rockefeller Institute for Medical Research, New York, NY, published Sep. 28, 1955, pp. 114-120.

Sonner, Z., E. Wilder, J. Heikenfeld, G. Kasting, F. Beyette, D. Swaile, F. Sherman, J. Joyce, J. Hagen, N. Kelley-Loughnane, and R. Naik, The microfluidics of the eccrine sweat gland, including biomarker partitioning, transport, and biosensing implications, Biomicrofluidics 9, 031301, accepted Apr. 30, 2015, published online May 15, 2015, pp. 031301-01-031301-019 (19 pages).

(56) References Cited

OTHER PUBLICATIONS

Fowkes, "Sweat Rates and Fluid Turnover in Professional Football Players: A Comparison of National Football League Linemenand Backs," Journal of Athletic Training 2008;43(2):184-189.
Sawka et al., "Exercise and Fluid Replacement," American College of Sports Medicine (AGSM) (1996) Position Stand Med SciSports Exerc 28: i-vii.

\* cited by examiner

| ITEM NO. | PART NUMBER | DESCRIPTION | QTY. |
|---|---|---|---|
| 1 | 3M 9917 | Double Sided Adhesive | 1 |
| 2 | 3M 9926T | Woven Top Adhesive | 1 |
| 3 | Key Electronics PCB | Polyimide Flex PCB | 1 |
| 4 | GE Whatman 1001 | Grade 1 Filter Paper | 1 |

Basic Ratio for Sweat Flow Rate (SFR)

| K (mV : mM) | Na (mV : mM) | Ratio (Na/K) | SFR (uL/min/cm$^2$) |
|---|---|---|---|
| 25 : 5 | 100 : 20 | 4 | 0.0 |
| 25 : 5 | 150 : 30 | 6 | 0.5 |
| 25 : 5 | 250 : 50 | 10 | 1.0 |
| 25 : 5 | 400 : 80 | 16 | 1.5 |
| 25 : 5 | 450 : 90 | 18 | 2.0 |
| 25 : 5 | 500 : 100 | 20 | 2.5 |
| 25 : 5 | 550 : 110 | 22 | 3.0 |

Body Surface Area (BSA) Calcs

DuBois and DuBois[1]   BSA (m$^2$) = 0.007184 × Height (cm)^0.725 × Weight (kg)^0.425

Gehan and George[2]   BSA (m$^2$) = 0.0235 × Height (cm)^0.42246 × Weight (kg)^0.51456

Haycock[3]   BSA (m$^2$) = 0.024265 × Height (cm)^0.3964 × Weight (kg)^0.5378

Mosteller[4] (CoreSyte Uses)   $$BSA\ (m^2) = \sqrt{\frac{Height\ (cm) \times Weight\ (kg)}{3600}}$$

Sweat Loss & Body Mass Loss Calcs

| | | | |
|---|---|---|---|
| Sweat Loss 1 | SFR 1 × (Use Ratio) | BSA × (Use Calc) (User Ht Wt Inputs) | Dur (From Session Time) |
| Sweat Loss 2 | SFR2 × (KSI table, User Wt Input, Phone Temp) (Sweat Stds Table) | | Dur (Sess Time) |
| Sweat Mass | Convert SL1 Vol (L) to Mass (kg) | | |
| % Body Mass Loss | Sweat Mass/User Wt | | |
| Sweat Loss Ratio (SLR) | SL1/SL2 (Sweat More/Less Than Norm) | | |

FIG. 11A

| Work Level | Level 1 | | Level 2 | | Level 3 | |
|---|---|---|---|---|---|---|
| Zone | Zone 1 | Zone 2 | Zone 3 | Zone 4 | Zone 5 | Zone 6 |
| SFR | 0.5 | 1.0 | 1.5 | 2.0 | 2.5 | 3.0 |
| mV Ratio | 0-6 | 7-10 | 11-16 | 17-18 | 18-20 | 21+ |
| Na Loss | 40 | 50 | 70 | 80 | | |
| K Loss | 4 | 5 | 7 | 8 | | |
| Typ Wt | Under 120 | 120-220 | 220-260 | 260+ (SFR Affected by HR & Temp) | | |
| Elite | NCAA Players (Source NIH/NCBI) NFL Players (Source NIH/NCBI) NHL Players (Source NIH/NCBI) NBA Players | | | | | |

UT & GSSI Publication

| Sweating Rate and Sweat Sodium Concentration | | | |
|---|---|---|---|
| Variable | Mean±SE | CV (%) | |
| Sweating Rate (L·hr$^{-1}$) | 1.4 ± 0.1 | 30.8 | SFR |
| Sweating Rate (mL·kg$^{-1}$·hr$^{-1}$) | 19.4 ± 1.7 | 28.5 | |
| Sweat [Na] -- Arm (mEq·L$^{-1}$) | 39.6 ± 2.0 | 42.6 | Concentration |
| Sweat [Na] -- Back (mEq·L$^{-1}$) | 47.2 ± 2.3 | 41.2 | |
| Mean Sweat [Na] -- Arm, Back (mEq·L$^{-1}$) | 43.4 ± 2.1 | 40.0 | |
| Na Loss -- Arm (mEq·hr$^{-1}$) | 56.5 ± 3.9 | 58.7 | Loss Rates |
| Na Loss -- Back (mEq·hr$^{-1}$) | 66.8 ± 4.5 | 56.2 | |
| Mean Na Loss -- Arm, Back (mEq·hr$^{-1}$)  dNa/dT | 61.6 ± 4.1 | 56.0 | |
| Na Loss -- Arm (mEq·hr$^{-1}$·kg$^{-1}$) | 0.8 ± 0.1 | 57.5 | |
| Na Loss -- Back (mEq·hr$^{-1}$·kg$^{-1}$) | 0.9 ± 0.1 | 54.5 | |
| Mean Na Loss -- Arm, Back (mEq·hr$^{-1}$·kg$^{-1}$) dNa/dW | 0.9 ± 0.1 | 54.0 | |

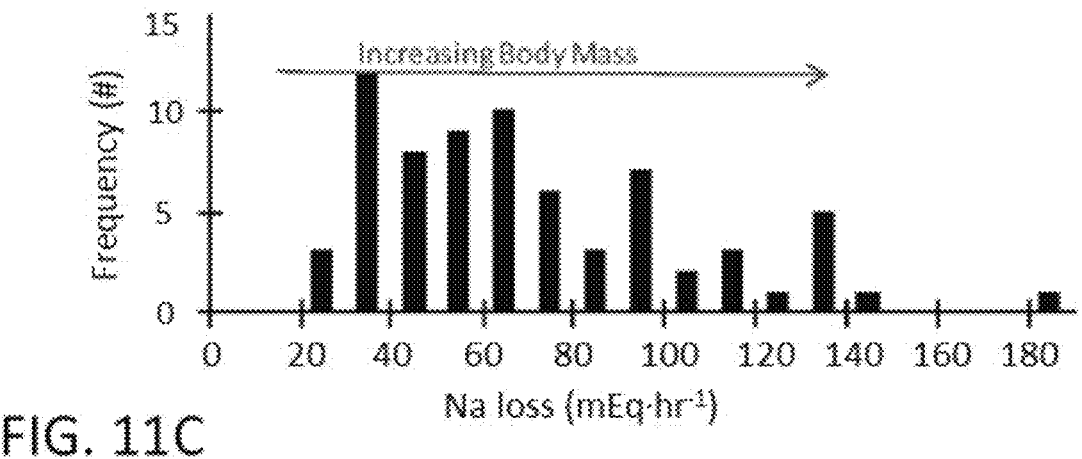

FIG. 11C

Estimated sodium loss during moderate intensity exercise. (Na loss is calculated as whole body sweat rate x mean sweat [Na]).

Sweat Stds for Typical User (KSI, ACSM, GSSI, Runners World)

| BSA | Temp (°F) | Sweat (oz/min) | SFR2 | BSA | Temp (°F) | Sweat (oz/min) | SFR2 |
|---|---|---|---|---|---|---|---|
| 100 lbs | 50 | 0.3 | 0.61045569 Zone1 | 200 lbs | 50 | 0.6 | |
| Ave Ht 60" | 60 | 0.3 | | Ave Ht 60" | 60 | 0.6 | |
| Ave BSA ($m^2$) | 70 | 0.3 | | Ave BSA ($m^2$) | 70 | 0.7 | |
| 1.45335018 | 80 | 0.4 | | 2.26003281 | 80 | 0.7 | |
| | 90 | 0.4 | | | 90 | 0.8 | |
| | 100 | 0.5 | 0.95638058 Zone 2 | | 100 | 0.9 | 1.21696552 |
| 120 lbs | 50 | 0.4 | | 220 lbs | 50 | 0.7 | |
| Ave Ht 66" | 60 | 0.4 | | Ave Ht 60" | 60 | 0.7 | |
| Ave BSA ($m^2$) | 70 | 0.4 | | Ave BSA ($m^2$) | 70 | 0.7 | |
| 1.65707416 | 80 | 0.4 | | 2.38071595 | 80 | 0.8 | |
| | 90 | 0.5 | | | 90 | 0.9 | |
| | 100 | 0.6 | 0.99942278 | | 100 | 1.0 | 1.26711883 Zone 3 |
| 140 lbs | 50 | 0.4 | | 240 lbs | 50 | 0.7 | |
| Ave Ht 70" | 60 | 0.4 | | Ave Ht 60" | 60 | 0.8 | |
| Ave BSA ($m^2$) | 70 | 0.5 | | Ave BSA ($m^2$) | 70 | 0.8 | |
| 1.83312867 | 80 | 0.5 | | 2.48206796 | 80 | 0.9 | |
| | 90 | 0.6 | | | 90 | 1.0 | |
| | 100 | 0.7 | 1.04863311 | | 100 | 1.2 | 1.42995279 |
| 160 lbs | 50 | 0.5 | | 260+ lbs | 50 | 0.8 | |
| Ave Ht 60" | 60 | 0.5 | | Ave Ht 60" | 60 | 0.8 | |
| Ave BSA ($m^2$) | 70 | 0.5 | | Ave BSA ($m^2$) | 70 | 1.0 | Zone 4 |
| 1.99289396 | 80 | 0.6 | | 2.57944069 | 80 | 1.4 | |
| | 90 | 0.7 | | | 90 | 1.8 | |
| | 100 | 0.7 | 1.09812224 | | 100 | 2.2 | 2.52287251 |
| 180 lbs | 50 | 0.5 | | | | | |
| Ave Ht 60" | 60 | 0.6 | | | | | |
| Ave BSA ($m^2$) | 70 | 0.6 | | Elite Pro/NCAA athletes much higher than typical users | | | |
| 2.13553028 | 80 | 0.7 | | | | | |
| | 90 | 0.7 | | | | | |
| | 100 | 0.8 | 1.16325978 | | | | |

FIG. 11D

VO2 Max for Men (mL·kg⁻¹·min⁻¹)

|  | Age (years) | | | | | |
|---|---|---|---|---|---|---|
| Rating | 18-25 | 26-35 | 36-45 | 46-55 | 56-65 | 65+ |
| Excellent | >60 | >56 | >51 | >45 | >41 | >37 |
| Good | 52-60 | 49-56 | 43-51 | 39-45 | 36-41 | 33-37 |
| Above Average | 47-51 | 43-48 | 39-42 | 36-38 | 32-35 | 29-32 |
| Average | 42-46 | 40-42 | 35-38 | 32-35 | 30-31 | 26-28 |
| Below Average | 37-41 | 35-39 | 31-34 | 29-31 | 26-29 | 22-25 |
| Poor | 30-36 | 30-34 | 26-30 | 25-28 | 22-25 | 20-21 |
| Very Poor | <30 | <30 | <26 | <25 | <22 | <20 |

VO2 Max for Women (mL·kg⁻¹·min⁻¹)

|  | Age (years) | | | | | |
|---|---|---|---|---|---|---|
| Rating | 18-25 | 26-35 | 36-45 | 46-55 | 56-65 | 65+ |
| Excellent | >56 | >52 | >45 | >40 | >37 | >32 |
| Good | 47-56 | 45-52 | 38-45 | 34-40 | 32-37 | 28-32 |
| Above Average | 42-46 | 39-44 | 34-37 | 31-33 | 28-31 | 25-27 |
| Average | 38-41 | 35-38 | 31-33 | 28-30 | 25-27 | 22-24 |
| Below Average | 33-37 | 31-34 | 27-30 | 25-27 | 22-24 | 19-21 |
| Poor | 28-32 | 26-30 | 22-26 | 20-24 | 18-21 | 17-18 |
| Very Poor | <28 | <26 | <22 | <20 | <18 | <17 |

Human Use Self-Calibration (H-SCAL)

Sweat Loss' = SFR × BSA × Fb $$SFR = \frac{\text{Ratio of Na/K}}{Fs} \times Fp$$

Fb = Fcondition × Fmass × Ftemp

Sweat Loss" = Weigh in − Weigh out $$Fp = \frac{\text{Sweat Loss"} - \text{Sweat Loss'}}{\text{Sweat Loss"}}$$

where:

Fs = 10 (default)

Fp = 1 (default)

Fcondition = 1 (default)

Fmass = 1 (default)

Ftemp = 1 (default)

Fcondition' = Fcondition × Fp

| $VO_2$ max | Fcondition |
|---|---|
| ≥ 60 | 1.005 |
| 50 ≤ $VO_2$ max < 60 | 1.0025 |
| 40 ≤ $VO_2$ max < 50 | 1.001 |
| 30 ≤ $VO_2$ max < 40 | 1.0 |

| Basic Concentration Conversions | | | | |
|---|---|---|---|---|
| K (mV) | K (mM) | Na (mV) | Na (mM) | |
| 0 | 0 | 0 | 0 | Specified Range |
| 17 | 40 | 57 | 110 | Specified Range |
| 30 | 14 | 50 | 17 | Test Range |
| 80 | 135 | 130 | 171 | Test Range |
| K Ratio | 2.4 | Na Ratio | 1.9 | mM/mV |

FIG. 12B

Ratiometric Analysis

Trend 1 Sweat Loss Ratio – User Sweat Loss vs. Norm Sweat Loss $$SLR = SL1/SL2 \quad \begin{matrix} >1 & \text{Sweating Trend More Than Norm} \\ <1 & \text{Sweating Trend Less Than Norm} \end{matrix}$$

Trend 2 Electrolyte Trend Ratio – User 1$^{st}$ Time Derivative vs. Norm Electrolyte Change $$\frac{dNa\ (mV)}{dT} \times SLR \times Na\ Loss\ Norm = Na\ Trend\ (Approx\ Loss\ Given\ User\ Sensor\ Changes)$$

$$\frac{dK\ (mV)}{dT} \times SLR \times K\ Loss\ Norm = K\ Trend\ (Approx\ Loss\ Given\ User\ Sensor\ Changes)$$

FIG. 12C

| Basic mV Ratios (Same as mM Ratios) | | | |
|---|---|---|---|
| Na/K (mV/mV) | SFR1 | | |
| 1 | | | |
| 2 | | | |
| 3 | | | |
| 4 | 0.00 | | Zone 1 |
| 5 | 0.25 | | |
| 6 | 0.50 | 0.125 | |
| 7 | 0.63 | | Zone 2 |
| 8 | 0.75 | | |
| 9 | 0.88 | | |
| 10 | 1.00 | 0.083 | |
| 11 | 1.08 | | Zone 3 |
| 12 | 1.17 | | |
| 13 | 1.25 | | |
| 14 | 1.33 | | |
| 15 | 1.42 | | |
| 16 | 1.50 | 0.250 | |
| 17 | 1.75 | | Zone 4 |
| 18 | 2.00 | | |
| 19 | 2.25 | | |
| 20 | 2.50 | | |
| 21 | 2.75 | | Zone 5 |
| 22 | 3.00 | | |
| 23 | 3.25 | | Zone 6 |
| 24 | 3.50 | | |

FIG. 13A

Color Thresholds

| | K | Level 1 Na 1 | Level 2 Na 2 | Level 3 Na 3 | HYDRATION % Body Mass | SLR | Na Trend | K Trend |
|---|---|---|---|---|---|---|---|---|
| Range Low | 0 | 20 | 20 | 20 | 0 | 0 | TBD | |
| Range High | 20 | 110 | 110 | 110 | 7 | 3 | | |
| Red Lo | <3 | <36 | <37 | <54 | | <0.25 | | |
| Yellow Lo1 | 3 | 36 | 38 | 54 | | 0.25 | | |
| Yellow Lo2 | 3.9 | 37 | 39 | 56 | | 0.49 | | |
| Green Lo1 | 4 | 38 | 40 | 57 | | 0.50 | | |
| Green Lo2 | 4.9 | 42 | 44 | 63 | 0 | 0.99 | | |
| Blue Low | 5 | 43 | 45 | 65 | 1.00% | 1.00 | | |
| Blue High | 6 | 45 | 47 | 68 | 1.99% | 1.00 | | |
| Green Hi 1 | 6.1 | 46 | 48 | 70 | 2.00% | 1.10 | | |
| Green Hi 2 | 9 | 48 | 50 | 73 | 2.99% | 1.50 | | |
| Yellow Hi 1 | 9.1 | 49 | 51 | 74 | 3.00% | 1.51 | | |
| Yellow Hi 2 | 14 | 59 | 62 | 89 | 3.99% | 1.75 | | |
| Red Hi | >14 | >59 | >62 | >89 | 4% | >1.75 | | |
| | | I1 Std | I2 Ratio | I3 Ratio | SL1 Derived via Sensors | SL1/SL2 Compares to Normal | | |
| | | 1.0000 | 0.04651163 | 0.44444444 | | | | |
| | | SFR <1 | 1<SFR<2 | SFR>2 | | | | |

$uL/min/cm^2$
Only Showing 1 Na in Gauge

FIG. 13B

| User Input at Session Start | | From Phone | From Sensor |
|---|---|---|---|
| Intense Selection | User Wt Input | Atm Temp | Na/K Ratio |
| User Input Low (1) | Wt < 140 (1) | T (°F) < 80 (1) | < 10 (1) |
| User Input Med (2) | 140 <Wt < 200 (2) | 80 < T (°F) < 90 (2) | 10-18 (2) |
| User Input High (3) | Wt > 200 (3) | T (°F) > 90 (3) | > 18 (3) |
| | | Not Skin T | |

These values should be adjustable in the CLOUD

| | | |
|---|---|---|
| Level 1 | Add Up Scores from inputs Above | <4 |
| Level 2 | Intens+Wt+Temp+Ratio | 4-10 |
| Level 3 | | >10 |

Multi-User View
(Active Session Chrono)

Selected User History
(Multi-Biomarker History Chrono)

Reports Include Hydra, Neuro, Chrono, Cross-Core, Trending, Hot Spot, and Other User-defined Graphs/Tables

| User | |
|---|---|
| Hourly Login Limit | Number(0,0) |
| IDE Workspace | Lookup(IDE Works) |
| Info Emails | Checkbox |
| Internal Subtype | Picklist |
| Language | Picklist |
| Lead Owner | Text(50) |
| Locale | Picklist |
| Manager | Hierarchy |
| Name | Name |
| Nexternal Company name | Text(50) |
| Nexternal Password | Text(50) |
| Nexternal Task Scheduler ID | Text(50) |
| Nexternal Username | Text(50) |
| Nickname | Text(40) |
| Phone | Phone |
| Portal Role Level | Picklist |
| Profile | Lookup(Profile) |
| Role | Lookup(Role) |
| SAML Federation ID | Text(512) |
| Self-registered via Customer Portal | Checkbox |

*All
Displaying records 1-31      Number of records  31

| Dtstamp | Owner Last Name | Q | Na | Potas | Magn | Gluc | Co2 | Temp |
|---|---|---|---|---|---|---|---|---|
| 12/31/2013 2:08 PM | Ackerman |  | 140.0 | 4.2 | 1.8 | 112.0 | 38.0 |  |
| 12/31/2013 1:40 PM | Ackerman | ■ | 141.0 | 4.2 | 1.6 | 124.0 | 38.0 |  |
| 12/13/2013 2:21 PM | Pont |  | 137.0 | 3.7 | 2.2 | 103.0 | 38.0 |  |
| 12/13/2013 2:26 PM | Pont |  | 140.0 | 3.9 | 2.2 | 99.0 | 37.0 |  |
| 12/22/2013 7:00 PM | Pont |  | 137.0 | 3.9 | 2.0 | 103.0 | 38.0 |  |
| 12/22/2013 7:01 PM | Pont |  | 140.0 | 3.8 | 2.0 | 114.0 | 36.0 |  |
| 12/22/2013 7:04 PM | Pont |  | 137.0 | 3.9 | 2.1 | 121.0 | 374.0 |  |
| 12/22/2013 7:07 PM | Pont |  | 140.0 | 3.8 | 1.9 | 108.0 | 39.0 |  |
| 12/22/2013 7:13 PM | Pont |  | 139.0 | 3.9 | 2.1 | 133.0 | 37.0 |  |
| 12/26/2013 12:46 PM | Fenner |  | 139.0 | 3.5 | 1.8 | 122.0 | 35.0 |  |
| 12/28/2013 3:20 PM | Fenner |  | 140.0 | 3.8 | 2.0 | 114.0 | 36.0 |  |
| 12/28/2013 4:27 PM | Fenner |  | 137.0 | 3.9 | 2.1 | 121.0 | 37.0 |  |
| 12/28/2013 5:50 PM | Fenner |  | 140.0 | 3.8 | 1.9 | 108.0 | 39.0 |  |
| 12/28/2013 8:00 PM | Fenner |  | 139.0 | 3.9 | 2.1 | 133.0 | 37.0 |  |
| 12/28/2013 7:00 PM | Ackerman |  | 139.0 | 3.5 | 1.8 | 122.0 | 35.0 |  |
| 12/27/2013 10:10 AM | Ackerman |  | 140.0 | 3.8 | 2.0 | 114.0 | 36.0 |  |
| 12/27/2013 10:21 AM | Ackerman |  | 137.0 | 3.9 | 2.1 | 121.0 | 37.0 |  |
| 12/28/2013 10:21 AM | Ackerman |  | 140.0 | 3.8 | 1.9 | 108.0 | 39.0 |  |
| 12/26/2013 7:00 PM | Ackerman |  | 139.0 | 3.9 | 2.1 | 133.0 | 37.0 |  |

FIG. 27

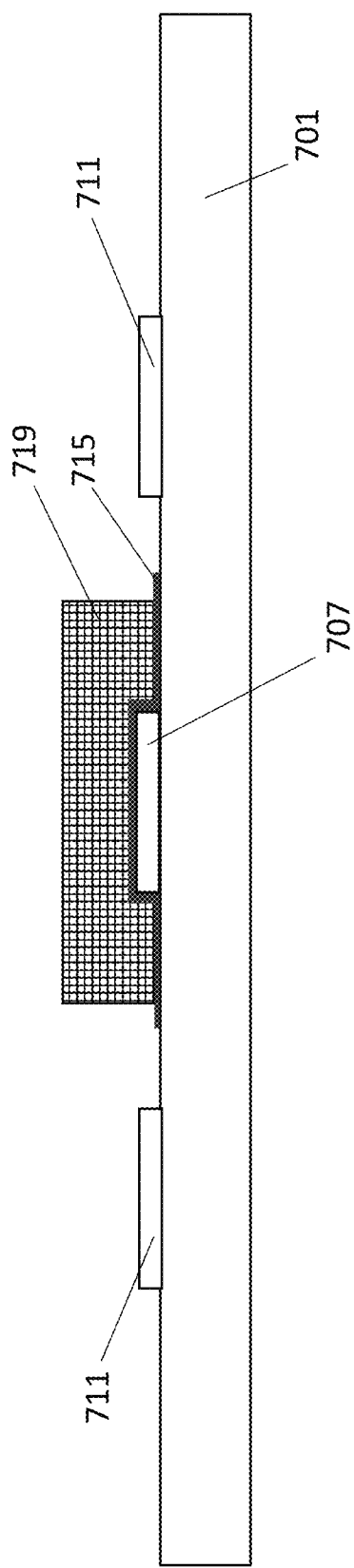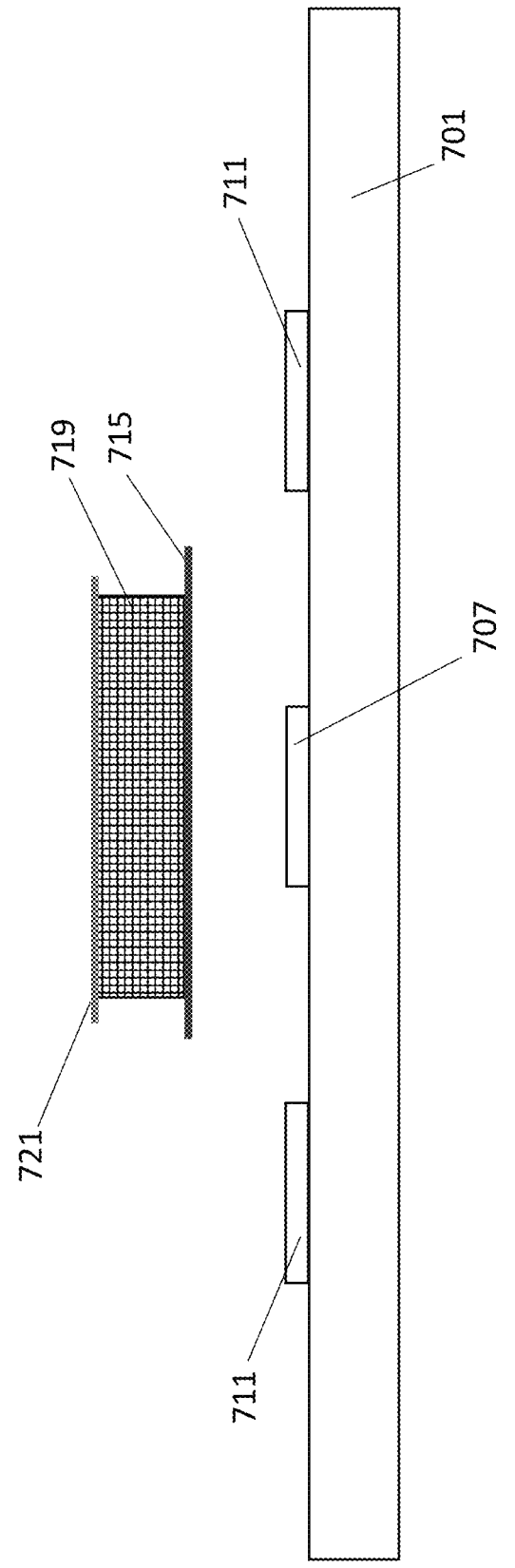
FIG. 46A
FIG. 46B

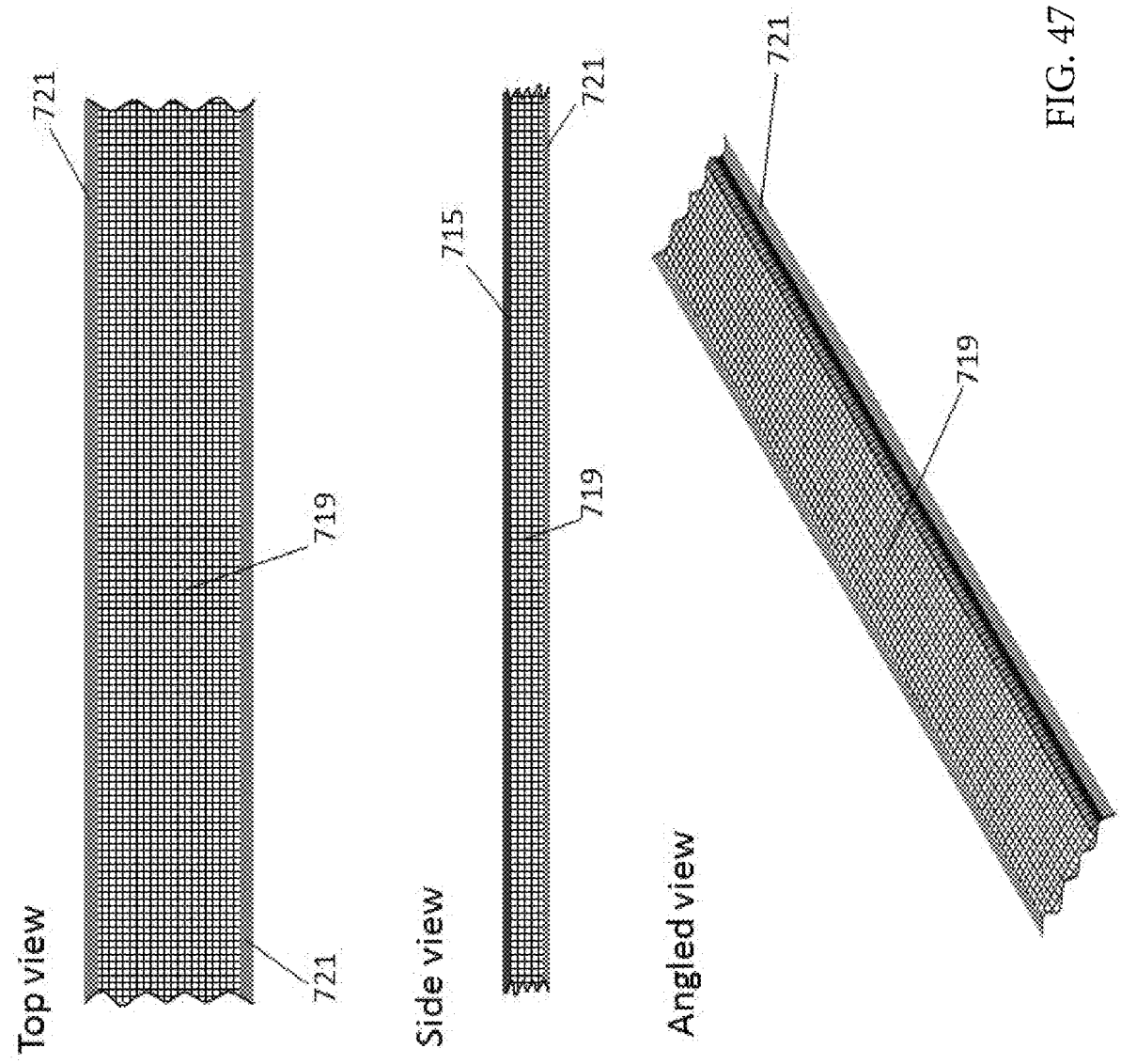

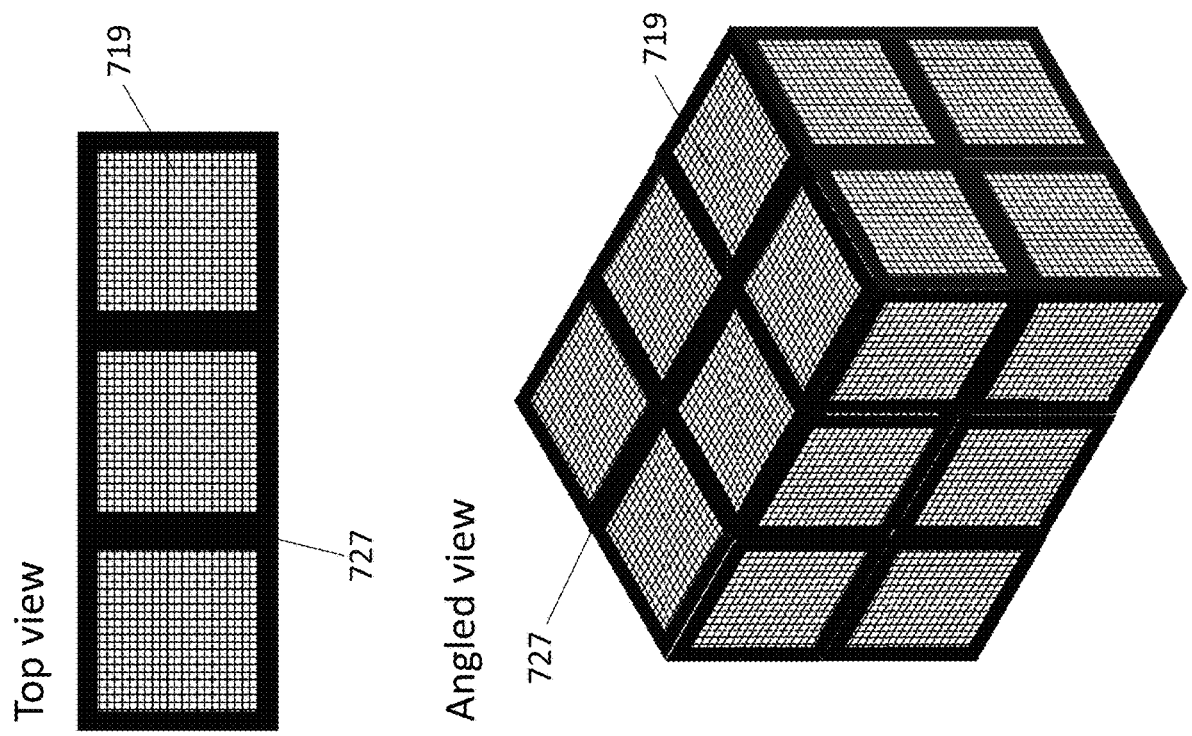

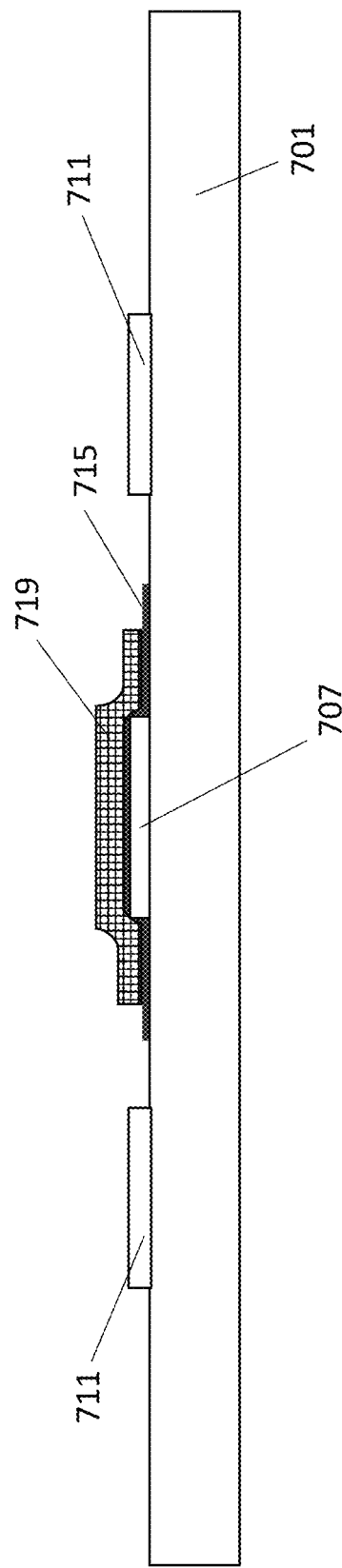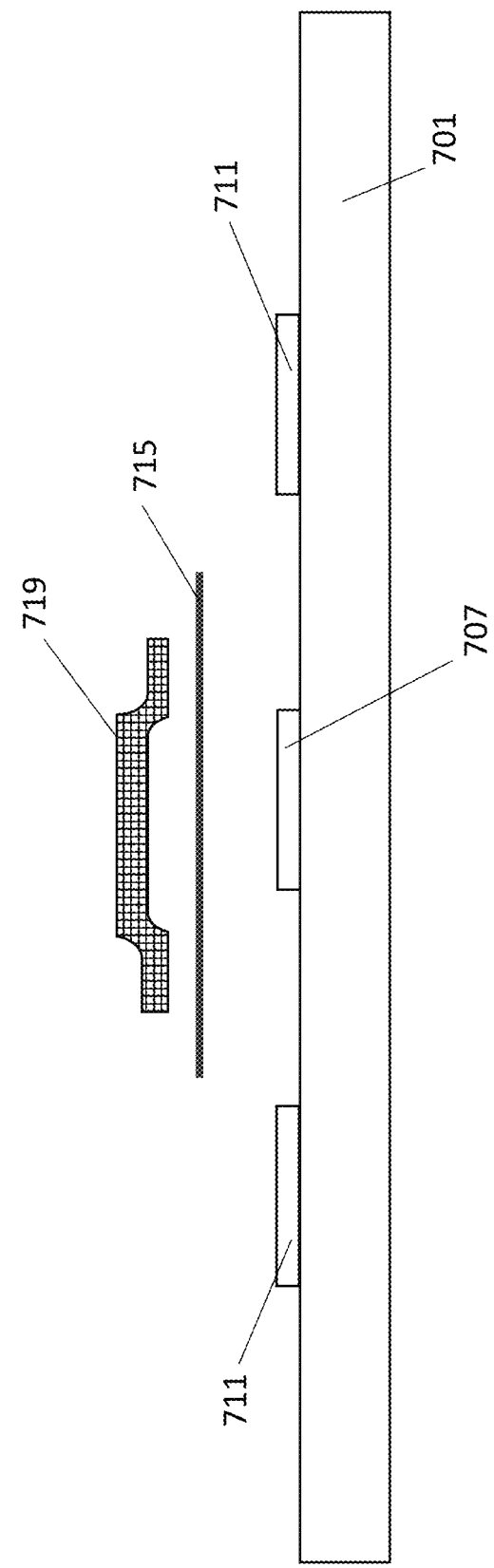
FIG. 52A
FIG. 52B

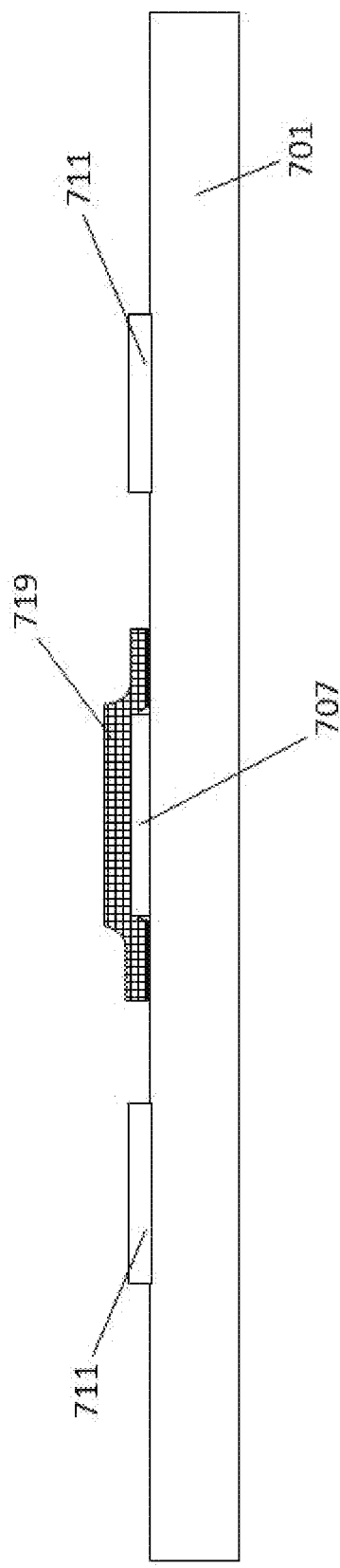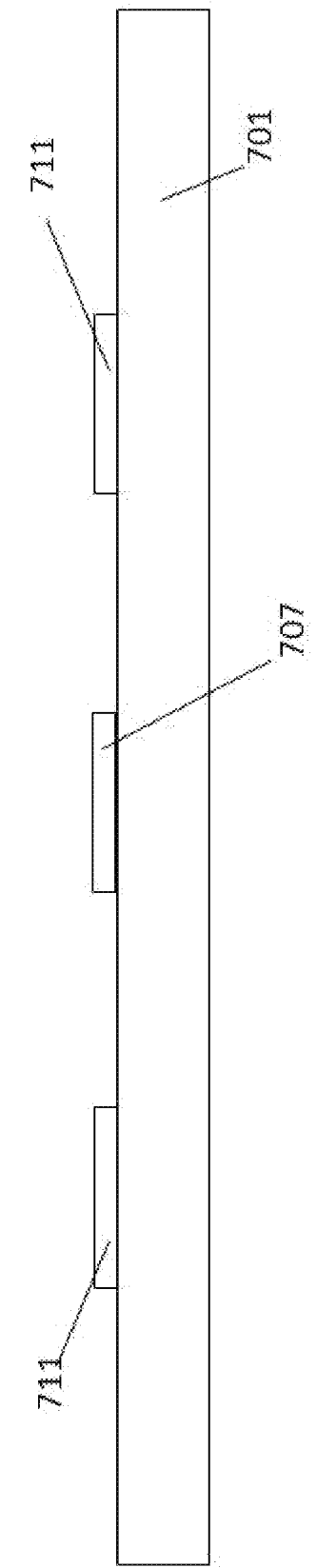
FIG. 53A
FIG. 53B

METHOD FOR MANUFACTURING A BIOLOGICAL FLUID SENSOR

CROSS REFERENCE TO RELATED APPLICATIONS

This application is a continuation-in-part of U.S. application Ser. No. 15/177,703, filed Jun. 9, 2016, which is a continuation-in-part of U.S. application Ser. No. 15/019,006, filed Feb. 9, 2016, which claims priority from U.S. Provisional Patent Application No. 62/130,047, filed Mar. 9, 2015, each of which is incorporated herein by reference in its entirety.

BACKGROUND OF THE INVENTION

1. Field of the Invention

The present invention is generally directed to a method for manufacturing a device operable for collecting and analyzing biological fluid inputs, calculating biological fluid concentrations and ratios, and transmitting biological fluid values to a transceiver device.

2. Description of the Prior Art

Generally, biomarkers from biological fluid have significant prognostic and/or diagnostic utility, such as predicting disease, nutritional imbalance, or psychological or physical stress; however, many of the most utilized biomarkers are collected from blood. The ability to predict events through non-invasive means, such as sweat detection, provides great utility to persons under physical stress, particularly individuals in the process of physical activity or exercise. The ability to monitor sweat biomarkers in real time and continuously during activity allows an individual to make informed decisions regarding hydration, nutrition, and exertional status, and recovery, all variables that moderate physical performance.

For example, hydration status is a predictor of physical performance; dehydration as low as 1% of body mass can impair performance. Prior art detection and treatment, as shown in FIG. 1, is currently at the stages of when symptoms present, performance degrades, and/or injury presents. Determining hydration through sweat biomarkers before dehydration symptoms present has many benefits, such as reducing fatigue, cramps, and headaches. Therefore, developing a device and system for non-invasively obtaining biomarkers, such as through sweat, is needed.

Sweat contains a multitude of biomarkers; any substance aqueously dissolvable in the blood can present in the sweat by way of eccrine glands. The sweat biomarkers can be small molecules (molecular weight <900 Daltons), proteins, metabolites, and/or electrolytes. Well-known electrolytes in sweat are sodium and potassium. As shown in FIG. 2, potassium concentration is not dependent upon sweat rate due to the passive diffusive transport of potassium, while sodium and chloride concentrations in sweat are dependent upon sweat rate due to the active transport of sodium. Thus, monitoring sodium or chloride concentrations is an accurate, indirect means of indicating hydration status of an individual. Therefore, developing a sweat biomarker device that can communicate to an individual real-time biomarker data is needed.

U.S. Pat. No. 6,198,953 for method and system for continuous sweat collection and analysis by inventors Webster, et al. filed Mar. 11, 1999 and issued Mar. 6, 2001 is directed to a method and system of the invention providing especially for continuously obtaining and analyzing, on a real time basis, sweat from a selected area of skin on the body of a person, especially a neonate, being diagnosed for cystic fibrosis, by causing sweating of the selected area of skin, by placing an electrically positive iontophoretic electrode device of a set of said devices over the selected area of skin preferably within a previously placed receiving and holding device which, following the induction of sweat and removal of the electrically positive iontophoretic electrode device, receives a sweat-sensing electrode device that continuously sends electrical signals to sweat analysis circuitry for providing a digital readout of the ionic composition of the sweat.

U.S. Pat. No. 8,388,534 for apparatus for providing skin care information by measuring skin moisture content and method and medium for the same by inventors Jang, et al. filed Sep. 24, 2007 and issued Mar. 5, 2013 is directed to an apparatus for providing skin care information, the apparatus including: an electrode unit supplying a voltage to a user's skin and detecting a current signal in the user's skin; a measurement control unit measuring the user's skin moisture content and sweat gland activity by using the detected current signal; a data calculation unit deriving skin moisture content information by using the skin moisture content and the sweat gland activity, and generating skin care information corresponding to the skin moisture content information; and an information provider providing the user with the generated skin care information is provided.

U.S. Pat. No. 7,575,549 for an apparatus and method for increasing, monitoring, measuring, and controlling perspiratory water and solid loss at reduced ambient pressure by inventor Miller filed Jul. 30, 2004 and issued Aug. 18, 2009 is directed to a device for increasing, monitoring, and measuring perspiration water and solid loss at reduced ambient pressure, comprising a sealed chamber capable of maintaining less than atmospheric pressure for an extended period of time and a gasket-sealed door accessing the chamber. An algorithm allowing for continuous calculations of sweat loss and fluid replacement requirements of the occupant of the chamber is disclosed.

US Publication No. 20140330096 for method for performing a physiological analysis with increased reliability by inventor Brunswick filed Nov. 12, 2012 and published Nov. 6, 2014 is directed to a method for performing an electrophysiological analysis implemented in a system includes: a series of electrodes to be placed on different regions of the human body; a DC voltage source controlled so as to produce DC voltage pulses; a switching circuit for selectively connecting the active electrodes to the voltage source, the active electrodes forming an anode and a cathode, and for connecting at least one other high-impedance passive electrode used to measure the potential reached by the body; and a measuring circuit for reading data representative of the current in the active electrodes, and data representative of the potentials generated on at least certain high-impedance electrodes in response to the application of the pulses, the data allowing a value to be determined for the electrochemical conductance of the skin. The method also regenerates a high-impedance electrode connected to the voltage source as a cathode.

US Publication No. 20140350432 for assessment of relative proportions of adrenergic and cholinergic nervous receptors with non-invasive tests by inventors Khalfallah, et al. filed Aug. 8, 2014 and published Nov. 27, 2014 is directed to a system and method for assessing relative proportions of cholinergic and adrenergic nervous receptors in a patient. The system includes: an anode, a cathode, and passive electrode for placement on different regions of the patient body. The method generally includes: applying DC voltage pulses of varying voltage values to stress sweat glands of the patient, collecting data representing the current between the anode and the cathode and the potential of the anode, the cathode, and the passive electrode for each of the different DC voltage, and computing data representing the electrochemical skin conductance of the patient. The computed data representing the electromechanical skin conductance of the patient is reconciled with reference data from control patients having known relative proportions of cholinergic and adrenergic nervous receptors. Thus, the relative proportions of cholinergic and adrenergic nervous receptors in the patient can be determined.

US Publication No. 20150019135 for motion sensor and analysis by inventors Kacyvenski, et al. filed Jun. 3, 2014 and published Jan. 15, 2015 is directed to the performance of an individual being monitored based on measurements of a conformal sensor device. An example system includes a communication module to receive data indicative of a measurement of at least one sensor component of the conformal sensor device. The sensor component obtains measurement of acceleration data representative of an acceleration proximate to the portion of the individual. A comparison of a parameter computed based on the sensor component measurement to a preset performance threshold value provides an indication of the performance of the individual.

The article Implementation of a Microfluidic Conductivity Sensor—A Potential Sweat Electrolyte Sensing System for Dehydration Detection, by Liu, et al. in Conf Proc IEEE Eng Med Biol Soc, 2014:1678-81, discusses the implementation of a microfluidic conductivity sensor—a potential sweat electrolyte sensing system for dehydration detection.

US Publication No. 20130245388 for electronics for detection of a condition of tissue by inventors Rafferty, et al. filed Sep. 4, 2012 and published Sep. 19, 2013 is directed to an apparatus for monitoring a condition of a tissue based on a measurement of an electrical property of the tissue. In an example, the electrical property of the tissue is performed using an apparatus disposed above the tissue, where the apparatus includes at least two conductive structures, each having a non-linear configuration, where the at least two conductive structures are disposed substantially parallel to each other. In another example, the electrical property of the tissue is performed using an apparatus disposed above the tissue, where the apparatus includes at least one inductor structure.

U.S. Pat. No. 5,690,893 for analyzer having sensor with memory device by inventors Ozawa, et al. filed Jun. 5, 1995 and issued Nov. 25, 1997 is directed to an analyzer including an exchangeable and consumable element such as a sensor, column or reagent the characteristic of which specifies an analyzing condition. The element is provided with a nonvolatile semiconductor memory which holds an analyzing condition adapted for the element as data. When the element is mounted on an analyzer body, a controller of the analyzer reads the analyzing condition from the memory to update an analyzing condition inherently provided in the analyzer body. The result of analysis and/or operational history information of use of the element may be written into the memory with which the element is provided.

U.S. Pat. No. 8,241,697 for formation of immobilized biological layers for sensing by inventors Collier, et al. filed Dec. 20, 2007 and issued Aug. 14, 2012 is directed to enzyme immobilization compositions comprising: one or more enzymes, a humectant, an acrylic-based monomer, a water-soluble organic photo-initiator and a water-soluble acrylic-based cross-linker in a substantially homogeneous aqueous mixture. The invention is also directed to methods for forming sensors comprising such compositions and to apparati for forming arrays of immobilized layers on an array of sensors by dispensing such compositions onto a substrate.

WIPO Publication No. WO2016061362 for sweat sensing device communication security and compliance by inventors Heikenfeld, et al. filed Oct. 15, 2015 and published Jun. 16, 2016 is directed to an invention that addresses confounding difficulties involving continuous sweat analyte measurement. Specifically, the invention provides: at least one component capable of monitoring whether a sweat sensing device is in sufficient contact with a wearer's skin to allow proper device operation; at least one component capable of monitoring whether the device is operating on a wearer's skin; at least one means of determining whether the device wearer is a target individual within a probability range; at least one component capable of generating and communicating alert messages to the device user(s) related to: wearer safety, wearer physiological condition, compliance with a requirement to wear a device, device operation; compliance with a behavior requirement, or other purposes that may be derived from sweat sensor data; and the ability to utilize aggregated sweat sensor data that may be correlated with information external to the device to enhance the predictive capabilities of the device.

Published article by Rose, et al. in IEEE Transactions on Biomedical Engineering, Nov. 6, 2014, pages 1-9, discusses an adhesive RFID sensor patch for monitoring of sweat electrolytes.

Although biomarkers in sweat are appreciated, specifically electrolytes and glucose, a system and method is still lacking that continuously analyzes sweat biomarkers in real time and transmits data to a user, which informs the user of his or her health status.

SUMMARY OF THE INVENTION

The present invention provides a method of fabrication for a biological fluid sensor with electronic, electrochemical and chemical components.

The fabrication method comprises steps for manufacturing an apparatus comprising at least one electrochemical sensor, at least one microcontroller, and at least one transceiver. The fabrication process includes the steps of substrate fabrication, circuit fabrication, pick and place, reflow soldering, electrode fabrication, membrane fabrication, sealing and curing, layer bonding, and dressing.

The present invention further includes a metallization paste and sequence step for a reference probe; and a metallization application and sequence step for at least one active probe. The present invention further includes method steps for creating a sensor with line and space characteristics configured and designed for sensing and/or analysis of sweat flow rate and electrolyte probes. The present invention further includes a method for membrane fabrication with precision ionophore application and curing, and includes a method for dressing fabrication with laser cutting, bonding, and assembly steps for microfluidic and dressing fabrication.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 11A shows a table of various sweat characteristics including basic ratio for sweat flow rate, body surface area calcs, and sweat loss & body mass loss calcs.

FIG. 11C shows tables including work level, zone, SFR, mV ratio, Na Loss, K Loss, Typ Wt, sweating rate and sweat sodium concentration and a chart of frequency vs. Na loss.

FIG. 11D shows a table of sweat stds for a typical user.

FIG. 11F shows one embodiment of human use self-calibration for the sensor apparatus.

FIG. 12A shows a table of basic electrolyte concentration conversions.

FIG. 12B shows a table of ratiometric analysis used within the sensor apparatus.

FIG. 12C shows a table of basic mV ratios.

FIG. 13A shows thresholds for electrolyte concentrations.

FIG. 13B shows a table of user input at session start, input from phone, and input from sensor.

FIG. 27 shows an image of a user data base on the remote computer server.

FIG. 37 C shows another side perspective view of a sensor with a liquid ionophore coating.

FIG. 46A shows a side perspective view of a sensor with an ionophore covering after a carrier or film is removed following application of a pre-formed ionophore to an active electrode.

FIG. 46B shows an ionophore covering on a carrier or film prior to application on an active electrode.

FIG. 47 shows a top perspective view, a side perspective view, and an angled perspective view of an ionophore covering formed in a continuous shape that can be handled or applied on a carrier or film that becomes an integral part of the sensor.

FIG. 50 shows a top perspective view and an angled perspective view of an ionophore formed using an embedded strength approach.

FIG. 52A shows a side perspective view of an ionophore cast and placed on top of an active electrode using an adhesive or bonding film.

FIG. 52B shows an exploded side perspective view of an ionophore cast and placed on top of an active electrode using an adhesive or bonding film.

FIG. 53A shows a side perspective view of an ionophore cast and placed on top of an active electrode without using an adhesive or bonding film.

FIG. 53B shows an exploded side perspective view of an ionophore cast and placed on top of an active electrode without using an adhesive or bonding film.

DETAILED DESCRIPTION

Figure 1:
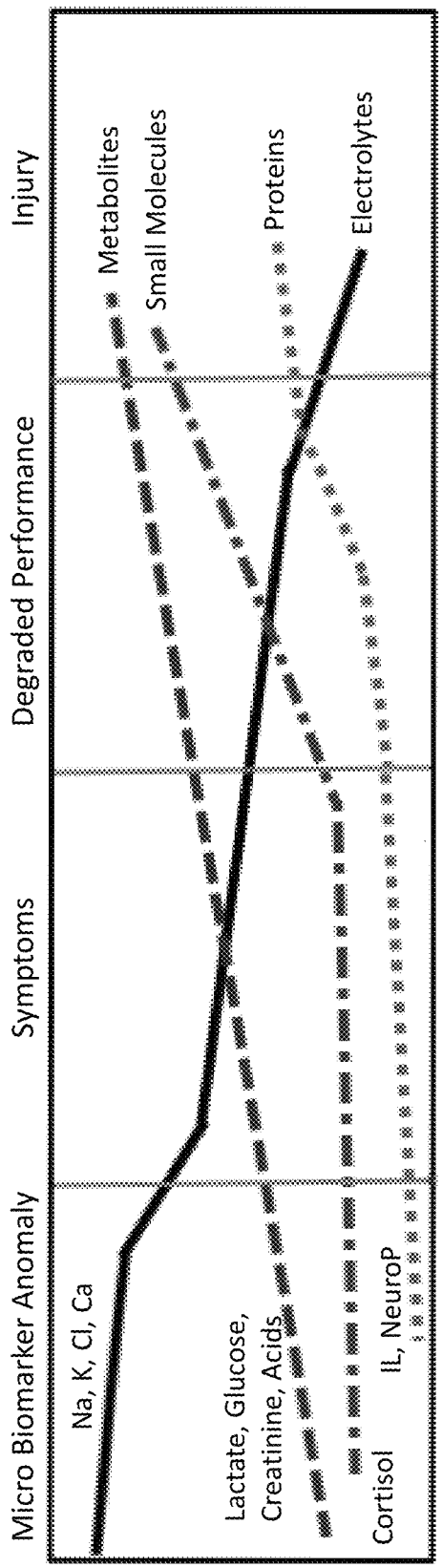
FIG. 1 shows a chart demonstrating biomarker types, changes in biomarker levels during progressive stages of injury, and physiological presentations associated with each stage of injury.
Figure 2:
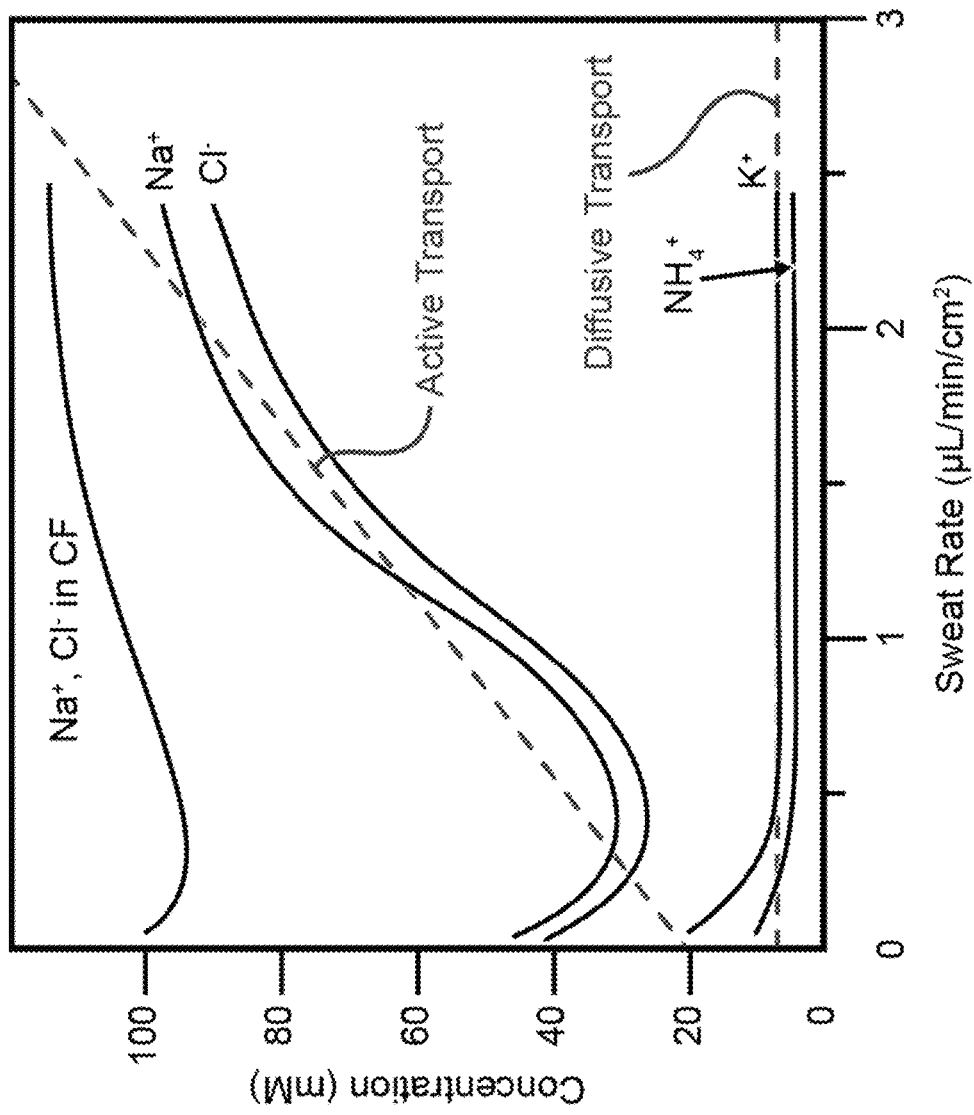
FIG. 2 shows a chart relating sweat rate to concentration of electrolytes.

The present invention includes methods of fabrication or manufacturing a biological fluid sensor device with electronic, electrochemical and chemical components for sensing and collecting biological fluid biomarkers, transmitting data to a transceiver device on a remote computing device for calculating biomarker data, and analyzing the data, and storing the data on the remote computing device or on a remote computer server.

The present invention provides methods of making the sensor apparatus or device for sensing sweat biomarkers that are operable and functional as described herein. A preferred embodiment is surface mount technology; it may provide better electrical performance compared to hand soldering; it allows use of smaller electrical components, denser layout, cheaper boards, and improved shock and vibration characteristics. Electrical components include chips, resistors, transistors, and capacitors. An automated dispenser configuration for dispensing an ionophore is preferably used to ensure a higher unit production rate when compared with the prior art. The automated dispenser provides for precise and rapid ionophore coating.

The sequence of the steps as well as the steps themselves is critical to the operational use and accuracy of the sensor apparatus. It is critical to initially install the surface mount parts and run through solder reflow before assembly of the sensor units. Subsequently, the heat sensitive parts to include the reference electrode, active electrodes, and ionophore coatings should be applied in that order. Following the last ionophore coating, the entire flexcircuit layer needs a minimum about 3 hour cure, which can be accelerated by UV and/or other rapid heating/drying processes. Following the cure period, the sensors can be final-assembled with the medical top cover, microfluidic, and double-sided skin adhesive layers using an industrial grade epoxy.

In a preferred embodiment, a microcircuit is printed directly on the flexible substrate using bare die bonding. The microcircuit is attached to the flexible substrate using any common bare die bonding process, such as eutectic, solder, adhesive, glass or silver-glass.

The fabrication process includes the steps of substrate fabrication, circuit fabrication, pick and place, reflow soldering, electrode fabrication where the earlier heat intensive processes through reflow are completed prior to the heat sensitive processes associated with starting with the build up and treatment of metalized traces on the substrate followed by membrane fabrication, sealing and curing, and dressing. In one embodiment, the substrate is a Kapton substrate. Without this process sequence, the electrodes build up unpredictable levels of oxidation and other undesirable surface conditions which negatively affect the accuracy within a sensor, as well as among multiple sensors. In a similar manner, the heat intensive steps also degrade/melt the ionophore coating, a polymer not tolerant of elevated temperature. Repeated heating and cooling exposes the ionophore to chemical changes and also creates microscopic holes in the coating, both which allow untargeted biomarker ions to penetrate the coating to reach the electrode which generates potential strength not associated with the target biomarker, thus reducing the accuracy.

The present invention further includes a metallization paste made of a stable metal (silver, gold, platinum, palladium) on top of the circuit trace metal (typically copper or gold) which is further stabilized through chemical and/or thermal annealing treatments to construct a reference probe; and a similar metallization application and sequence step for at least one active probe. The present invention further includes method steps for creating a sensor with line and space characteristics configured and designed for sensing and/or analysis of sweat flow rate and small protein probes.

The present invention further includes a method for membrane fabrication with precision ionophore application and curing. Sensor functionality and accuracy require precision placement with proper thickness of a small amount of ionophore polymer on the active electrodes to filter/prevent untargeted ions to reach the electrode. The amount is approximately 2 microliters with a designated viscosity placed in a clean assembly environment to completely cover the exposed active electrode on the skin-facing side of the flexcircuit. The coating shall preferably not exceed more than 0.5 mm from the edge of the electrode. The placement also preferably includes automated dispenser configuration and settings to ensure high speed or high rate manufacturing as well as manufacturing consistency that minimizes manufacturing accuracy variations.

The present invention still further includes a method for dressing fabrication with laser cutting, bonding, and assembly steps for microfluidic and dressing fabrication. Following the designated ionophore cure time, the flexcircuits with integrated parts, sensor electrodes are conformal sealed and cured. The sealed flex circuits are placed on a large sheet of top cover medical textile with previously laser precut patterns and adhesive up. The sealed flexcircuits adhere to the top cover via the cover's adhesive; they are mechanically precision-placed and pressed into place with the exposed sensor head facing up for permanent bonding using proprietary edge bonding patterns to allow for the proper flow/exit of sweat from the sensor heads out. Next, microfluidic units previously pre-cut to specification are inserted on top via the same mechanical precision placement equipment. And finally the mechanical placement equipment places a large sheet of double sided adhesive which were previously precut by laser to the same size and pattern as the top cover textile. The sheet and each of the laser precut patterns are precisely positioned above the semi-assembled units below and pressed into position for permanent bond. The individual units are then mechanically separated (punched) from their host sheets and collected in bins for automated packaging into individualized branded wrappers, and then inserted into branded boxes that are crated and palletized for shipment. The wrapper, box, crate, and pallet specifications are specified by our distribution partners' pack out plan and specified branding schema.

Figure 3:
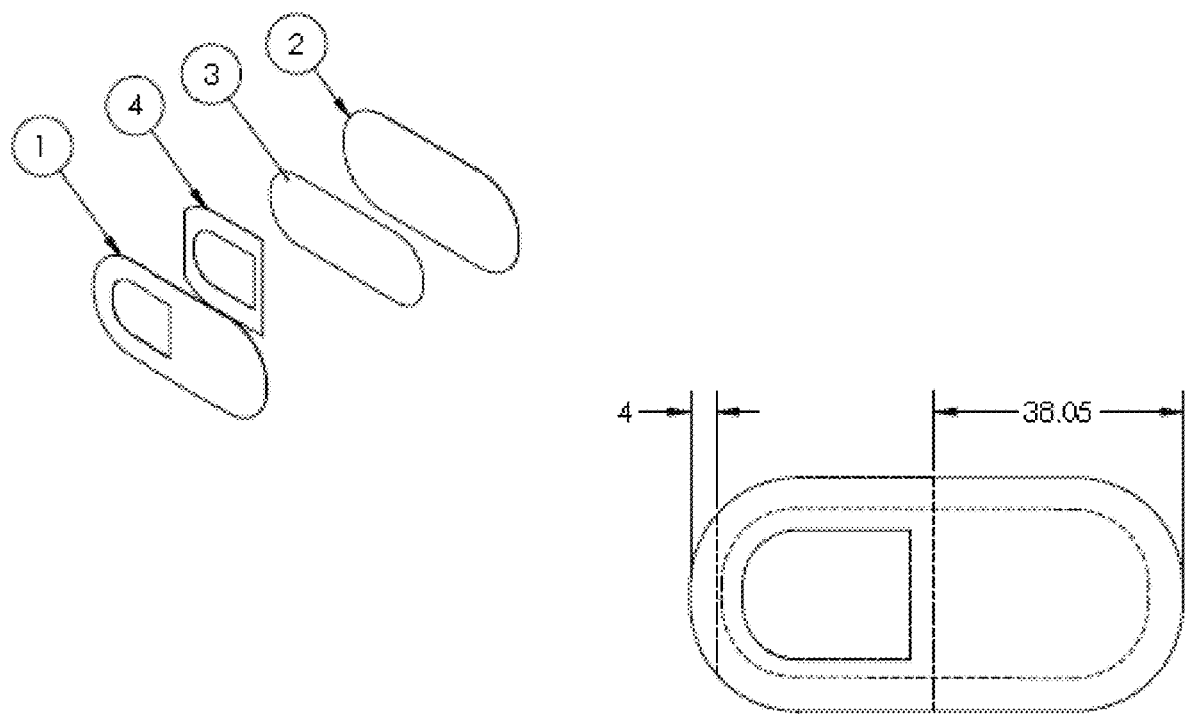
FIG. 3 shows the multiple layers and associated parts of the sensor apparatus and a top perspective view of the complete sensor apparatus.
Figure 4:
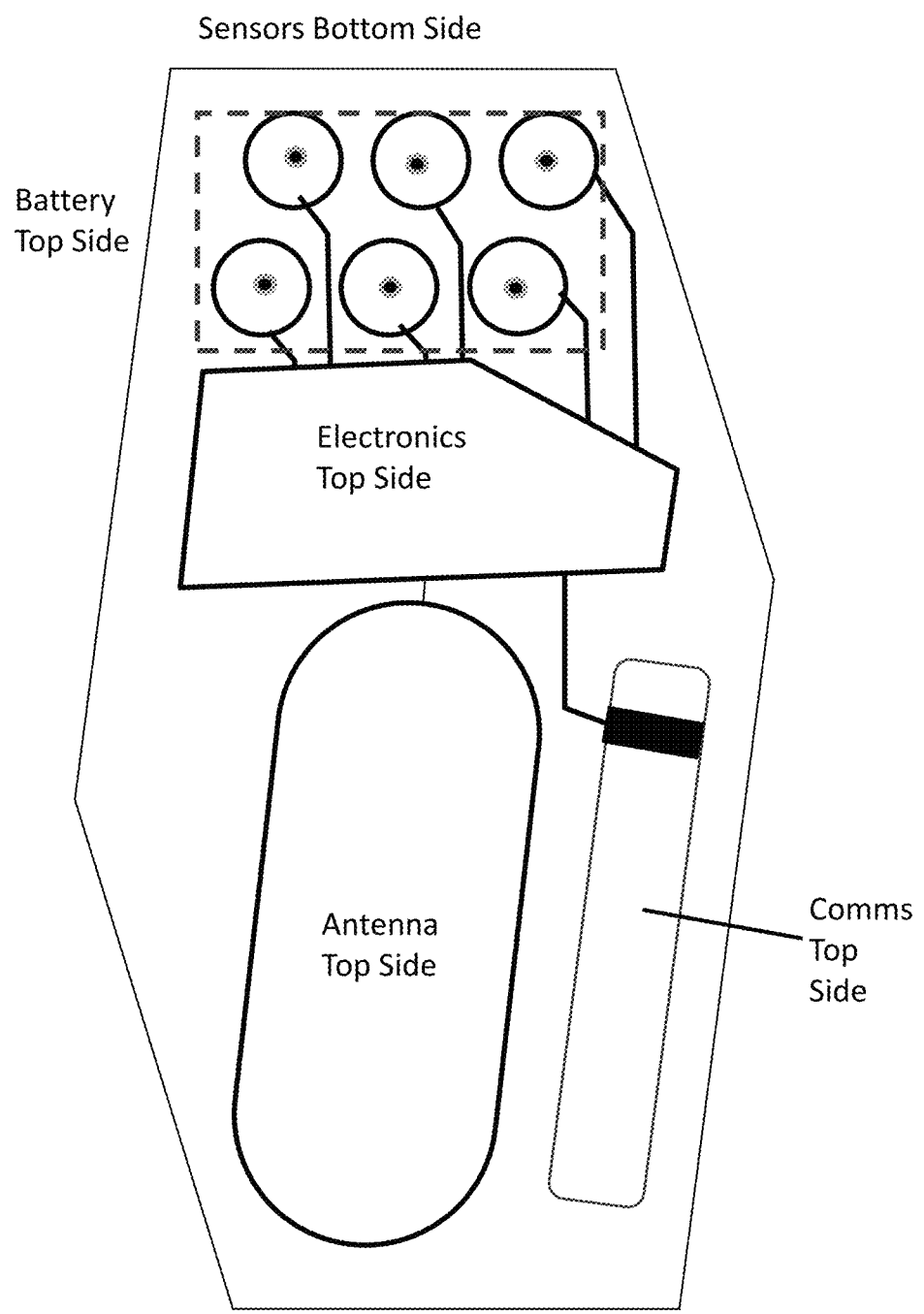
FIG. 4 shows a perspective top view of a flexible electronic layer on the bottom adhesive layer.
Figure 5:
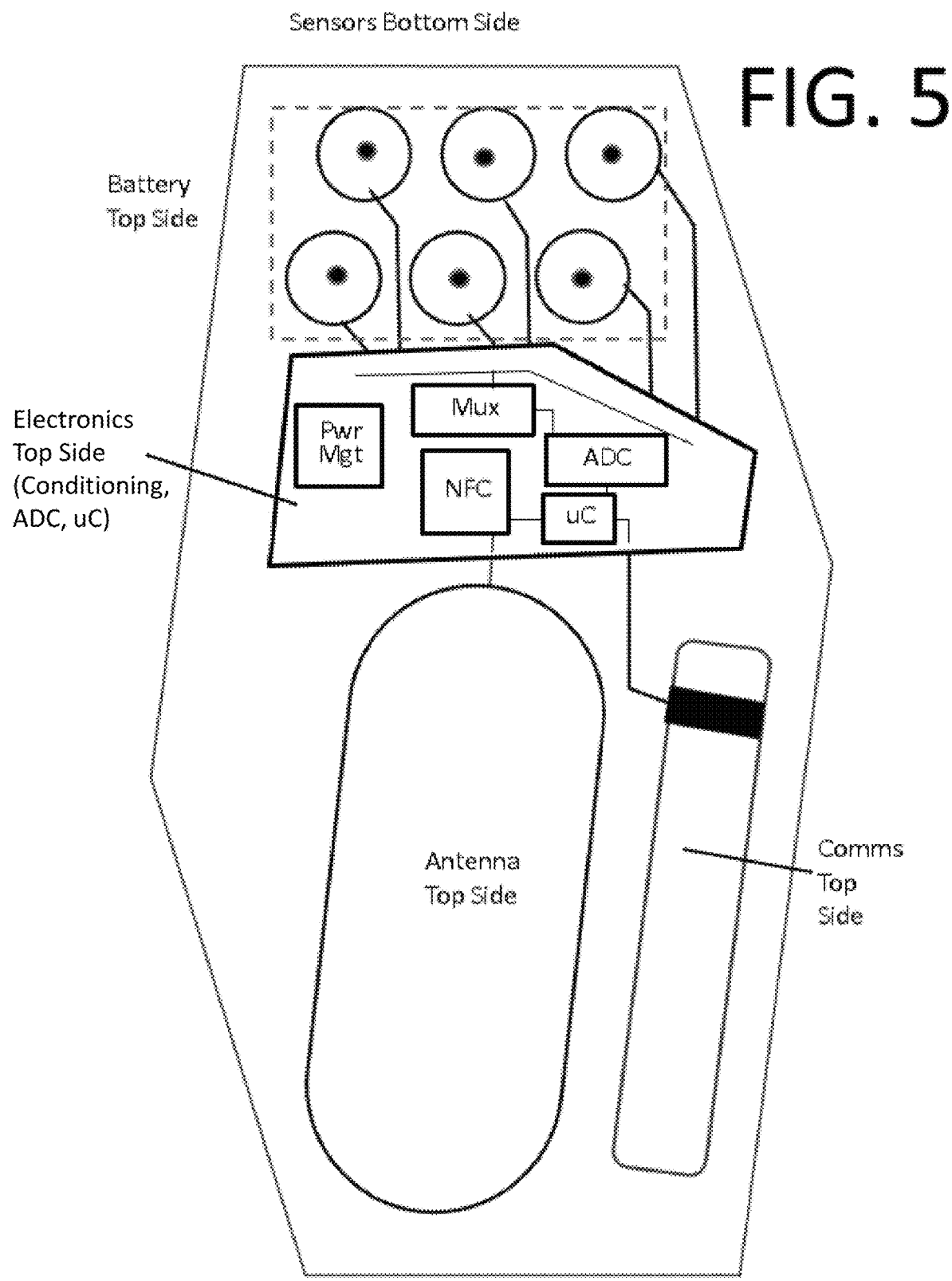
FIG. 5 shows a complete flexible electronic layer.
Figure 6:
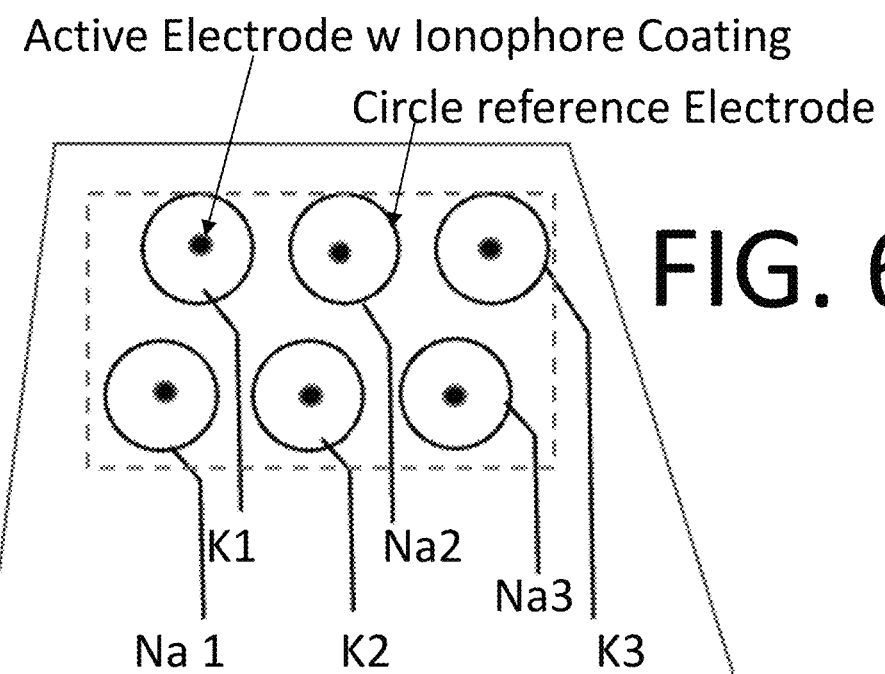
FIG. 6 shows a separated layer of electrochemical sensors.
Figure 8:
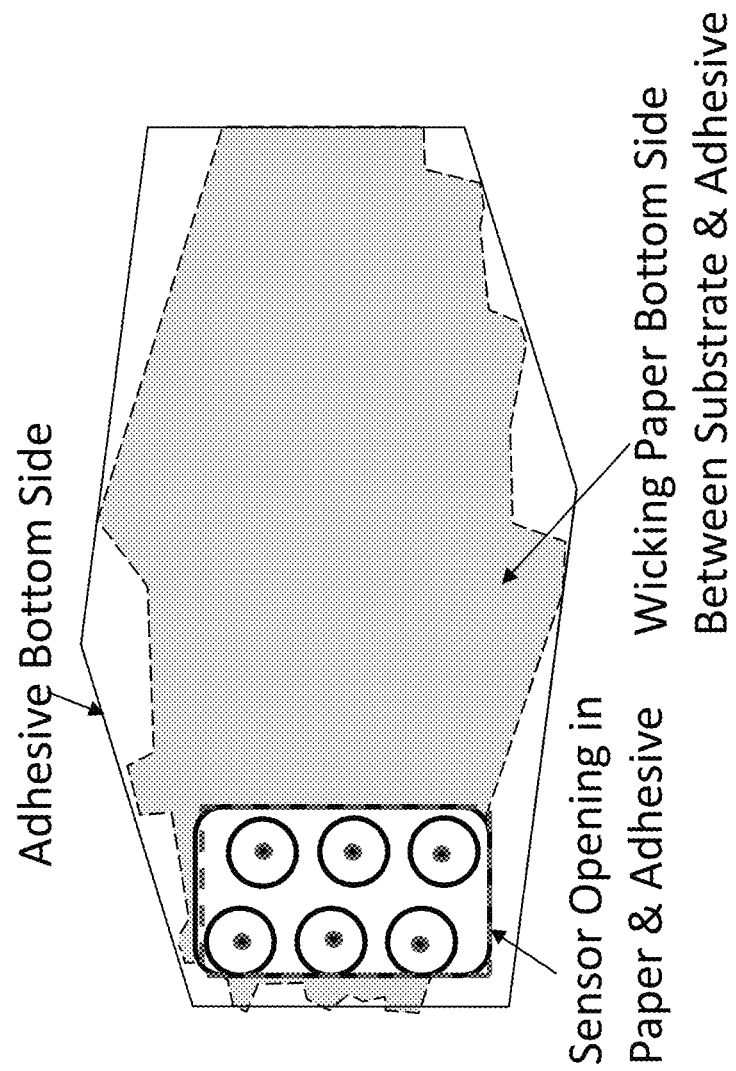
FIG. 8 shows a top perspective view (top) and bottom perspective (bottom) view of a complete sensor apparatus.

FIG. 3 illustrates a multi-layered apparatus or device that includes a double-sided adhesive layer, a filter paper, an electronic layer, and a woven top adhesive. More specifically, the device is flexible and multi-layered, wherein the layers comprise the following: a macrofluidic, double-sided adhesive layer; an electronic layer comprising at least one electrochemical sensor, a microcontroller, and a transceiver antenna coil; a microfluidic management layer; and a vapor porous, top protective layer. The macrofluidic, double-sided adhesive layer is intimately adhered to the skin. The electronic layer is intimately adhered to the microfluidic, double-sided adhesive layer, as shown in FIG. 4. The microfluidic management layer circumferentially surrounds the at least one electrochemical sensor of the electronic layer. The vapor porous, top protective layer is placed on and completely covers the microfluidic management layer and electronic layer. The vapor-porous, top protective layer is intimately adhered to the macrofluidic, double-sided adhesive layer. The fully fabricated sensor apparatus is shown in FIG. 8. Preferably, the length of the apparatus is approximately 76.1 mm. In one embodiment, the adhesive of the apparatus is Double Coated Polyester Nonwoven Tape (commercially available as 3M 9917 as of this writing). In another embodiment, the adhesive of the apparatus is Tan Tricot Knit Tape (commercially available as 3M 9926T as of this writing). The design of the microfluidic layer improves flow control and decreases patch layer delamination during high sweat volume use cases.

Figure 34:
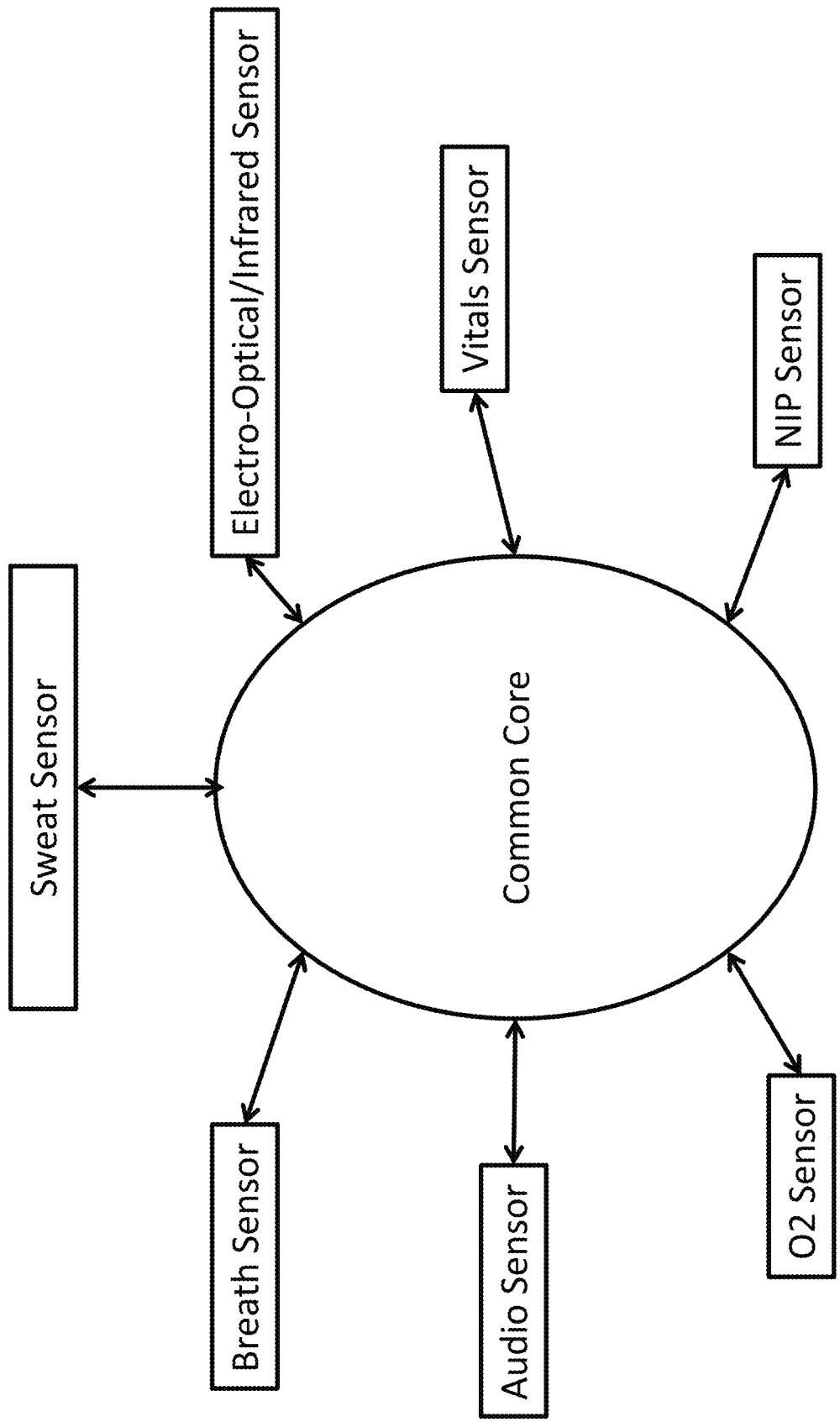
FIG. 34 shows a diagram of a suite of sensors in addition to a sweat sensor.

FIG. 34 shows a diagram illustrating a suite of sensors in addition to a sweat sensor, including a non-invasive penetration (NIP) sensor, an audio sensor, a vitals sensor, an electro-optical/infrared sensor, an oxygen sensor, a breath sensor, and a sweat sensor. In one embodiment the sensor includes at least two of the sensors in FIG. 34. In another embodiment, one of the suite of sensors is the only sensor utilized. One or more of the sensors is embedded in the skin in one embodiment of the present invention. An embedded sensor preferably mimics the composition and behavior of cells. The electro-optical/infrared sensor may include a fluorescent signal sensor. In one embodiment, a reader sends an excitation light through the skin to the biosensor, which then emits a fluorescent light proportional to the amount of biochemical measured.

Figure 35:
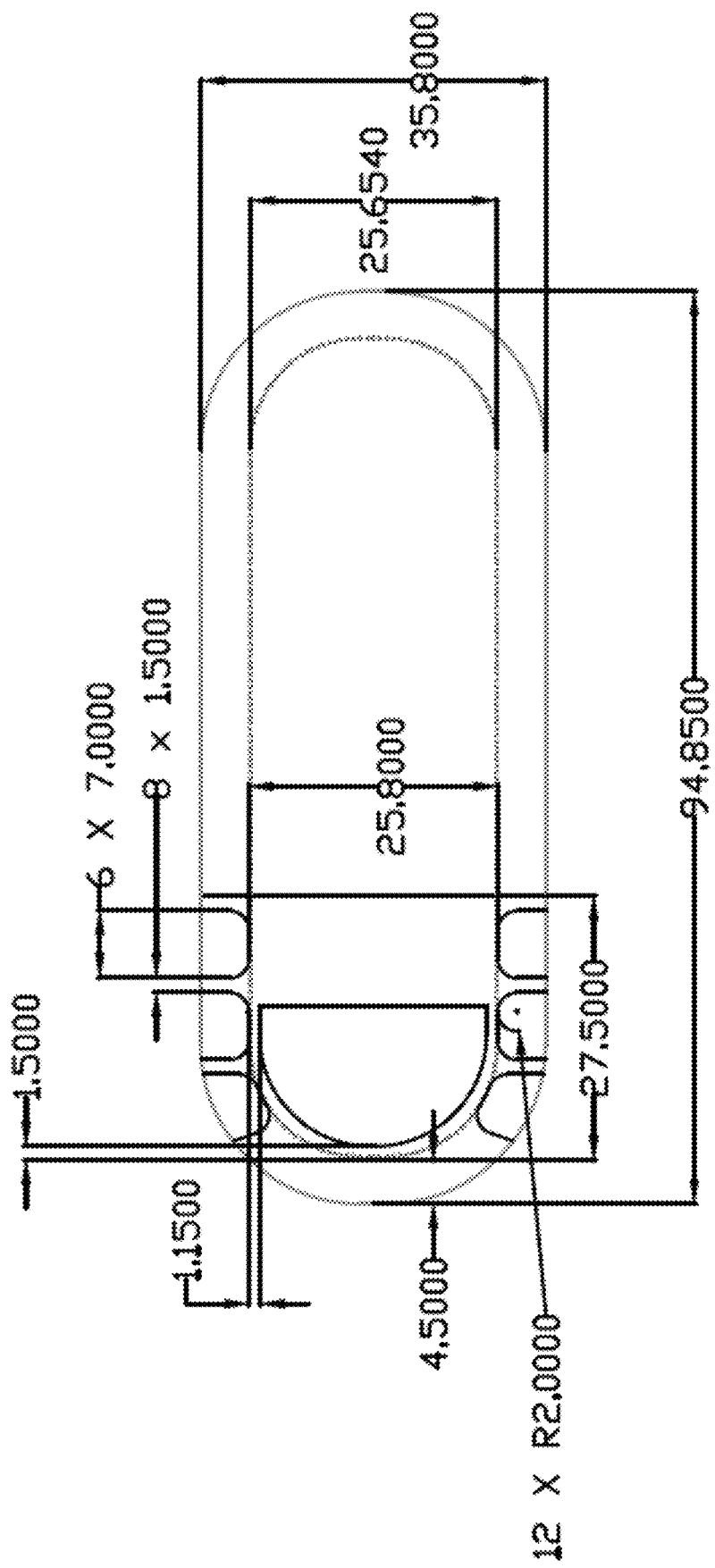
FIG. 35 shows a top perspective view of one embodiment of the sensor apparatus.

FIG. 35 shows a top perspective view of one embodiment of the sensor apparatus. The flex circuit is substantially centrally located on the bandage material and adhesive. Wicking paper is utilized to move bodily fluid, particularly sweat, through the sensor apparatus. The reverse "D" shaped hole is through the adhesive and the wicking paper. All dimensions in FIG. 35 are in MM or VOS, as appropriate.

Figure 36:
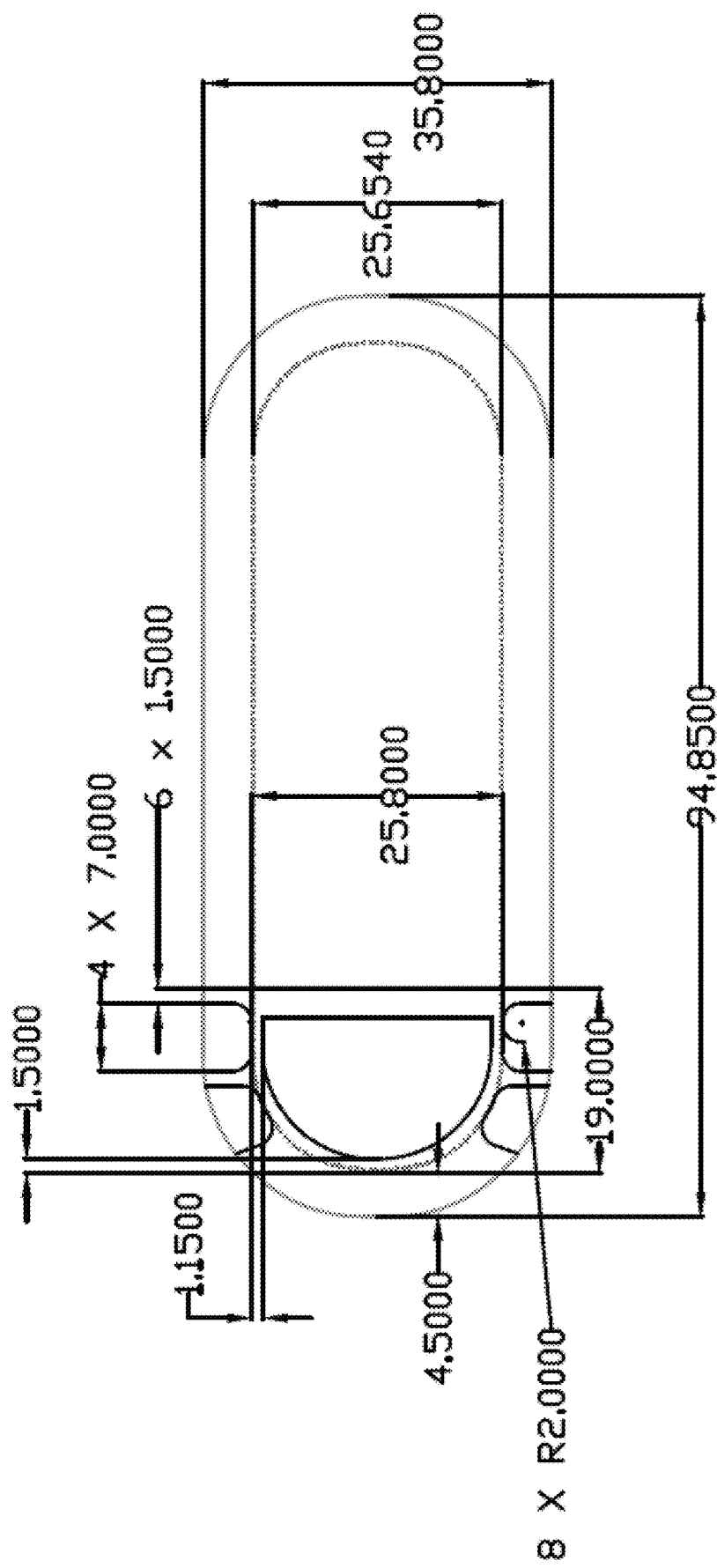
FIG. 36 shows a top perspective view of another embodiment of the sensor apparatus.

FIG. 36 shows a top perspective view of another embodiment of the sensor apparatus. The flex circuit is substantially centrally located on the bandage material and adhesive. Wicking paper is utilized to move bodily fluid, particularly sweat, through the sensor apparatus. The reverse "D" shaped hole is through the adhesive and the wicking paper. All dimensions in FIG. 36 are in MINI or VOS, as appropriate.

Figure 9:
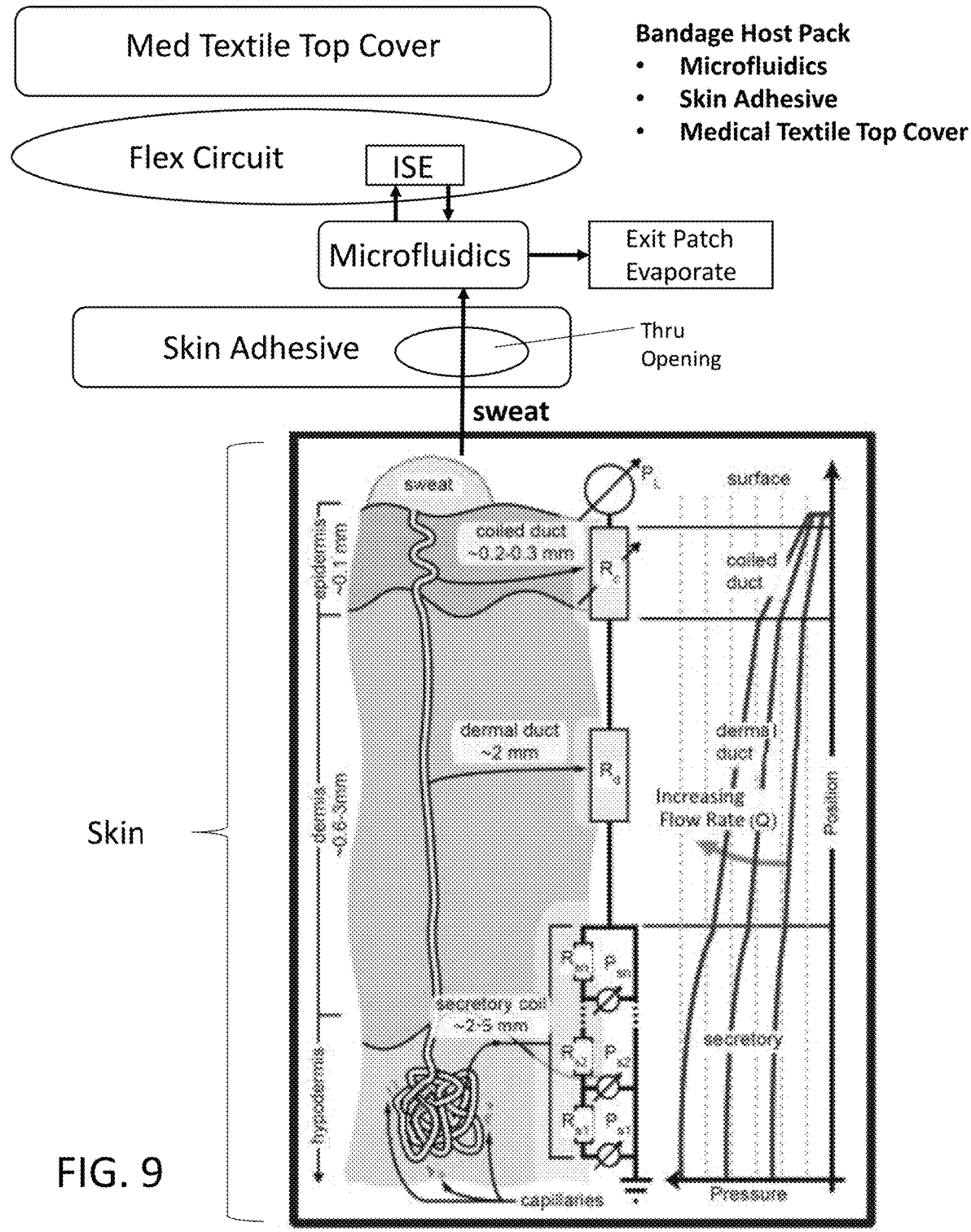
FIG. 9 shows a diagram of the sweat path through the sensor apparatus.

The sensor apparatus is designed to allow sweat to flow through laser cut, macrofluidic pores in the skin adhesive layer, as shown in FIG. 9. Sweat then flows through a filter to the electronics layer, specifically the electrochemical sensor unit, where biomarkers may contact the electrodes of the electrochemical sensor unit. The sweat evaporates through the woven textile protective top layer. The evaporation affords improved and continuous sweat flow into the sensor apparatus. This wicking ensures sweat sensing measures are consistently using new sweat samples rather than static or diluted samples. In one embodiment, the wicking and sweat flow rates range from 0% to 5% of Total Body Loss/hr (instant equivalent sweat loss rate) or equivalent to 11.5 L/hr total loss.

The present invention further includes a device with a small amount of ionophore polymer on the active electrodes to filter/prevent untargeted ions to reach the electrode. Sensor functionality and accuracy require precision placement with proper thickness of a small amount of ionophore polymer in one embodiment. The precision placement is conducted either manually or via automated equipment. The amount of ionophore polymer is approximately 2 microliters with a designated viscosity placed in a clean assembly environment to completely cover the exposed active electrode on the skin-facing side of the flexcircuit. The coating shall preferably not exceed more than 0.5 mm from the edge of the electrode. In one embodiment, the ionophore polymer is cured. In another embodiment, the curing takes place using heat and/or light to accelerate drying without changing the ionophore selectivity characteristics.

In one embodiment, the sensor is calibrated. Preferably, a human user calibrates the sensor using actual test results and feedback from the sensor. Advantageously, human user calibration or human use self-calibration (H-SCAL) provides for more accurate data when compared with calibration of sensors solely in the laboratory. Actual human test data is compared to external sweat loss values obtained from highly accurate scales. The external data is utilized to adjust several factors for a human user. Specifically, the adjustments provide for correction of a collection of diminutive and/or major error sources to improve the overall accuracy of the system.

Figure 11B:
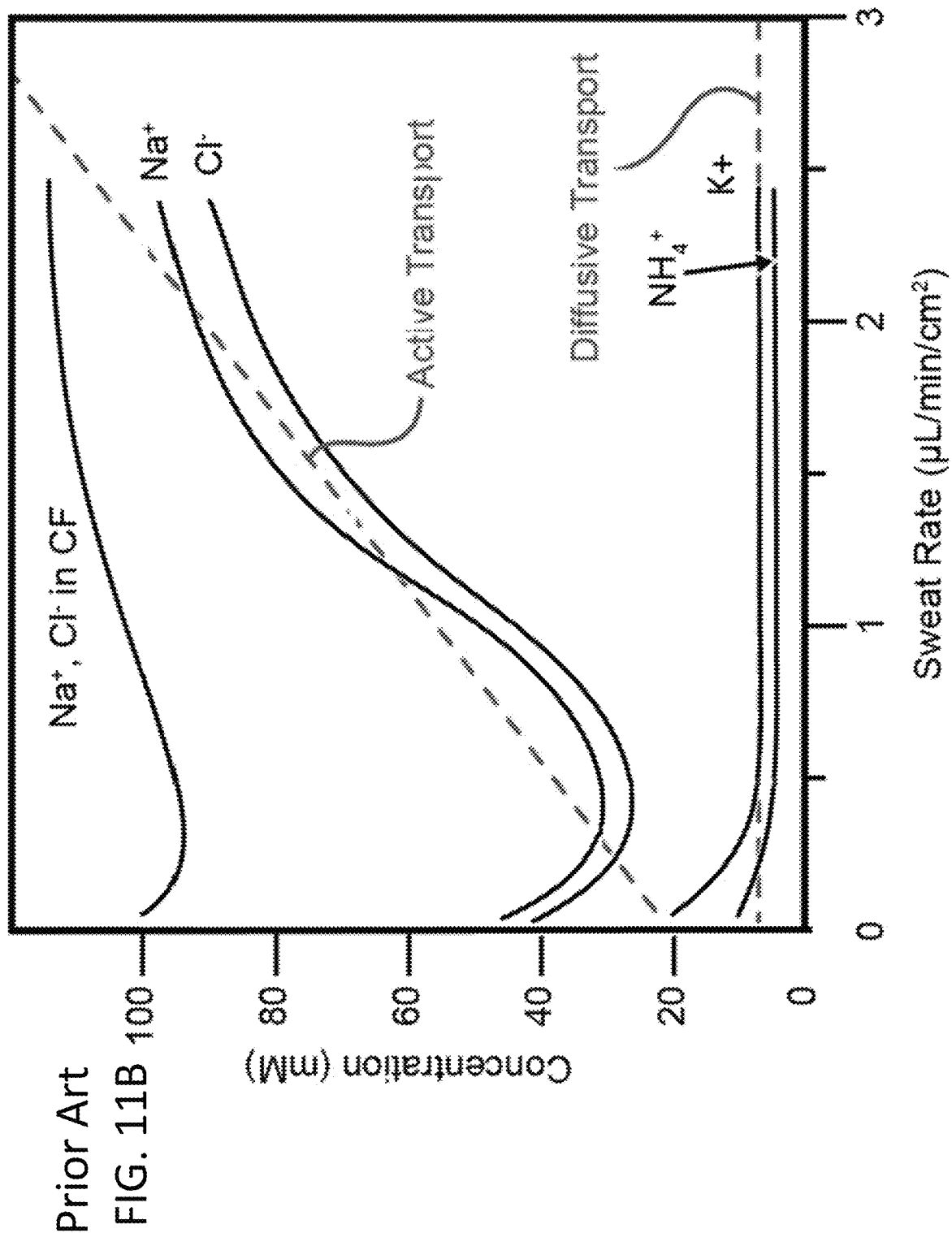
FIG. 11B shows a chart of concentration of ions vs. sweat rate.

FIG. 11F details one embodiment of the H-SCAL wherein the apparatus is calibrated using a personalization factor (Fp). The default value of the personalization factor is 1. At least one remote transceiver device calculates the personalization factor using at least a weight of the user before physical activity and a weight of the user after physical activity. In a preferred embodiment, the weight of the user before physical activity and the weight of the user after physical activity are manually entered into the remote transceiver device. In an alternative embodiment, the weight of the user before physical activity and the weight of the user after physical activity are automatically uploaded by a smart scale and/or a third party application. The at least one remote transceiver device transmits the personalization factor to at least one remote computer server or at least one remote computing device or database for storage. The personalization factor is updated when a new weight of the user before physical activity and a new weight of the user after physical activity are provided. In one embodiment, the personalization factor is further based on a maximum rate of oxygen consumption for the human ($VO_2$ max), fitness or conditioning level, a body mass factor, outdoor temperature, humidity, and/or estimated body surface area. In one embodiment, the personalization factor is used to adjust the values of Fcondition and/or SFR. In an alternative embodiment, the value of Fcondition varies depending on the value of $VO_2$ max. The personalization factor corrects for normal variations in a human from time to time, and also normalizes minor variations due to manufacturing, storage, wetting, and handling.

Figure 7:
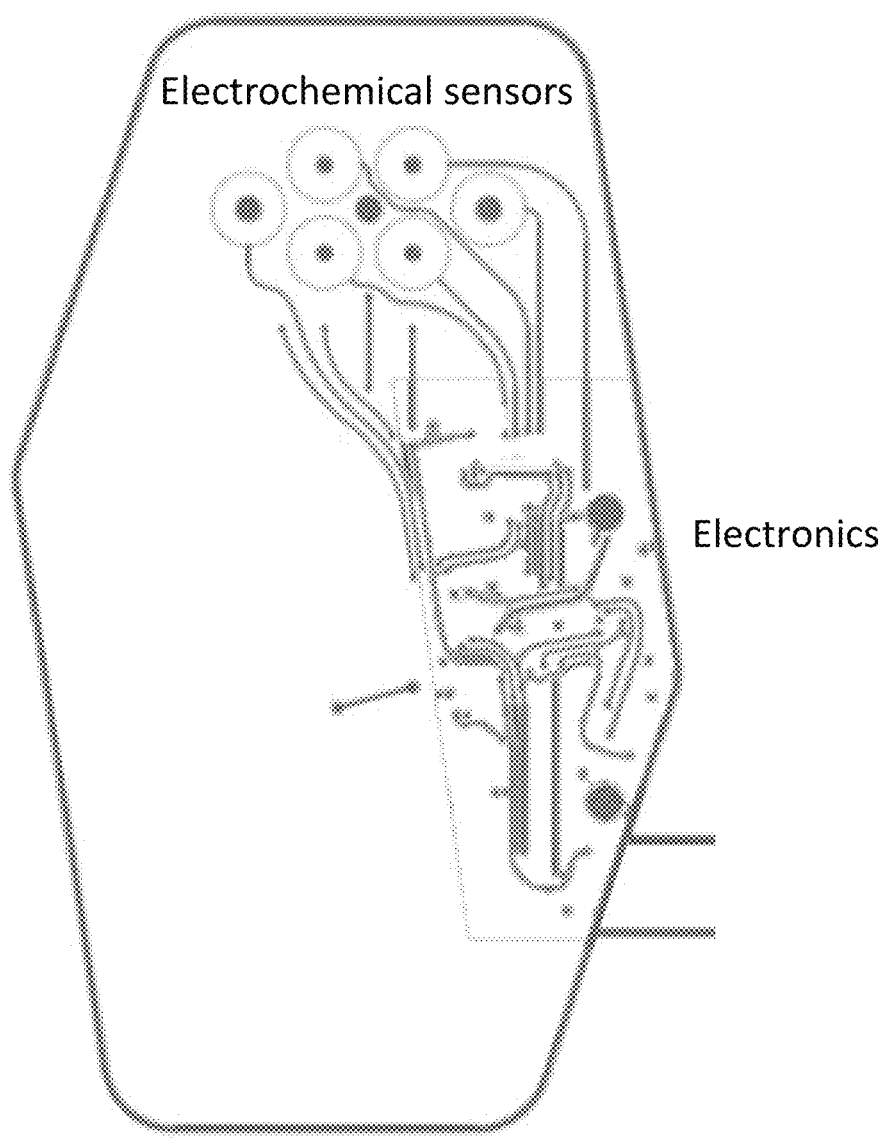
FIG. 7 shows the electrochemical sensors.
Figure 15:
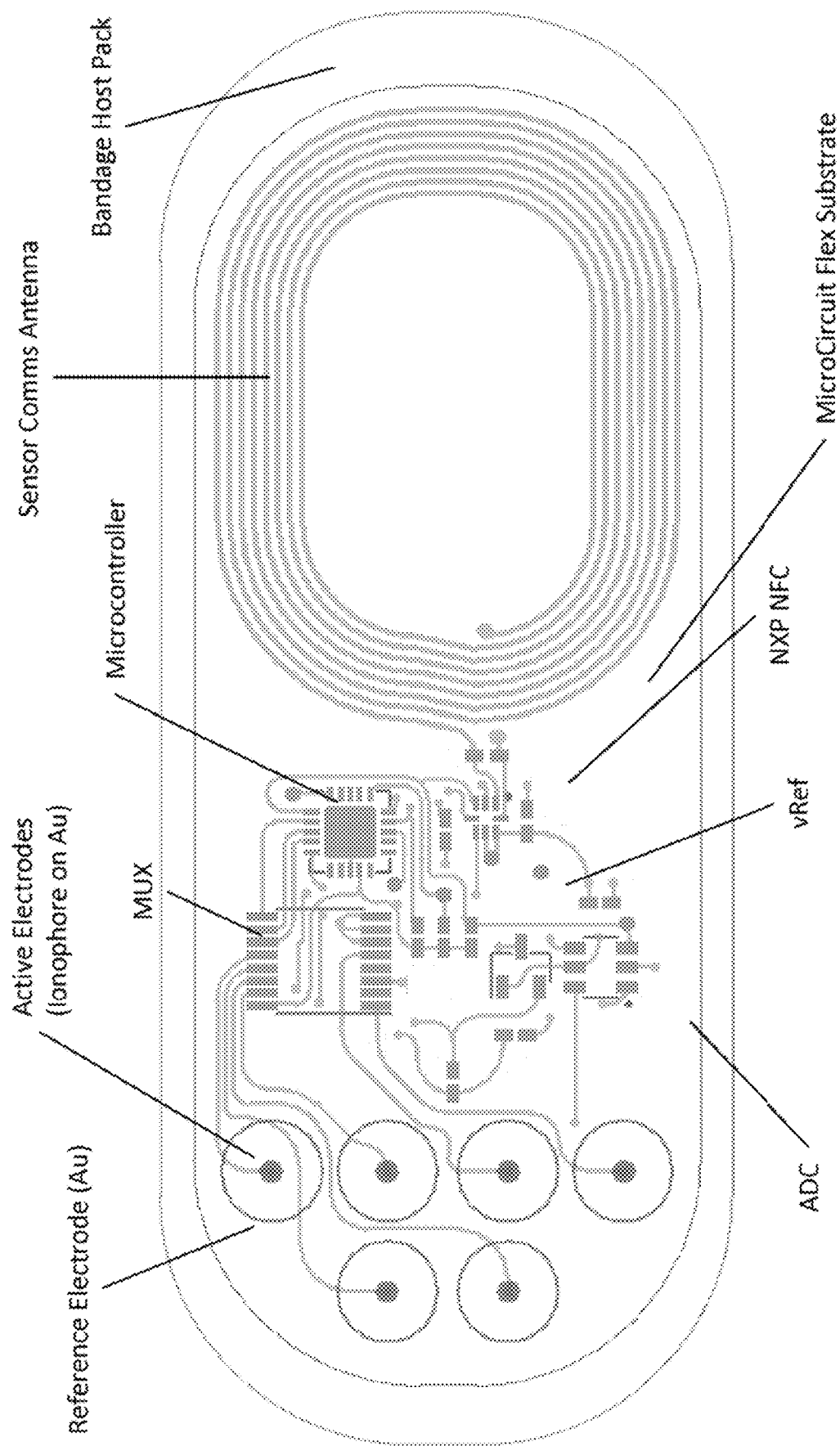
FIG. 15 shows a diagram of components within the sweat sensor subsystem.

The sensor apparatus includes sweat sensor subsystem, as shown in FIG. 15, which includes a microcontroller that receives multiple input data, which are input from multiple sources. A first source is biological fluid, preferably sweat, although alternative fluids may be used. The sweat contains a variety of analytes, such as, by way of example and not limitation, electrolytes, small molecules (molecular weight <900 Daltons), proteins, and metabolites. Exemplary analytes include substances including sodium or potassium. The article The microfluidics of the eccrine sweat gland, including biomarker partitioning, transport, and biosensing implications, by Sonner, et al. in Biomicrofluidics 2015 May; 9(3); 031301, which is incorporated by reference herein in its entirety, reports microfluidic models for eccrine sweat generation and flow and reviews blood-to-sweat biomarker partition pathways. In one embodiment, the sensor apparatus is operable to sense sodium and chloride both in a dynamic range from about 0 mM to about 120 mM, with normal ranges in humans being about 20 mM to about 100 mM. In another embodiment, the sensor apparatus is operable to sense potassium in a dynamic range from about 0 mM to about 40 mM, with normal ranges in humans being about 5 mM to about 20 mM. In one embodiment, the sensor has a response time of about 60 seconds with about a 90% response. Other analytes include oxygen, glucose, calcium, ammonium, copper, magnesium, iron, zinc, lactate, creatinine, uric acid, urea, ethanol, amino acids, hormones, steroids, proteins, catecholamines, and interleukins. In one embodiment, the sensor is operable to analyze the analytes at a pM level, preferably in the 1-10 pM range or even below 1 pM (the sub-pM level). These analytes are collected at the electrochemical sensor, as shown in FIG. 7, which houses reference (preferably standard) and active electrodes, wherein, by example and not limitation, the electrodes are silver, zinc, copper, gold, platinum, rhodium, carbon or a combination thereof. In one embodiment, the apparatus has an embedded dot-circle configuration for a reference electrode to improve stability through less interference. Additionally, gold probes or electrodes are used in one embodiment to improve stability and reduce production costs. The apparatus also includes a microprocessor, multiplexer (mux), ADC, and optimized on board processing for real time, pre-transmission sensor signal conditioning in another embodiment.

Figure 40:
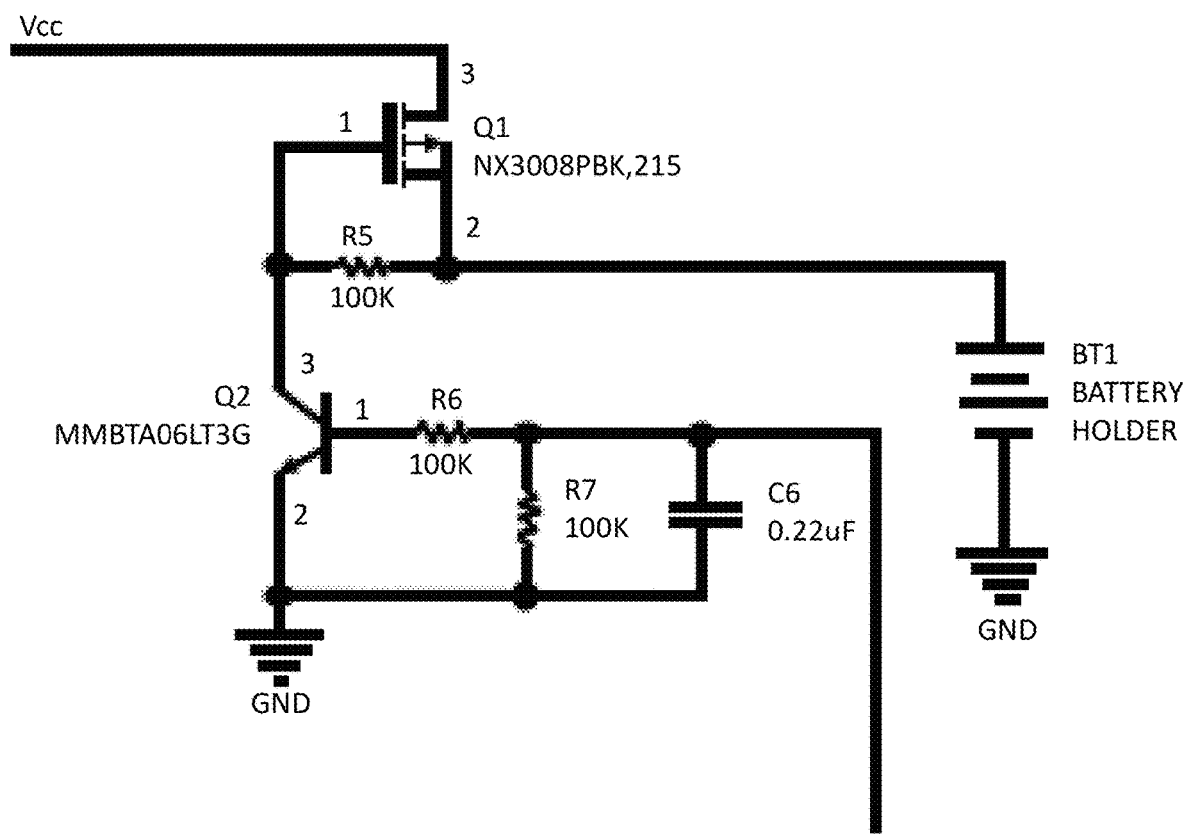
FIG. 40 shows a battery latch mitigation capacitor placement.

Unique human induced electromagnetic interference (H-EMI) sometimes cause interference and produce inaccurate measurements from the sensor apparatus. Specifically, human induced anomalies affect flex circuit functionality, performance, and reliability. Variations in the location of the sensor on the human body as well as human skin variations between people can cause unpredictable flex circuit behavior that is not readily apparent in lab settings. Through testing on humans, various embodiments and solutions to H-EMI have been developed. In one embodiment, hardware components are placed to mitigate the human use electromagnetic interference effects on flex circuits. Specifically, the placement of capacitors compensates for intermittent power variations. Additionally, strategically placed Kapton reinforcements (or other polyimide components) further mitigate EMI disturbances resulting from human use electromagnetic interference. Specifically, capacitors are utilized on power/battery latching circuits to mitigate human motion artifacts impacting measurement cycles. FIG. 40 shows a battery latch mitigation capacitor placement. The values included in FIG. 40 are for purposes of illustration by example and in no way limit the values which are utilized in the present invention.

Figure 41:
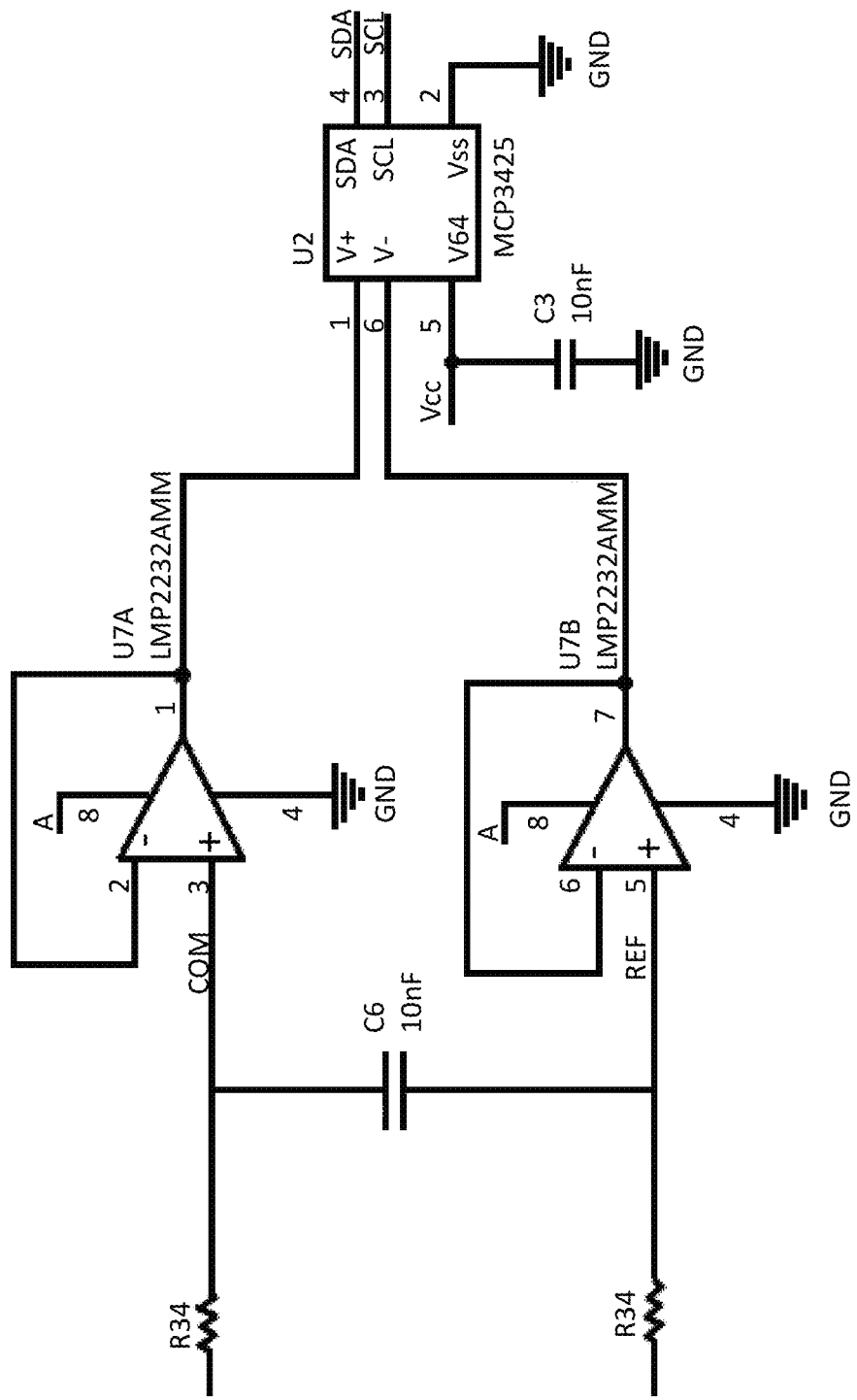
FIG. 41 shows an RC configuration with ground reference.
Figure 42:
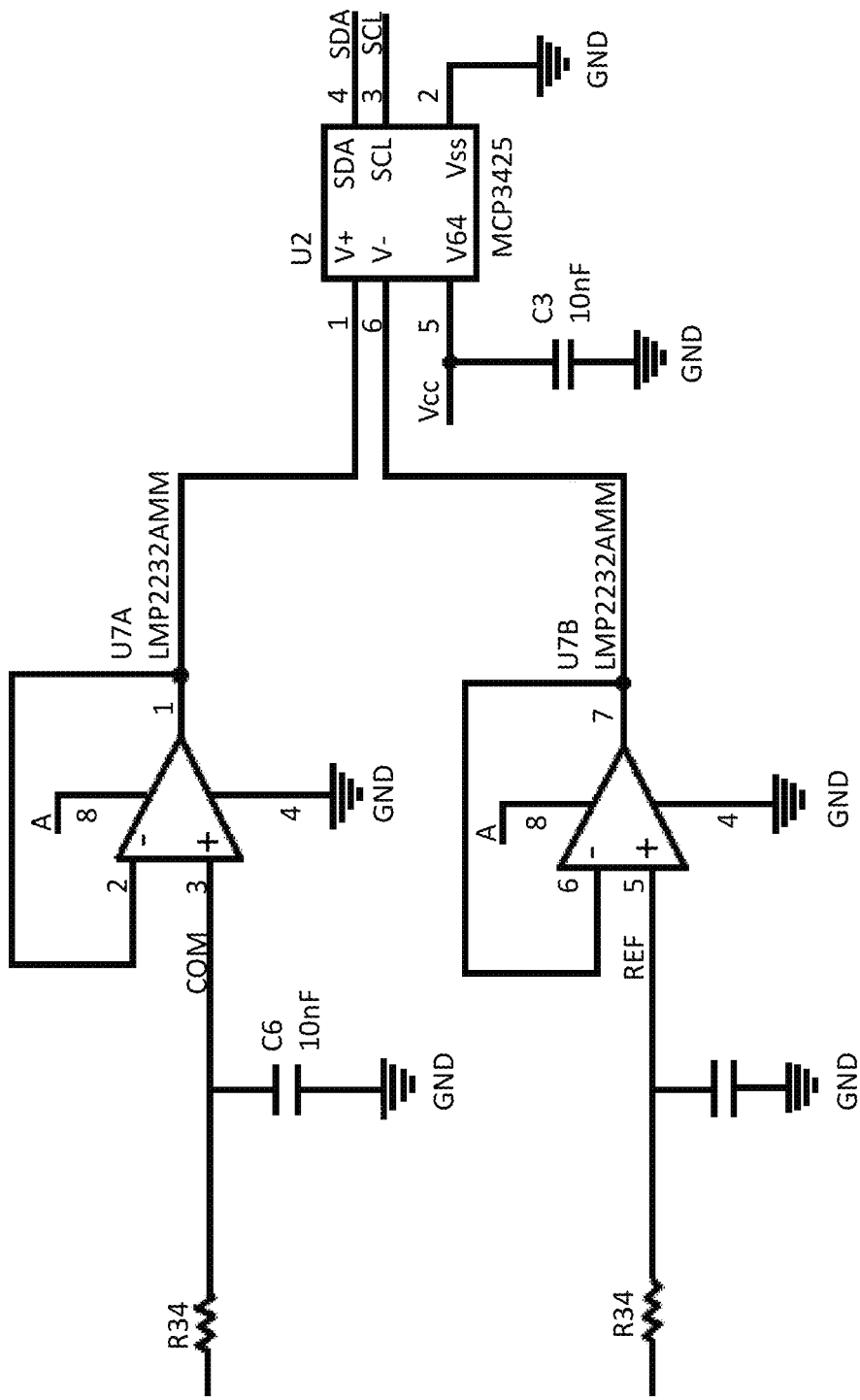
FIG. 42 shows an RC configuration with differential measurement.
Figure 43:
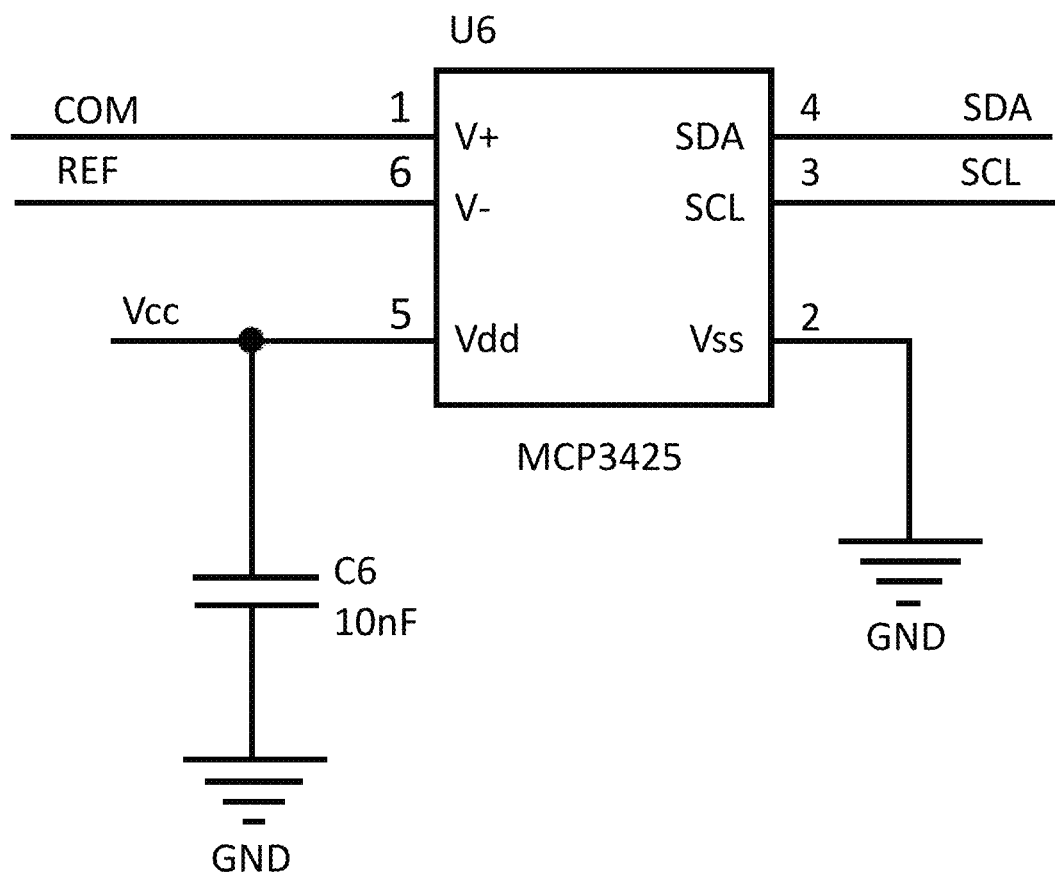
FIG. 43 shows an example of cap placement Vcc to Ground for supply voltage stability and/or noise immunity.

Adjustments in firmware running on a microcontroller also offset EMI in some embodiments. In another embodiment, adjustments to filtering (preferably by adding specific RLC components) and noise suppression offset EMI. Improved measurement electronics input design and sampling methods also mitigate H-EMI. In one embodiment, input design involves complex impedance related to the RLC (mostly R and C) components to condition sensor inputs to overcome motion artifacts manifest from the human sensor interface and input buffering methods to reduce measurement electronics impact on sensor measurements (Heisenberg Uncertainty). FIG. 41 shows an RC configuration with ground reference. FIG. 42 shows an RC configuration with differential measurement. FIG. 43 shows an example of cap placement Vcc to Ground for supply voltage stability and/or noise immunity. Firmware branching logic preferably differentiates between power on cycle and motion induced power variations.

The present invention also includes sensor embodiments which are operable under the most demanding physical environments, and in particular, athletic use cases. Specifically, a durable sensor is needed for these cases because of exposure to violent impact shock, speed changes, motion intensity, exposure to water, etc. Strengthening the flex circuit and electronic layouts minimize use case impacts on the sensor. Additionally, advanced flex circuit protection minimizes impacts upon the sensor. Advanced flex circuit protection includes strategic flex circuit mix with rigid boards and/or application-specific integrated circuit (ASIC) miniaturization. Advanced rubberized casings and microfluidics based on crystal fiber technology are also utilized in one embodiment. Specifically, the present invention includes the aforementioned adjustments to the sensor head of the sensor apparatus. Sensor heads accommodate a variety of motion factors, including flex, stretch, sliding, and shock loading. In one embodiment, the present invention utilizes multiple sensor configurations to accommodate individual sensor disruption and/or failure.

In one embodiment, the sensor head is detachable and reattachable. The sensor head is attached via z-axis tape or hot bar soldering in one embodiment. In another embodiment, there is a standardized interconnection. In yet another embodiment, the sensor head pinout is selectable from the multiplexer side. In one embodiment, uC and a RF antenna are integrated with fabric. In yet another embodiment, two part encryption is utilized. RFI and shielding as well as adding layers to the board to provide additional ground planes and/or metallized fabric in dressing are also utilized.

Additionally, flexibility in most components of the sensor apparatus is not desired. FR4 is utilized in a preferred embodiment. The sensor head is the only flexible portion of the sensor in one embodiment, as the sensor head requires flex and adhesion to the human. However, for embodiments in which flexibility is desired, a variety of flexible substrates are utilized.

Another embodiment of the present invention includes adding a layer or row of 0 ohm resistors on either side of the multiplexer. Additionally, buffer amps are utilized either before or after the multiplexer. In an alternative embodiment, higher impedance ADC is utilized. Fault detection and isolation is also used in the systems and methods of the present invention.

Figure 37A:
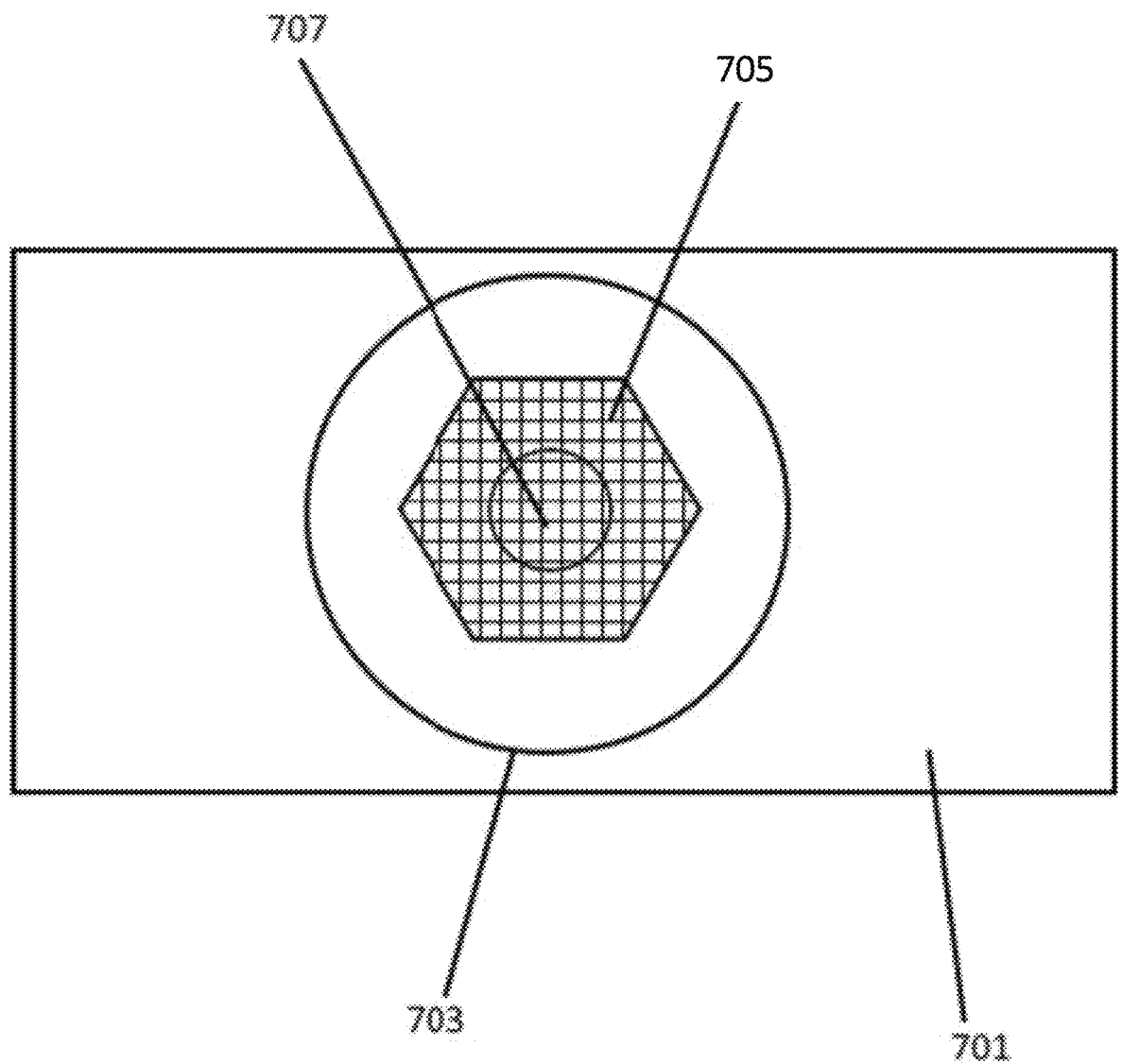
FIG. 37A shows a top perspective view of a sensor with a liquid ionophore coating.

FIG. 37A shows a top perspective view of a sensor with a liquid ionophore coating. A circuit board or other substrate 701 includes a copper trace or other conductive material/circuit element 703, an ionophore or any material applied using a liquid deposition method 705, and copper or other conductive material forming an active electrode 707. The ionophore 705 preferably covers the copper or other conductive material forming an active electrode 707.

Figure 37B:
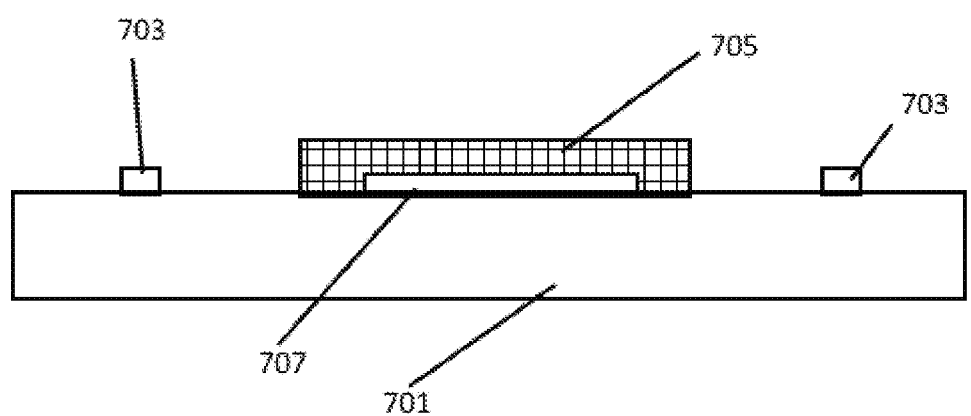
FIG. 37 B shows a side perspective view of a sensor with a liquid ionophore coating.
Figure 37C:
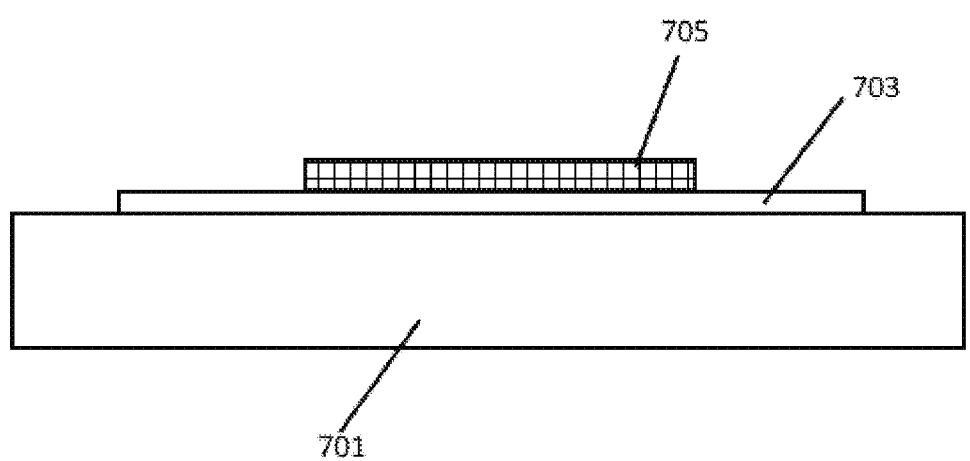

FIG. 37 B shows a side perspective view of a sensor with a liquid ionophore coating.

FIG. 37 C shows another side perspective view of a sensor with a liquid ionophore coating.

One sensor head embodiment of the present invention includes a Ring-Reference design. This design preferably solves issues with surface tension management.

Figure 39A:
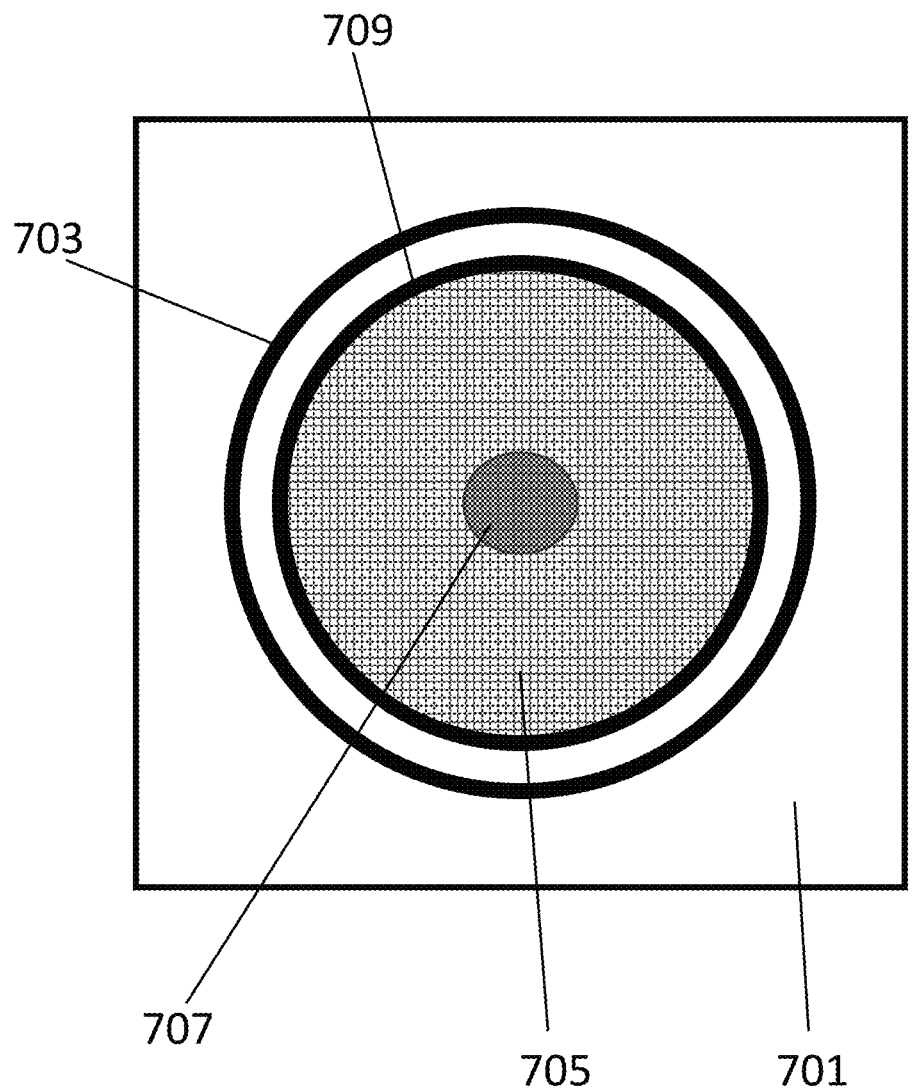
FIG. 39A shows a top perspective view of a sensor with a liquid ionophore coating which was formed using a surface tension dam approach.

FIG. 39A shows a top perspective view of a sensor with a liquid ionophore coating which was formed using a surface tension dam approach or Ring-Reference design. A circuit board or other substrate 701 includes a copper trace or other conductive material/circuit element 703, an ionophore or any material applied using a liquid deposition method 705, copper or other conductive material forming an active electrode 707, and a soldermask, printed ink, or any other non-conductive material dissimilar to the circuit board printed, deposited to, or otherwise adhered to the circuit board prior to liquid deposition 709. The ionophore 705 preferably covers the copper or other conductive material forming an active electrode 707.

Figure 39B:
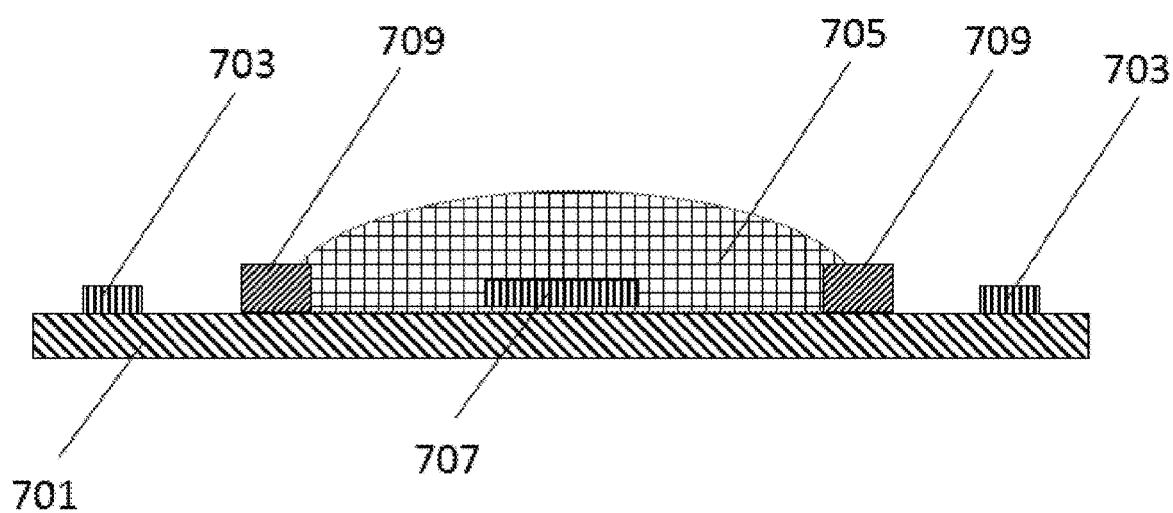
FIG. 39B shows a side perspective view of a sensor with a liquid ionophore coating which was formed using a surface tension dam approach.

FIG. 39B shows a side perspective view of a sensor with a liquid ionophore coating which was formed using a surface tension dam approach or Ring-Reference design.

In another embodiment, a surface tension management solution includes a printed or screened non-conductive ring inside a ring electrode to create a surface tension discontinuity. A soldermask preferably is a surface tension discontinuity in the surface tension management solution. In another embodiment, printed ink is a surface tension discontinuity in the surface tension management solution. Printed ink refers to any printed, screened, or deposited non-conductive material. This surface tension discontinuity supports the uniform deposition of liquid ionophores. In another embodiment, a well design is utilized for the sensor head for ionophore and electrode isolation. Specifically, the well design mitigates the stretch and/or sliding issues by increasing abrasion resistance.

Figure 38A:
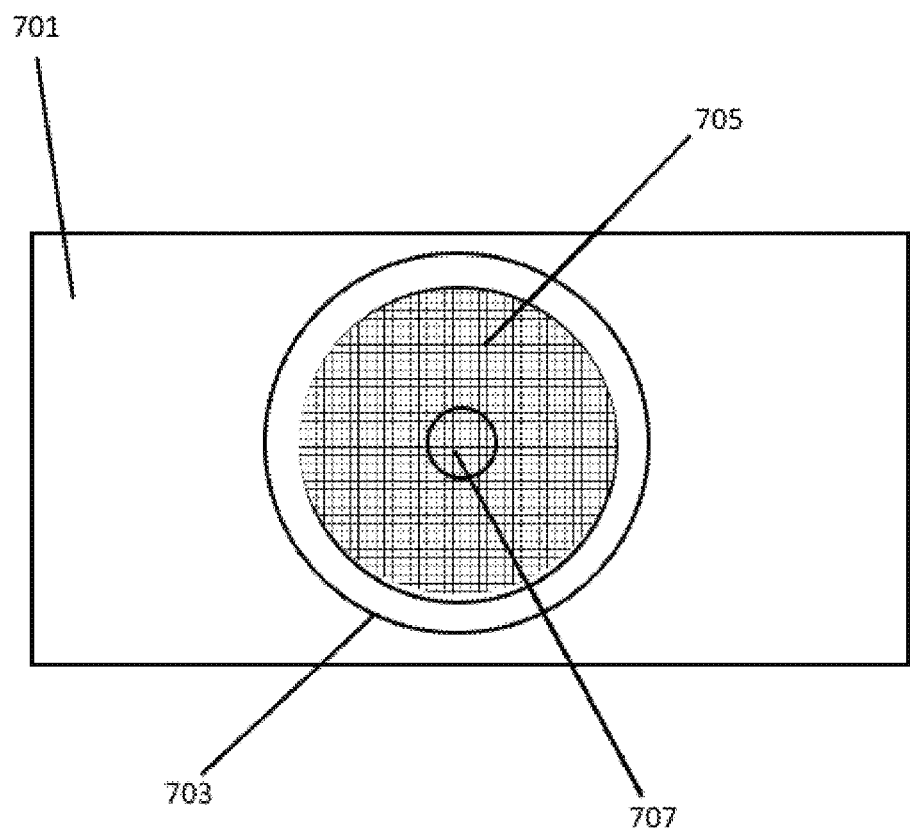
FIG. 38A shows a top perspective view of a sensor with a liquid ionophore coating which was formed using a well approach.

FIG. 38A shows a top perspective view of a sensor with a liquid ionophore coating which was formed using a well approach. A circuit board or other substrate 701 includes a copper trace or other conductive material/circuit element 703, an ionophore or any material applied using a liquid deposition method 705, and copper or other conductive material forming an active electrode 707. The ionophore 705 preferably covers the copper or other conductive material forming the active electrode 707.

Figure 38B:
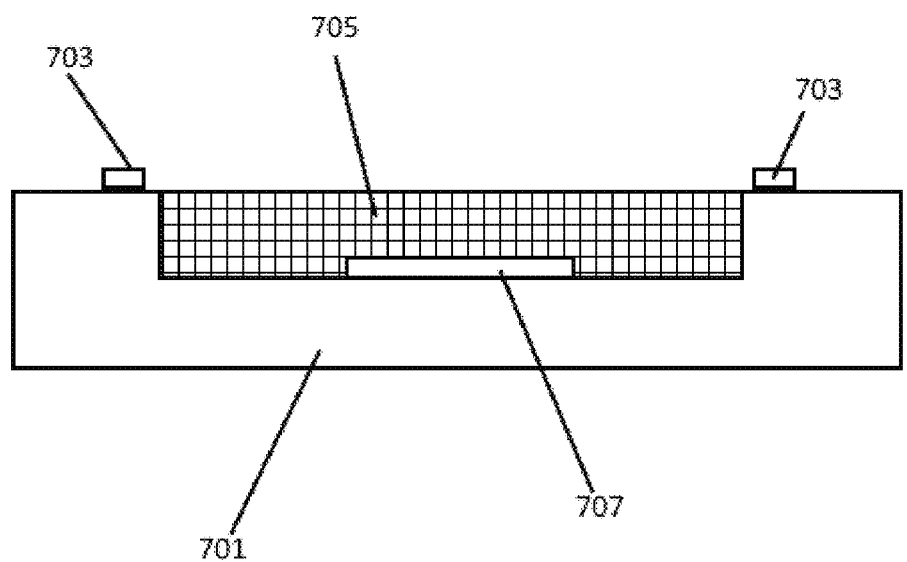
FIG. 38B shows a side perspective view of a sensor with a liquid ionophore coating which was formed using a well approach.

FIG. 38B shows a side perspective view of a sensor with a liquid ionophore coating which was formed using a well approach.

Figure 38C:
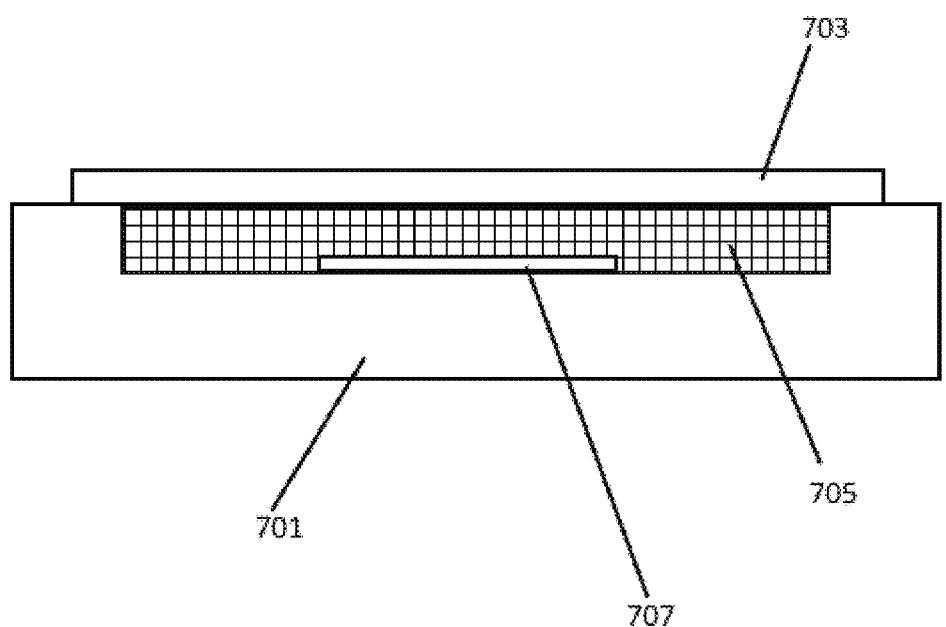
FIG. 38C shows another side perspective view of a sensor with a liquid ionophore coating which was formed using a well approach.

FIG. 38C shows another side perspective view of a sensor with a liquid ionophore coating which was formed using a well approach.

The Ring-Reference design or surface tension management solution and the well design are used to manage ionophore deposition, specifically liquid deposition on a surface. The liquid is preferably deposited on the surface of a circuit board and then solidifies and/or hardens.

Roll-to-roll manufacturing is an example of a manufacturing method that is efficient, cost effective, and allows for high production rates. Conventional processing (e.g., batch processing) is slower and higher cost due to the numerous steps involved. For example, liquid deposition of the ionophore is costly. Alternative methods, such as roll-to-roll manufacturing, may also improve the reliability of the system. However, roll-to-roll manufacturing requires a more durable ionophore polymer coating. One method of manufacturing ISEs with ionophore coverings that could be used with roll-to-roll manufacturing is to pre-fabricate the ionophore covering. In one embodiment, a pre-formed ionophore covering is adhered to the active electrode as an alternative to direct liquid deposition. In another embodiment, a durable ionophore layer is pre-fabricated and applied via a mechanical method. In yet another embodiment, a pre-formed ionophore covering is attached by an adhesive means (e.g., conductive adhesive) or thermal reflow.

A pre-formed ionophore covering can be created using a commercially available ion selective material dissolved in a polyvinyl chloride (PVC) solution. This requires a method of forming the pre-formed ionophore that increases the durability of the resulting 'plastic' ionophore covering. Various forming methods are employed to facilitate the placement of the ionophore covering on the active electrode. For example, the ionophore is cast in a shape and placed on a carrier or a film that facilitates mechanical placement via a pick-and-place or similar device manufacturing process. A cast shape requires a bounding form or structure that assures shape and handling consistency. This cast shape requires a means or method of adhesion applied locally to the active electrode without damaging or deforming the ionophore covering.

One such approach is to separate the active and reference electrodes onto different substrate layers ("a multilayer substrate approach"). The at least one reference electrode is on a first substrate layer that has voids or wells into which the ionophore is cast or formed and retained within the first substrate layer. The first substrate layer is then bonded in its entirety to a second substrate layer containing the at least one active electrode properly aligned with the wells containing the formed ionophore.

Figure 44A:
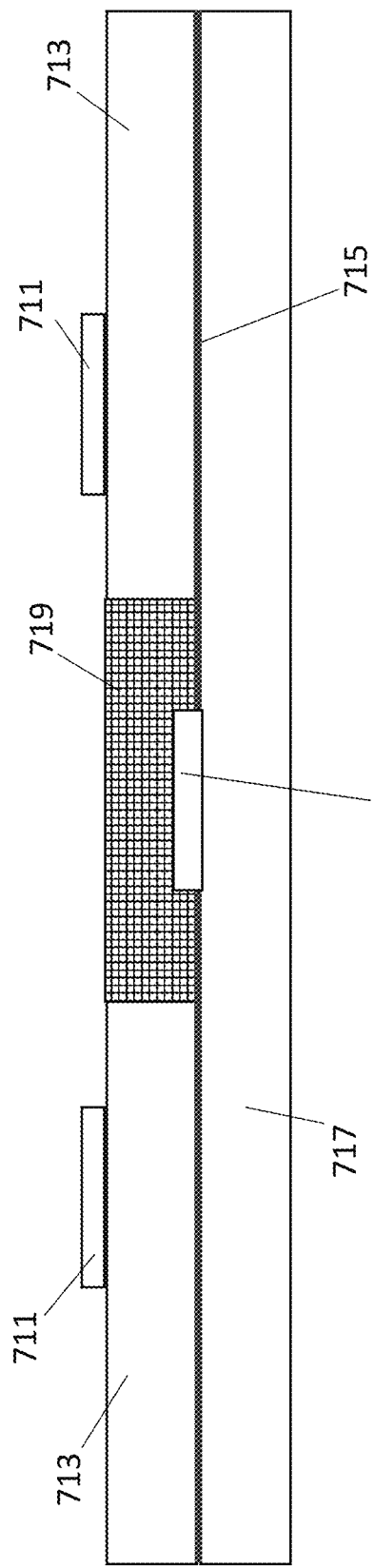
FIG. 44A shows a side perspective view of a sensor with a liquid ionophore coating which was formed using a multilayer substrate approach.

FIG. 44A shows a side perspective view of a sensor with a liquid ionophore coating which was formed using a multilayer substrate approach. A copper or other conductive material forms an active electrode 707. The active electrode is on top of an active electrode substrate 717. An adhesive or bonding film 715 is deposited on top of the active electrode substrate 717. Reference electrodes 711 are on top of a reference electrode substrate 713. An ionophore is cast in a well of the reference electrode substrate 713 to create a pre-formed ionophore 719. The reference electrode substrate 713 containing the pre-formed ionophore 719 is attached to the active electrode substrate 717 using the adhesive or bonding film 715. In a preferred embodiment, the adhesive or bonding film is a conductive adhesive and the reference electrode substrate and active electrode substrate are non-conductive. In a preferred embodiment, the copper or other conductive material is silver and the reference electrode substrate and active electrode substrate are comprised of polyester. The pre-formed ionophore requires thermal reflow because the active electrode is not covered with a conductive adhesive.

Figure 44B:
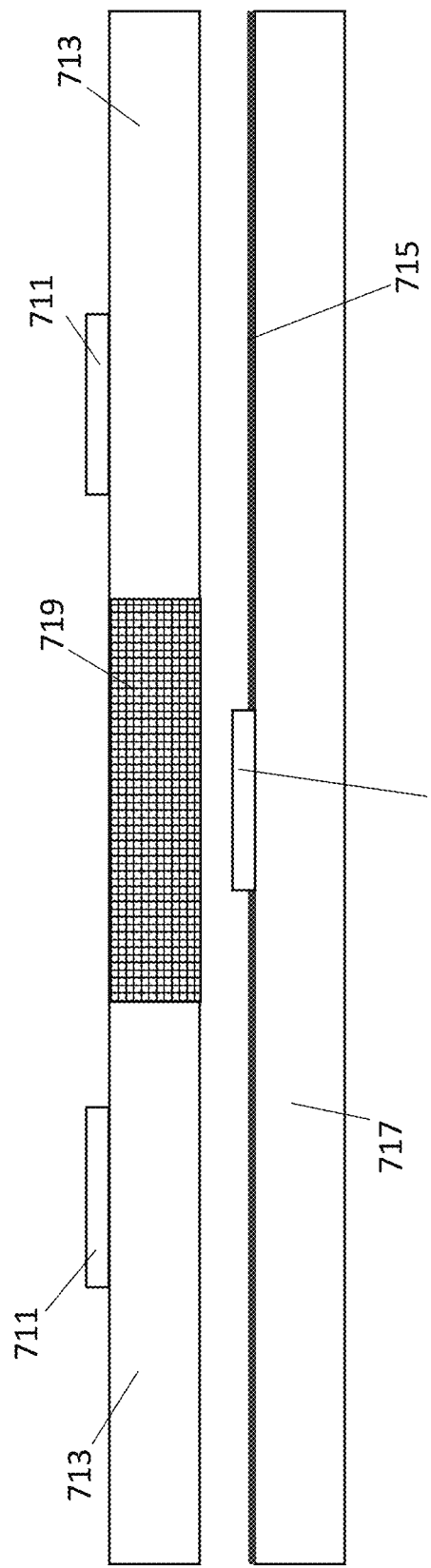
FIG. 44B shows an exploded side perspective view of the sensor of FIG. 44A.

FIG. 44B shows an exploded side perspective view of the sensor of FIG. 44A.

Figure 45A:
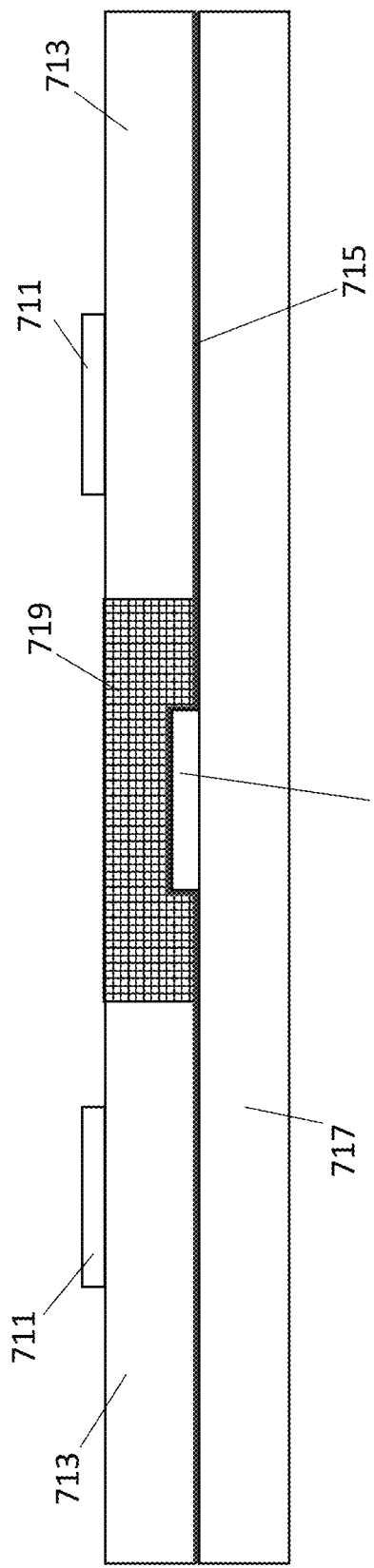
FIG. 45A shows a side perspective view of a sensor with a liquid ionophore coating which was formed using another multilayer substrate approach.

FIG. 45A shows a side perspective view of a sensor with a liquid ionophore coating which was formed using another multilayer substrate approach. A copper or other conductive material forms an active electrode 707. The active electrode is on top of an active electrode substrate 717. An adhesive or bonding film 715 is deposited on top of the active electrode substrate 717 and the active electrode 707. Reference electrodes 711 are on top of a reference electrode substrate 713. An ionophore is cast in a well of the reference electrode substrate 713 to create a pre-formed ionophore 719. The reference electrode substrate 713 containing the pre-formed ionophore 719 is attached to the active electrode substrate 717 using the adhesive or bonding film 715. In a preferred embodiment, the adhesive or bonding film is a conductive adhesive and the reference electrode substrate and active electrode substrate are non-conductive. In a preferred embodiment, the copper or other conductive material is silver and the reference electrode substrate and active electrode substrate are comprised of polyester. The pre-formed ionophore requires thermal reflow when the active electrode is not covered with a conductive adhesive.

Figure 45B:
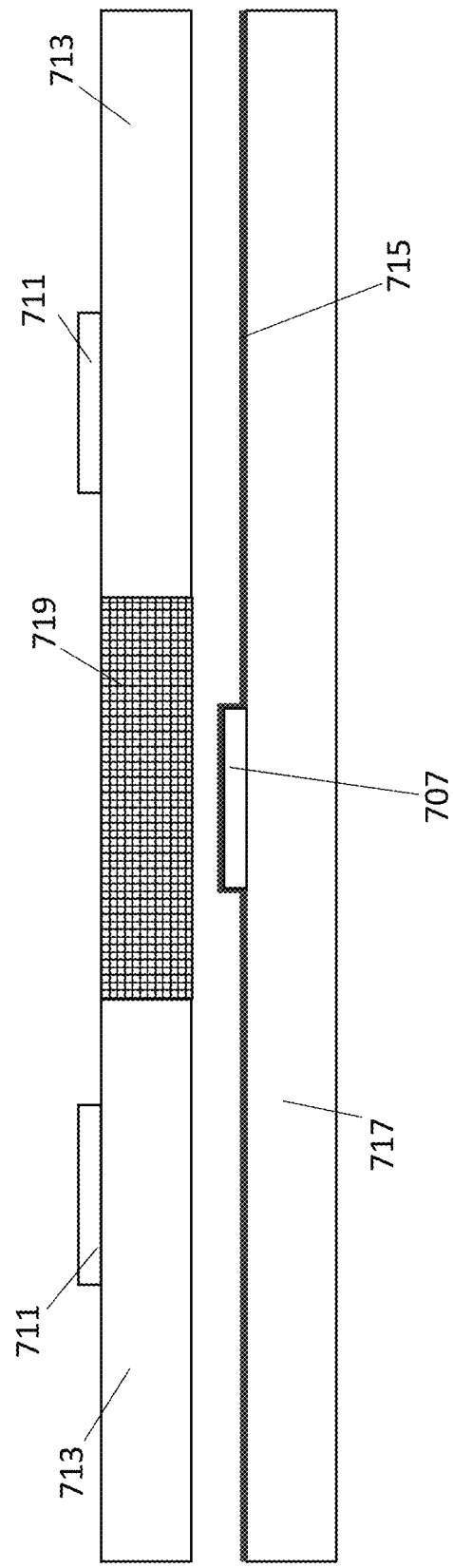
FIG. 45B shows an exploded side perspective view of the sensor of FIG. 45A.

FIG. 45B shows an exploded side perspective view of the sensor of FIG. 45A.

Alternatively, the ionophore covering is formed in a shape that can be handled or applied on a carrier or film that can be removed after application. In another embodiment, the ionophore covering is formed in a shape that can be handled or applied on a carrier or film that becomes an integral part of the sensor (e.g., a microfluidic absorption layer).

FIG. 46A shows a side perspective view of a sensor with an ionophore covering after a carrier or film is removed following application of a pre-formed ionophore to an active electrode. A copper or other conductive material forms an active electrode 707. The active electrode 707 and reference electrodes 711 are positioned on top of a substrate 701. An ionophore is cast to create a pre-formed ionophore 719 that is attached to a carrier or film (not shown). The pre-formed ionophore 719 and the carrier or film (not shown) is placed on top of the active electrode 707 using an adhesive or bonding film 715. The carrier or film (not shown) is then removed. In a preferred embodiment, the adhesive or bonding film is a conductive adhesive and the substrate is non-conductive. In a preferred embodiment, the copper or other conductive material is silver and the substrate is comprised of polyester. The adhesive or bonding film does not contact adjacent electrodes in a preferred embodiment. Alternatively, a z-axis tape is used to prevent adjacent electrodes from shorting.

FIG. 46B shows an ionophore covering on a carrier or film prior to application on an active electrode. The pre-formed ionophore 719 is attached to the carrier or film 721. The pre-formed ionophore 719 and the carrier or film 721 are placed on top of the active electrode 707 using the adhesive or bonding film 715. The carrier or film 721 is then removed from the pre-formed ionophore 719.

FIG. 47 shows a top perspective view, a side perspective view, and an angled perspective view of an ionophore covering formed in a continuous shape that can be handled or applied on a carrier or film that becomes an integral part of the sensor. An ionophore is cast to create a pre-formed ionophore 719. The pre-formed ionophore 719 is attached to a carrier or film 721. The pre-formed ionophore 719 and the carrier or film 721 are placed on top of an active electrode (not shown) using an adhesive or bonding film 715. In a preferred embodiment, the adhesive or bonding film is a conductive adhesive. In a preferred embodiment, the copper or other conductive material is silver and the substrate is comprised of polyester. The adhesive or bonding film does not contact adjacent electrodes in a preferred embodiment. Alternatively, a z-axis tape is used to prevent adjacent electrodes from shorting. In another embodiment, the carrier or film acts as a microfluidic absorption layer. The carrier or film is microfluidic paper in one embodiment. In yet another embodiment, the pre-formed ionophore is attached to the carrier or film using a cast bond or an adhesive.

Figure 48:
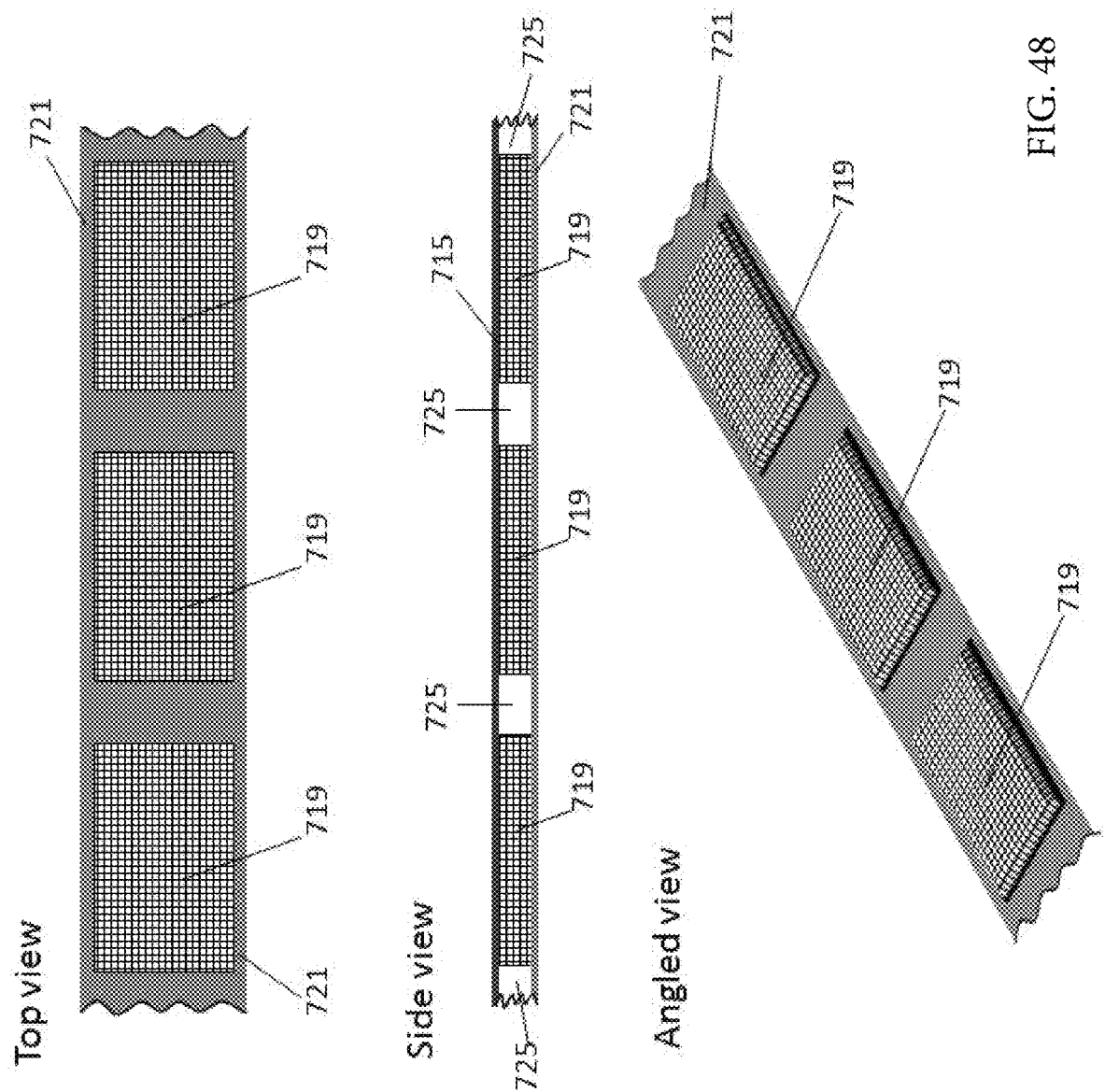
FIG. 48 shows a top perspective view, a side perspective view, and an angled perspective view of an ionophore covering formed in a non-continuous shape that can be handled or applied on a carrier or film that becomes an integral part of the sensor.

FIG. 48 shows a top perspective view, a side perspective view, and an angled perspective view of an ionophore covering formed in a non-continuous shape that can be handled or applied on a carrier or film that becomes an integral part of the sensor. An ionophore is cast to create a pre-formed ionophore 719. The pre-formed ionophore 719 is attached to a carrier or film 721. The pre-formed ionophore 719 is separated on either side by voids 725. The pre-formed ionophore 719 and the carrier or film 721 are placed on top of an active electrode (not shown) using an adhesive or bonding film 715. In a preferred embodiment, the adhesive or bonding film is a conductive adhesive. In another embodiment, the carrier or film acts as a microfluidic absorption layer. The carrier or film is microfluidic paper in one embodiment. In yet another embodiment, the pre-formed ionophore is attached to the carrier or film using a cast bond or an adhesive.

Figure 49A:
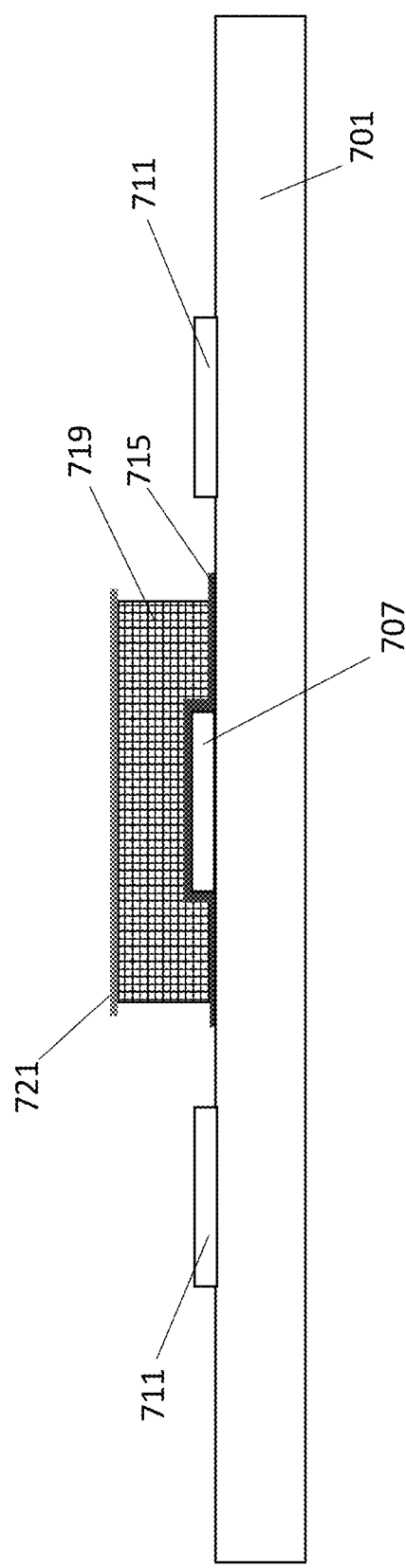
FIG. 49A shows a side perspective view of a sensor with an ionophore covering applied on a carrier or film that becomes an integral part of the sensor.

FIG. 49A shows a side perspective view of a sensor with an ionophore covering applied on a carrier or film that becomes an integral part of the sensor. A copper or other conductive material forms an active electrode 707. The active electrode 707 and reference electrodes 711 are positioned on top of a substrate 701. An ionophore is cast to create a pre-formed ionophore 719. The pre-formed ionophore 719 is attached to a carrier or film 721. The pre-formed ionophore 719 and the carrier or film 721 are placed on top of the active electrode 707 using an adhesive or bonding film 715. In a preferred embodiment, the adhesive or bonding film is a conductive adhesive. In a preferred embodiment, the copper or other conductive material is silver and the substrate is comprised of polyester. The adhesive or bonding film does not contact adjacent electrodes in a preferred embodiment. Alternatively, a z-axis tape is used to prevent adjacent electrodes from shorting. In another embodiment, the carrier or film acts as a microfluidic absorption layer. The carrier or film is microfluidic paper in one embodiment. In yet another embodiment, the pre-formed ionophore is attached to the carrier or film using a cast bond or an adhesive.

Figure 49B:
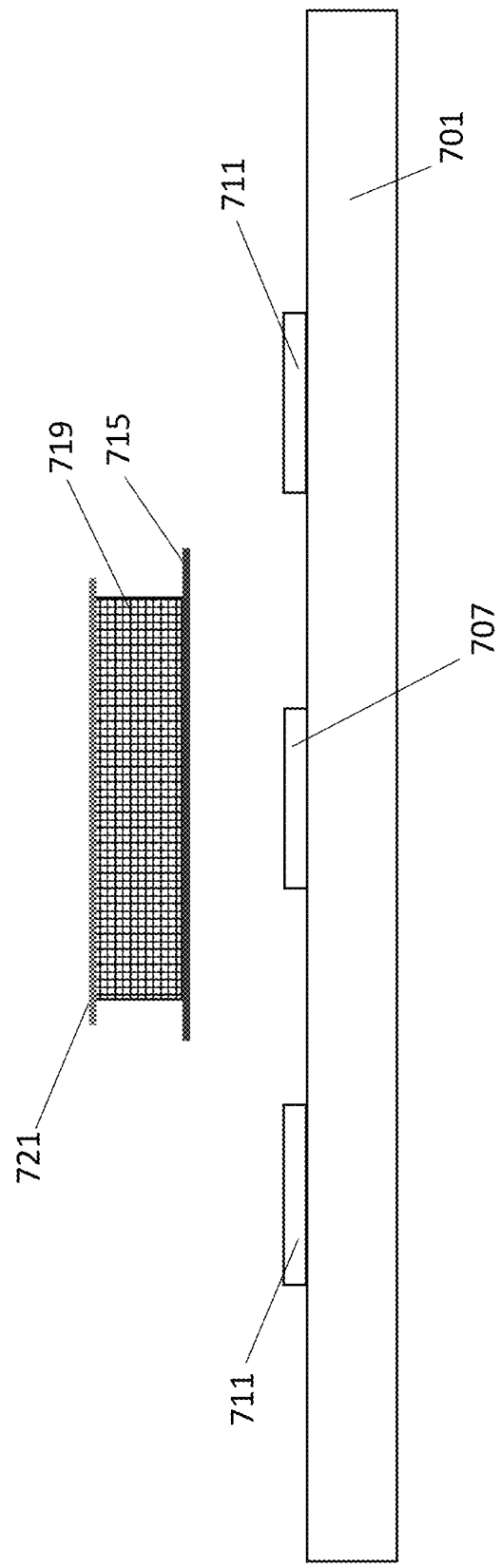
FIG. 49B shows an ionophore covering on a carrier or film prior to application on an active electrode.

FIG. 49B shows an ionophore covering on a carrier or film prior to application on an active electrode.

In another embodiment, the ionophore is formed with an embedded strength member or structure that does not impair the function of the ionophore. For example, the ionophore is cast with a glass or plastic fiber embedded in the material so that it is more durable and can be handled with greater ease in various manufacturing processes. This is similar in principle to rebar in concrete. This embedded strength approach permits laser cutting of shapes for pick-and-place manufacturing or reel-type dispensing for inline or roll-to-roll manufacturing methods.

FIG. 50 shows a top perspective view and an angled perspective view of an ionophore formed using an embedded strength approach. An ionophore is cast to create a pre-formed ionophore 719 with an embedded glass or plastic fiber 727. A cubic shape is shown in the figure, but other shapes (e.g., hexagonal, tetragonal, orthorhombic, rhombohedral, triclinic, monoclinic) are compatible with the present invention.

In one embodiment, the active and reference electrodes are aligned in a linear fashion across the sensor array to permit continuous placement of a formed or cast ionophore as a 'tape' for roll-to-roll processing. As previously mentioned, roll-to-roll manufacturing is efficient, cost effective, and allows for high production rates.

Figure 51:
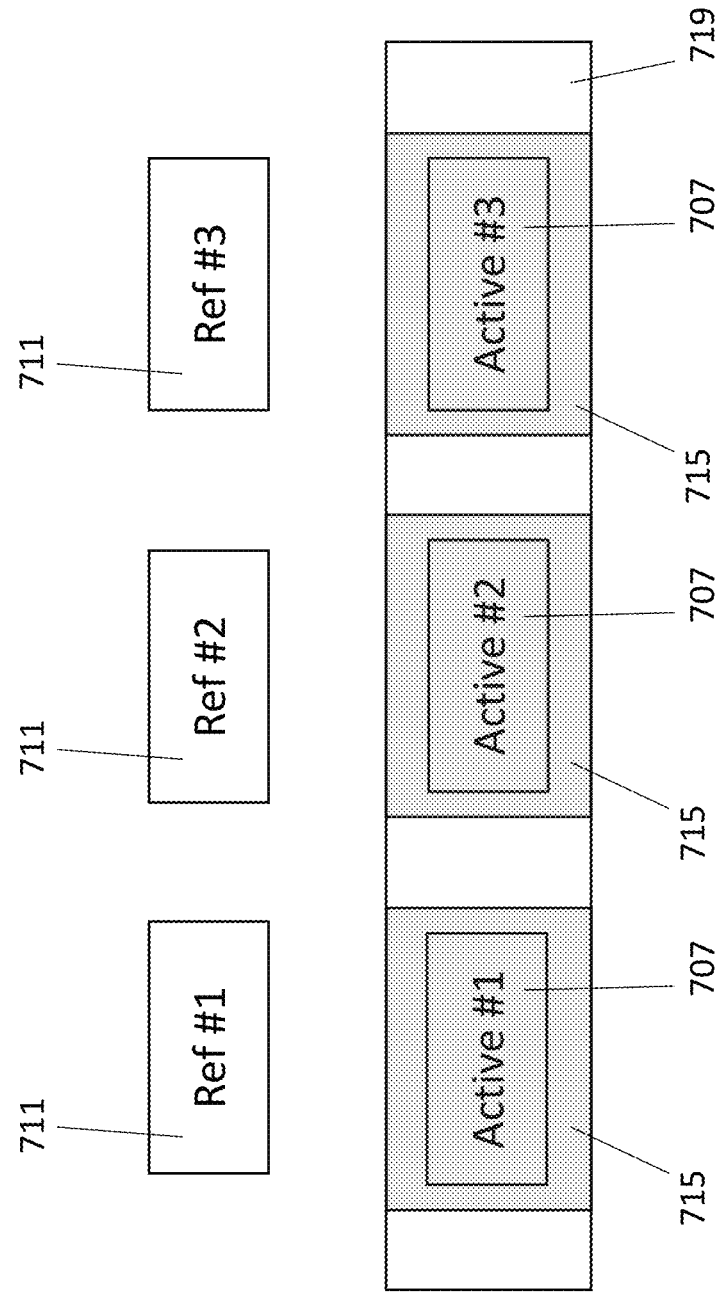
FIG. 51 shows a top perspective view of active and reference electrodes aligned in a linear fashion across the sensor array.

FIG. 51 shows a top perspective view of active and reference electrodes aligned in a linear fashion across the sensor array. A copper or other conductive material forms active electrodes 707. Reference electrodes 711 are aligned in a linear fashion across the sensor array. An ionophore is cast to create a pre-formed ionophore 719 and placed on top of the active electrodes 707 using an adhesive or bonding film 715. In a preferred embodiment, the adhesive or bonding film is a conductive adhesive. In a preferred embodiment, the copper or other conductive material is silver and the substrate is comprised of polyester. The adhesive or bonding film does not contact adjacent electrodes in a preferred embodiment. Alternatively, a z-axis tape is used to prevent adjacent electrodes from shorting.

FIG. 52A shows a side perspective view of an ionophore cast and placed on top of an active electrode using an adhesive or bonding film. A copper or other conductive material forms an active electrode 707. The active electrode 707 and reference electrodes 711 are on top of a substrate 701. An ionophore is cast to create a pre-formed ionophore 719. The pre-formed ionophore is placed on top of the active electrode 707 using an adhesive or bonding film 715. In a preferred embodiment, the adhesive or bonding film is a conductive adhesive. In a preferred embodiment, the copper or other conductive material is silver and the substrate is comprised of polyester. The adhesive or bonding film does not contact adjacent electrodes in a preferred embodiment. Alternatively, a z-axis tape is used to prevent adjacent electrodes from shorting.

FIG. 52B shows an exploded side perspective view of an ionophore cast and placed on top of an active electrode using an adhesive or bonding film.

FIG. 53A shows a side perspective view of an ionophore cast and placed on top of an active electrode without using an adhesive or bonding film. A copper or other conductive material forms an active electrode 707. The active electrode 707 and reference electrodes 711 are on top of a substrate 701. An ionophore is cast to create a pre-formed ionophore 719. The pre-formed ionophore 719 is placed on top of the active electrode 707. In a preferred embodiment, the copper or other conductive material is silver and the substrate is comprised of polyester. The pre-formed ionophore requires thermal reflow because the active electrode is not covered with a conductive adhesive.

FIG. 53B shows an exploded side perspective view of an ionophore cast and placed on top of an active electrode without using an adhesive or bonding film.

Other variations in inter-sensor spacing are also utilized in the present invention. Variations in inter-sensor spacing improve sensor performance on a human-sensor interface. Specifically, closer spacing between sensors generally contributes to crosstalk and parasitics. The location and proximity of a reference sensor can also prevent issues for chemical, electrical, and mechanical isolation. Both chemical and mechanical interactions can compromise measurements of adjacent sensors, especially when sensors are of dissimilar construction and/or electrical specification. Preferably, the location of a chloride sensor relative to a sodium sensor and/or a potassium sensor is varied to increase abrasion resistance, which mitigates stretching and/or sliding issues. Preferably, the location of the chloride sensor is not proximal to the location of Na and K sensors to avoid chemical and mechanical interactions between the sensors.

The sensor also includes a galvanic skin response sensor in one embodiment. A longer lead and/or additional ground plane under the battery are preferably utilized to resolve complications resulting from adding a galvanic skin response sensor and/or a chlorine sensor.

In yet another embodiment, utilizing alternative flex substrates and conductor construction provides increase abrasion resistance. Preferably, silver ink on polyester or a material similar to polyester is utilized.

Preferably, the sensor of the present invention does not include a jumper or a Galvanic Skin Response (GSR). In one embodiment, FR4 is added under molex or directly integrated into the BR/uC and RF antenna.

The apparatus is also optimized for efficient and successful transmission during athletic usage. When the electrodes contact the sweat biomarkers a voltage is produced. Three electrodes per analyte are used to create an average voltage value, which is transmitted to the microcontroller, wherein the microcontroller pre-processes and prepares the sensor data to be communicated to the transceiver device via Bluetooth for providing near field communication in preferred embodiments. Alternatively, an RFID, NFC, or other proprietary communications chip may be provided. The NFC chip preferably has an increased base signal amplitude for better processing and lower resolution as well as better concentration confidence and resolution. Bluetooth is preferred due to its low energy, ubiquity, and low cost. Most any Bluetooth enabled device can pair with another Bluetooth device within a given proximity, which affords more ubiquitous communication between the microcontroller and a transceiver device. The dynamic and automatic connections of Bluetooth allow for multiple microcontrollers to communicate with a single transceiver device, which, by way of example and not limitation, would provide for a team-based situation, wherein the sweat data of multiple athletes is communicated to a single coach or team database.

Another embodiment provides for utilizing NFC and/or onboard power for system control and operation, NFC and serial interfaces for data transport, external range extenders, and system integration.

Preferably, the systems and methods of the present invention are sensor agnostic, meaning that the systems and methods work with a variety of sensors. By way of example and not limitation, the systems and methods of the present invention work with multiple sensor head configurations, including variations in sensor count, single reference electrode sensors, multiple reference electrode sensors, a variety of analyte concentration, a variety of analyte sensitivity, a variety of input impedances, analog measurement conditioning, digital sampling, etc. Notably, variations in hardware and/or firmware designs provide for the sensor agnostic systems and methods of the present invention. An exemplary hardware implementation of a configurable sensor interface for multiple pinout permutations and variable analog buffering/signal conditioning supports existing and future sensor designs. Exemplary firmware designs for sensitivity and noise mitigation include, but are not limited to, variable input impedance, sampling intervals, settling time, and input switching designs. Additionally, addling a settling delay between readings also mitigates noise. One embodiment of a settling delay includes switching the multiplexer, waiting 10 ms, then taking a reading. Another embodiment for noise mitigation includes lowering the gain on the analog digital converter (ADC), which raises input impedance, to produce higher voltage levels. Adding both a settling delay and a lower ADC gain together significantly mitigate noise.

Utilizing non-adjacent channel switching on a multiplexer also reduces noise in the form of crosstalk and/or ghosting. Specifically, firmware methods for sensor switching and measurement times include non-adjacent multiplexer selection and sensor specific settling times from sensor selection to ADC sampling. Standard single chip multiplexers can experience adjacent channel crosstalk or 'ghosting' from large impedance changes that can manifest as noise or erroneous measurements. Firmware solutions to avoid direct adjacency in measurement selection can reduce these effects and improve measurement electronics performance. This is particularly important in low signal environments.

Complex sensor selection methods can propagate transition noise into the measurement electronics. The settling time constant for different sensor types and variations due to sensor-human interactions can present wide fluctuations that are hard to manage with filtering. Firmware controlled selection-to-measurement time delays can mitigate these effects. This can be implemented on a per sensor type basis for systems with dissimilar sensor types. As an example, a 'ring reference' ion-selective electrode (ISE) has more localized/uniform human contact behavior across the active sensor and its associated reference. In contrast, a 'single reference-multiple sensor' ISE can have widely differing human contact behavior due to the distributed physical placement of the single reference and the specific sensor heads.

The systems and methods of the present invention preferably enable end-to-end flow and processing using a patch, wherein the data is eventually transmitted to a device or to the cloud for data processing and analytics. The patch preferably includes electronics and firmware to properly buffer, amplify, and manage timing required to optimize patch functions. The firmware is preferably modularized to enable engineers to set designated variables, filters, noise thresholds, and other attributes needed to accommodate many different sensor types, modalities, sensitivities, and other characteristics.

The present invention also provides systems and methods for addressing fault detection and isolation, electromagnetic compatibility (EMC) detection, radiofrequency interference detection, mitigation and event handling, addition of encryption for data integrity, personally identifiable information (PII) protection, and communications security.

Figure 10:
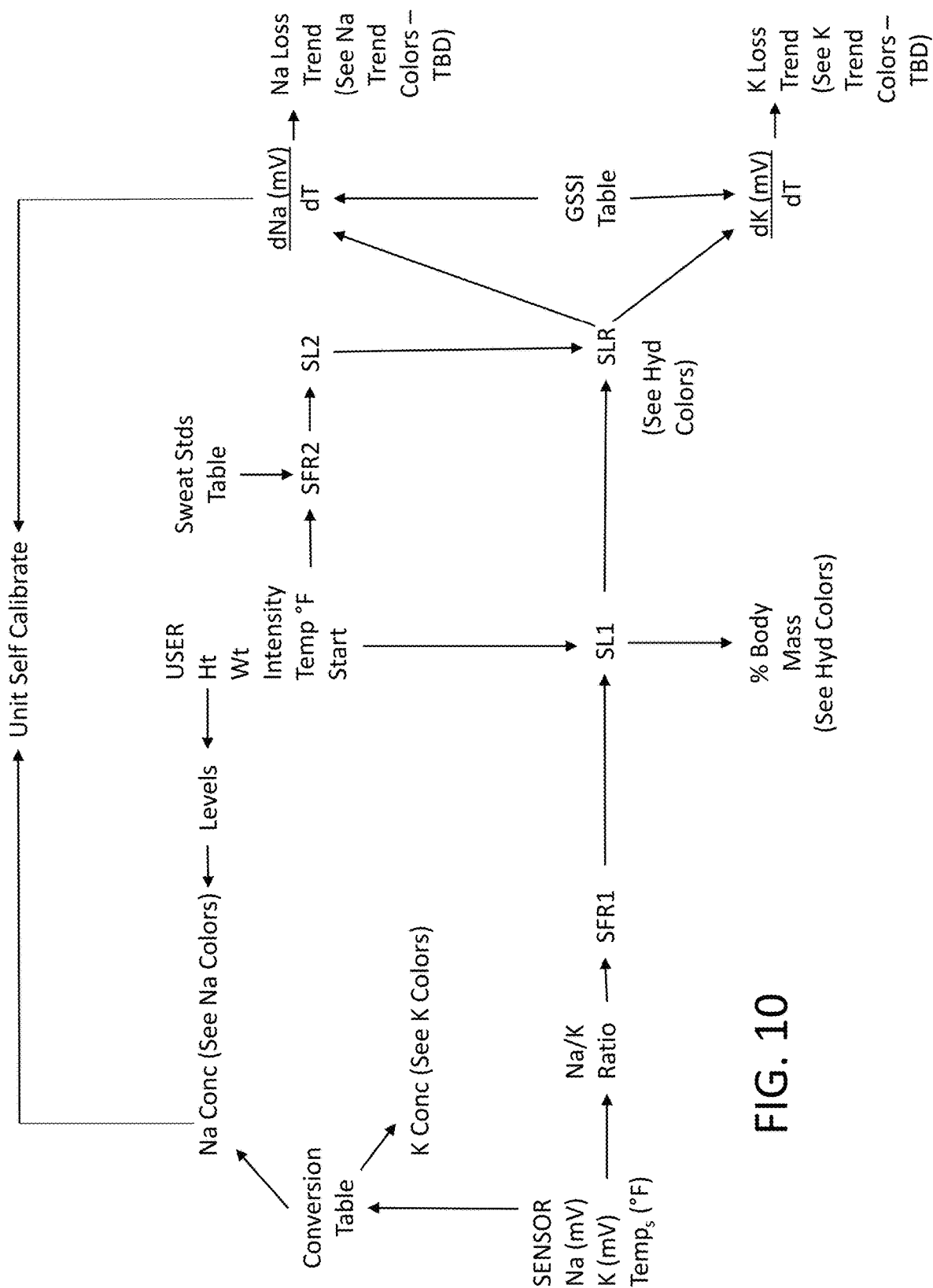
FIG. 10 shows a diagram of the analytical process within the sensor apparatus.
Figure 17:
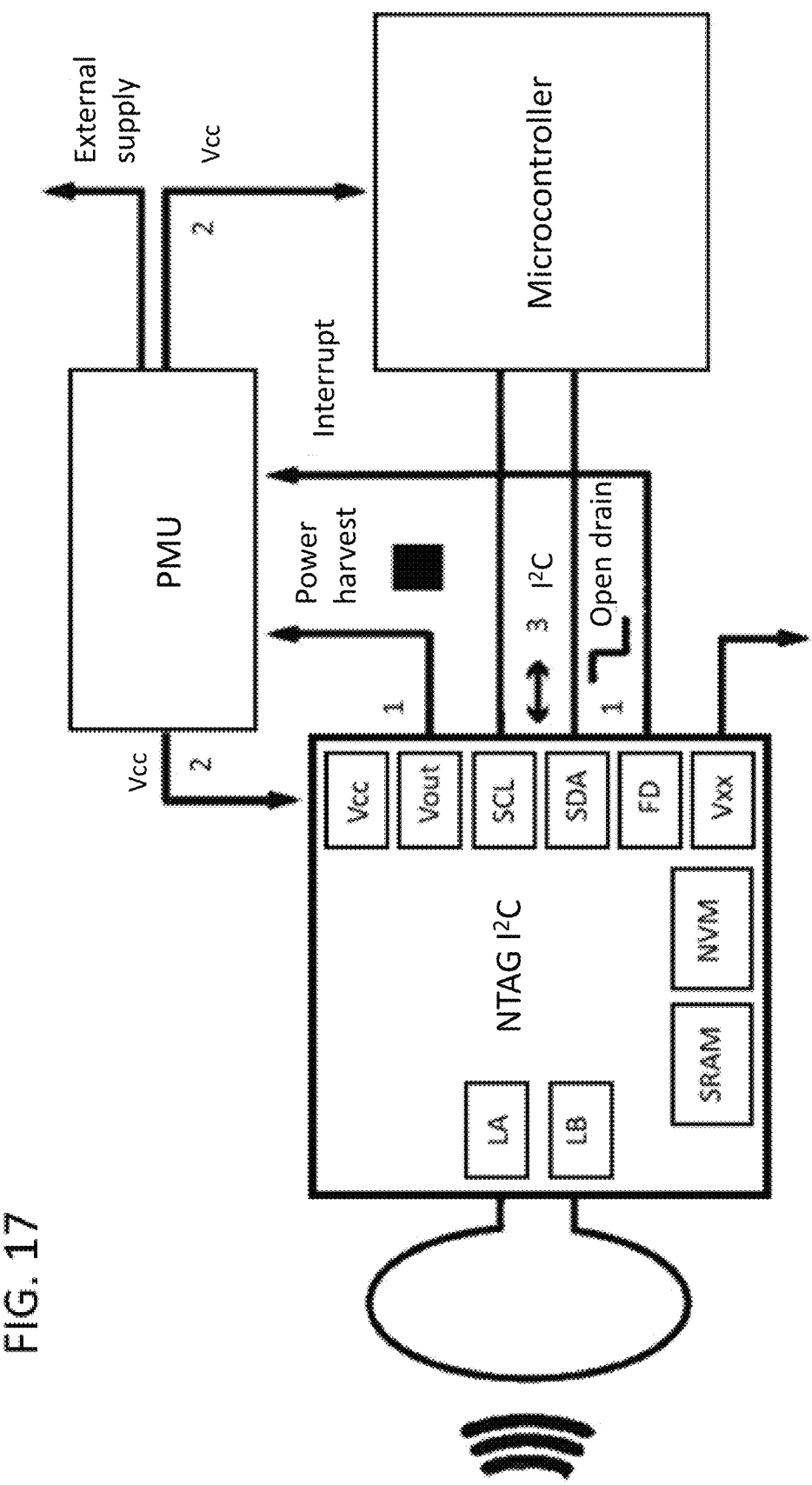
FIG. 17 shows a diagram of a NXP semiconductor used in an embodiment of the sensor apparatus.
Figure 18:
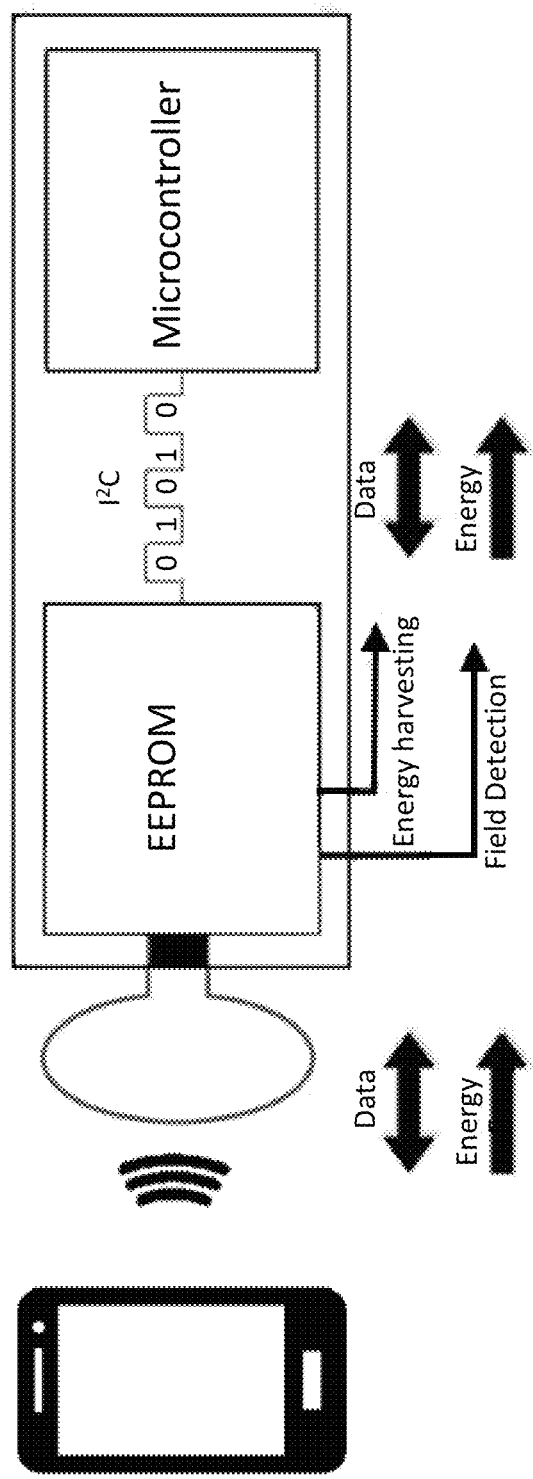
FIG. 18 shows a diagram of the communication between a NXP semiconductor and a wireless device in an embodiment of the sensor apparatus.
Figure 19:
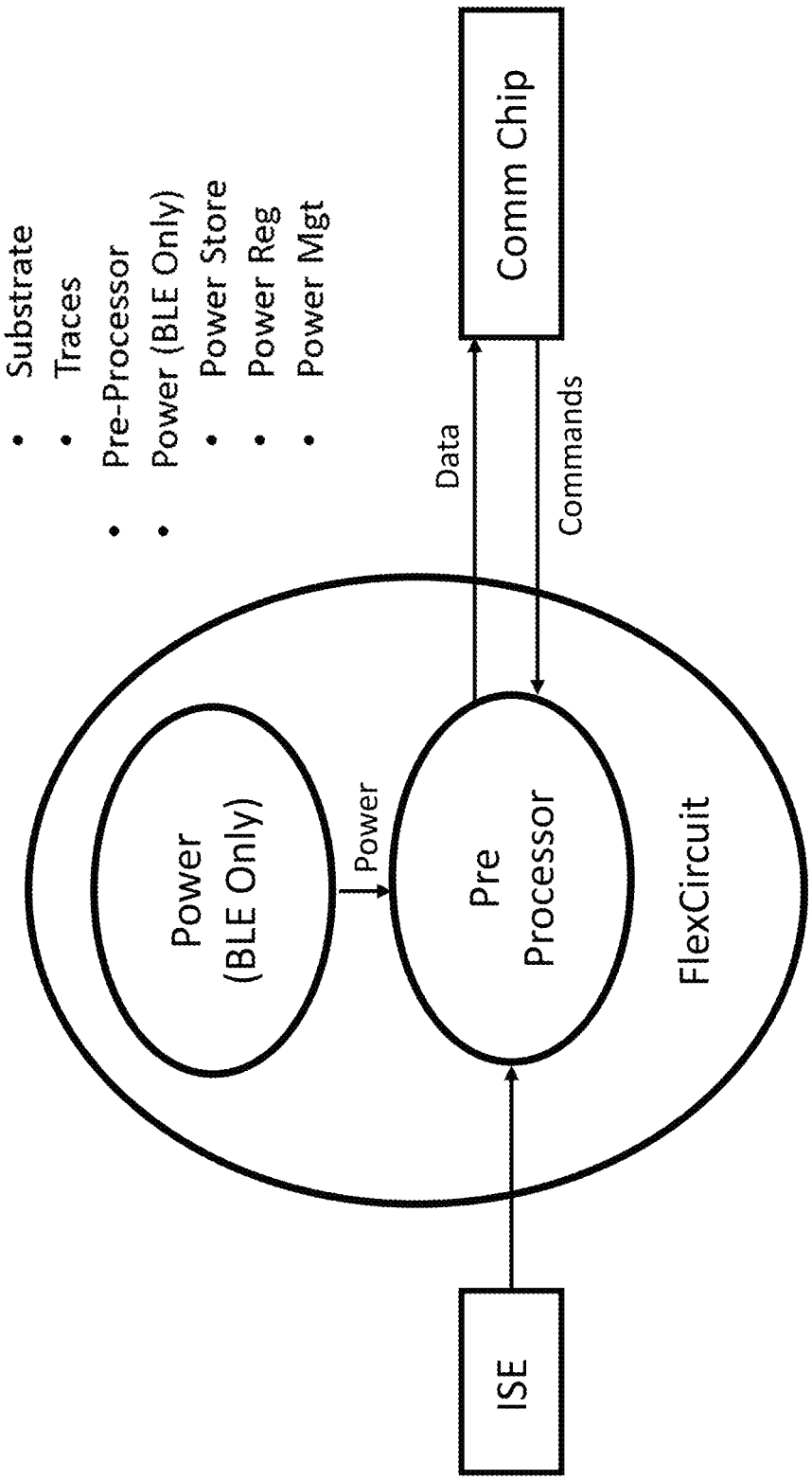
FIG. 19 shows a diagram of a sweat microcircuit of the sensor apparatus.

A second source of input data is the remote transceiver device. By two-way communication, the transceiver device may transmit data to the microcontroller of the apparatus, which is part of an inter-integrated circuit, as shown in FIGS. 17 and 18. The data to be transmitted will have been manually or automatically input in the transceiver device. For example and not limitation, as shown in FIG. 10, types of manually input data may include gender, fitness or conditioning level, age, and anthropomorphic data such as height and weight. The anthropomorphic data is preferably used to estimate user body surface area, which is a critical variable for accurately determining sweat loss and electrolyte loss. More preferably, estimates are a product of anthropomorphic data, gender, and age. Prior art assumes a body surface area of about 2 m² to calculate sweat loss and electrolyte loss. Using anthropomorphic variables, as in the present invention, consistently decreases calculated error rate from between about 50 and about 70 percent to less than about 10 percent, preferably. The accuracy resulting from body mass estimation revealed that persons with larger body mass, such as males, more readily adapt to physical exertion by sweating more quickly, a larger volume, and lower electrolyte concentration. Similarly, a physically fit person with a small body mass, such as a female, adapts to physical exertion by adjusting sweat flow rates and electrolyte levels. Although prior art has validly analyzed sodium, potassium, sweat rates, etc., it has failed to account for body surface area, mass and $VO_2$ max (maximum rate of oxygen consumption), thus inflating calculated error rate. These data support that sweat flow rates and electrolyte loss is strongly correlated with body size and surface area and conditioning level, which further supports the need for proper estimation of body size, such as through anthropomorphic variables.

Figure 11E:
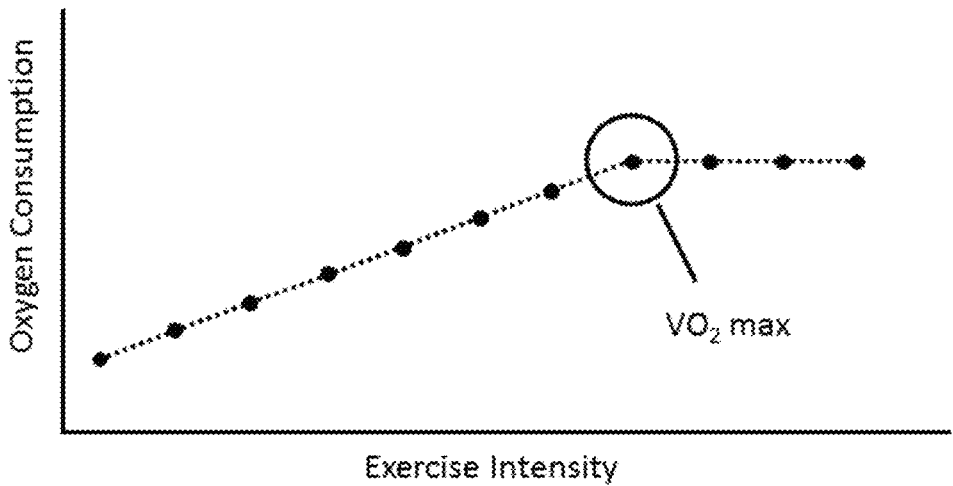
FIG. 11E shows a chart of oxygen consumption vs. exercise intensity and tables for $VO_2$ max for men and women.
Figure 14:
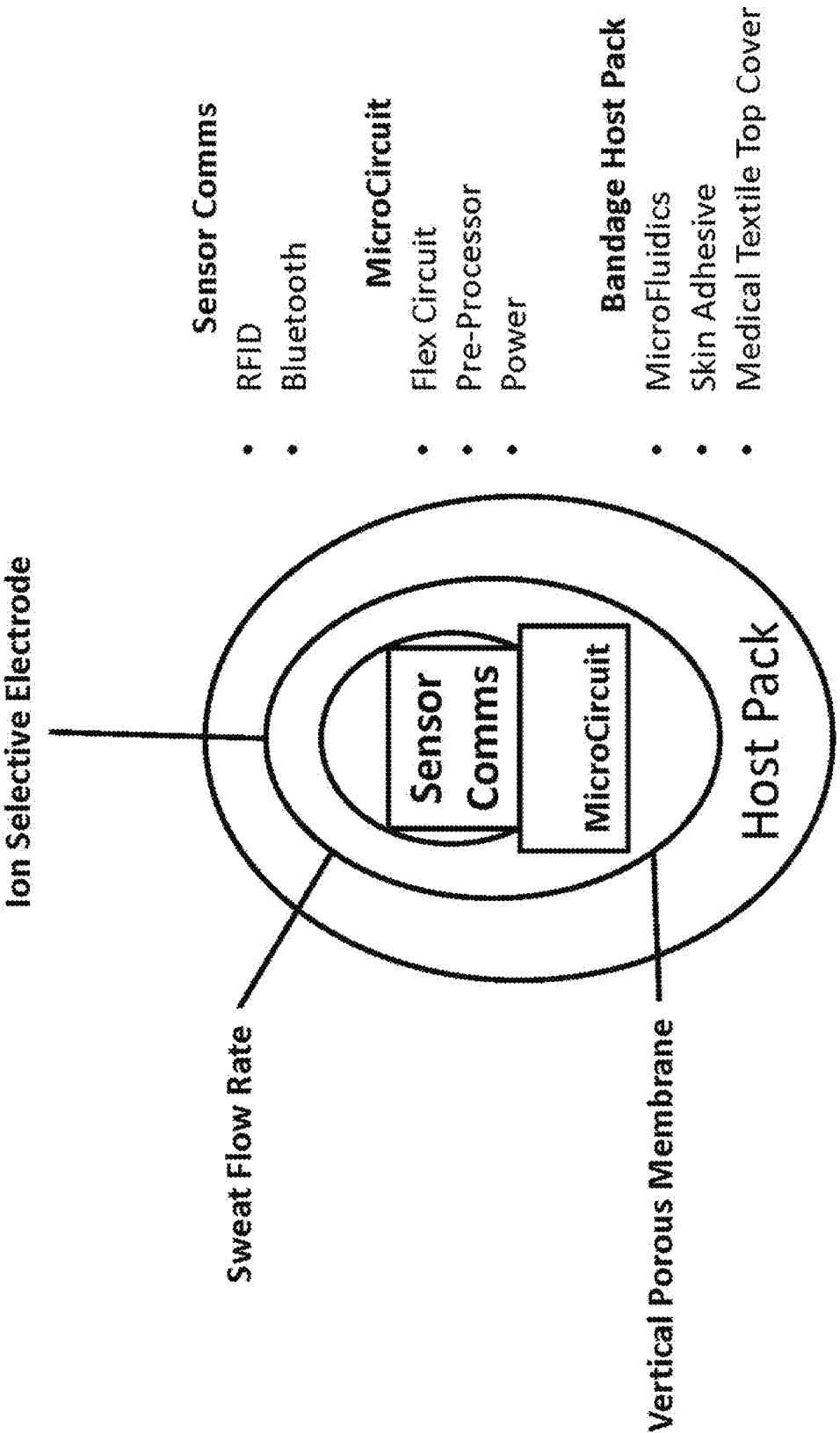
FIG. 14 shows a diagram of the sweat sensor subsystem.

Accurately measuring $VO_2$ max generally requires testing with a treadmill or bicycle in a laboratory. Exercise intensity is progressively increased while measuring the volume of inhaled and exhaled air and the oxygen and carbon dioxide concentrations of inhaled and exhaled air. $VO_2$ max is the point at which oxygen consumption plateaus despite an increase in exercise intensity as shown on the chart in FIG. 11E. Alternatively, $VO_2$ max can be estimated using a number of physical tests, including but not limited to, the Uth-Sorensen-Overgaard-Pedersen estimation, the Cooper test, the Multi-stage fitness test (or beep test), a step test (e.g., Harvard Step Test, Queens College Step Test, Tecumseh Step Test), Storer Maximal Cycle Test, or the Rockport fitness walking test. $VO_2$ max can also be predicted using an exercise history questionnaire, age, height, weight, and gender (e.g., Jackson) or a perceived functional ability, physical activity rating scale, height, weight, and gender (e.g., George). In an alternative embodiment, $VO_2$ max is estimated using data obtained from GPS devices, heart rate monitors, and fitness bands (e.g., UA Band, Garmin, Polar, Fitbit, TomTom, Soleus, Timex, Mio, Jawbone, Zephyr), mobile devices (e.g., iPhone, Android), and/or social networks and mobile applications (e.g., Record by Under Armour, MapMyRun, MapMyRide, MapMyFitness, Endomondo, Strava, dailymile). $VO_2$ max can be estimated by using factors including but not limited to maximum heart rate, resting heart rate, distance run in a specific time, time to run a specific distance, gender, age, body weight, body mass, number of times a user exercises per week, and heart rate after exertion. In an alternative embodiment, $VO_2$ max is estimated using expected values, which are dependent on age, gender, and a self-reported rating, as shown in FIG. 11E. $VO_2$ max decreases approximately 0.54 mL/kg/min per year for women and approximately 0.35 mL/kg/min per year in men.

Other types of manually input data include metabolic disorder, such as diabetes. Since Type 1 diabetes is associated with reduced eccrine gland activation and, thus, lower sweat rates, the present invention may reveal user metabolic disorder. Further, automatically input data includes user skin temperature, outdoor or indoor temperature, time, date, humidity, and/or altitude. This data is also input manually in another embodiment. Other automatically input data and/or manually input data includes exertion levels and/or body mass. The automatically input data may be generated in the remote transceiver device by integrated applications, such as GPS or weather. Together, the data transmitted to the microcontroller from the remote transceiver device represent modifying variables. Preferably, microcontroller software and/or software on the computing device is operable to compensate for variations across the automatically and/or manually input data.

The microcontroller converts the voltage data from the biological fluid into a concentration or ratio value of the biomarker using at least one programmed algorithm. For example, as shown in FIG. 11A, if the algorithm was converting the amount of sodium ions detected at the sensor into a sodium concentration, the algorithm would apply around 0.242 mM per mV of sodium. For potassium conversion, the ratio would be around 0.195 mM per mV of potassium. The article Excretion of Sodium and Potassium in Human Sweat, by Schwartz, et al. in J. Clin. Invest. 1956

January; 35(1); 114-120, which is incorporated by reference herein in its entirety, examines the concentrations of sodium and potassium in human sweat following administration of a cholinergic drug. In one embodiment, sensor data are inputs into real time blood serum hydration, sodium concentration, and potassium concentration using absorption and extraction models that use sensor data as starting points. These calculated values are the apparatus' output data. Types of output data include but are not limited to concentrations, such as molarity, osmolarity, and osmolality, and descriptive statistics, such as averages, ratios, and trends, all of which may be categorized based on a sub-range within a larger physiological range of the biomarker, as shown in FIG. 13A. The modifying variables transmitted from the remote transceiver device may modify the algorithm, which may adjust the output data.

Figure 16:
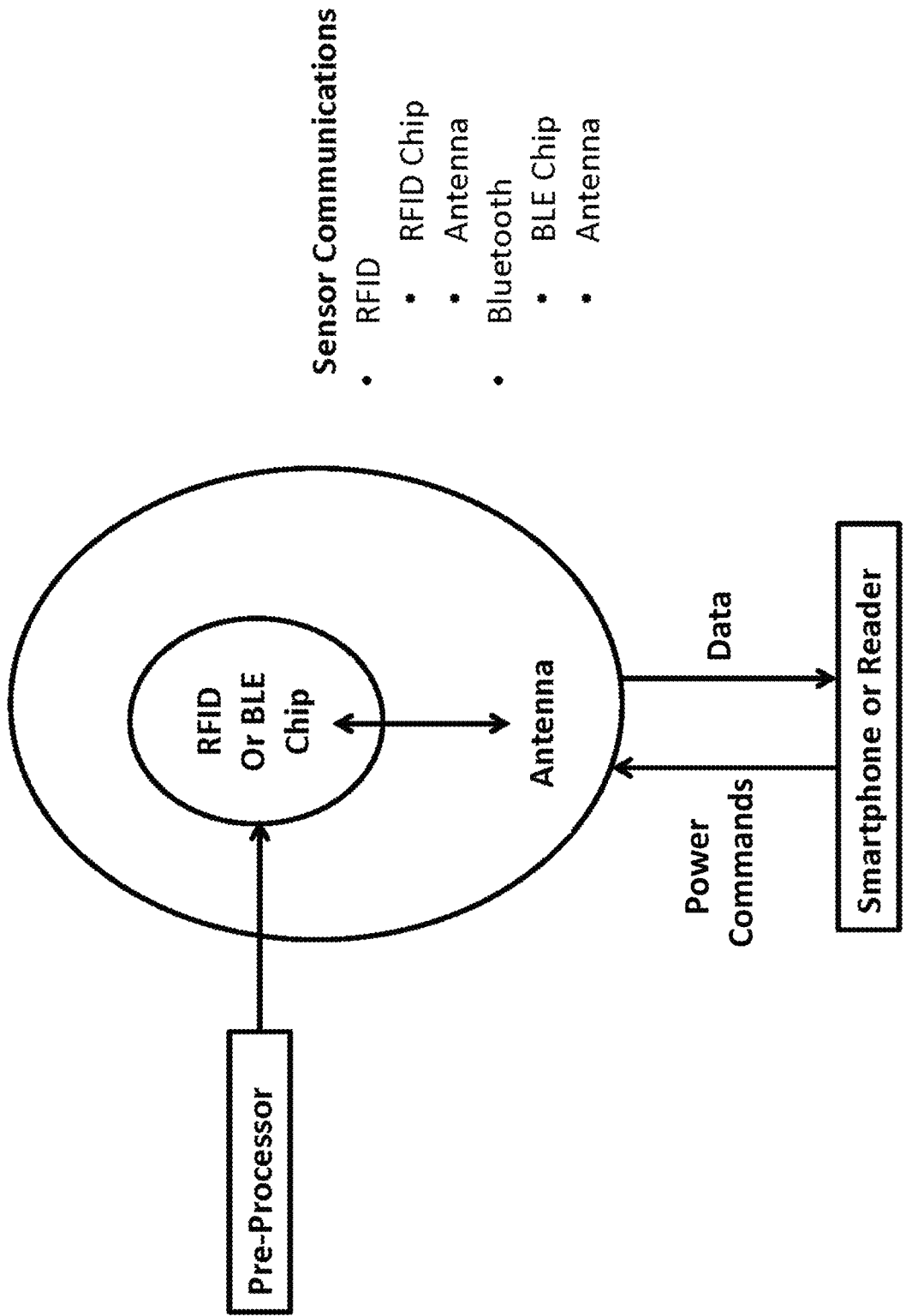
FIG. 16 shows a diagram of sweat sensor communications.

The output data is then transmitted from the apparatus to a remote computer device, such as by way of example and not limitation, a smartphone, a tablet computer, or wearable computer, preferably, through wireless network communication by the transceiver antenna (which may include a coil) of the apparatus. Using a larger antenna in the present invention provided for lower data loss and easier reads associated with a broad x-y placement tolerance. The wireless transmission is provided by any suitable wireless communication, wireless network communication, standards-based or non-standards-based, by way of example and not limitation, radiofrequency, Bluetooth, Zigbee, Wi-Fi, near field communication, or other similar commercially utilized standards. At the remote transceiver device, the output data can be viewed and assessed by the one or multiple users. The one or more users also may manipulate or further analyze the output data, such as by creating user defined graphs and tables. Preferably, the remote transceiver device is portable. More preferably, the device is a smartphone. Alternative devices include bulk readers, such as food and or beverage dispensers with sensor and/or mobile app communication capabilities or athletic training gear including treadmills, spin bikes, ellipticals, stair climbers, and weight machines with integrated mobile communication capabilities. More alternative devices include desktop or laptop computers and tablets. FIG. 16 diagrams the communication between the sensor apparatus and the smartphone or reader, wherein power, commands, and/or data may be communicated.

From the remote transceiver device, the user may transmit processed or unprocessed data to at least one remote computer server, preferably by wireless communication, such as through a user web service. The remote computer server, which may be a network or cloud, may store the transmitted data in a library. The cloud preferably serves as a software development kit (SDK) for potential solution partners, a cloud based user app (with real time ingestion, calculation, and display), and a cloud based user store with ubiquitous access.

Figure 29:
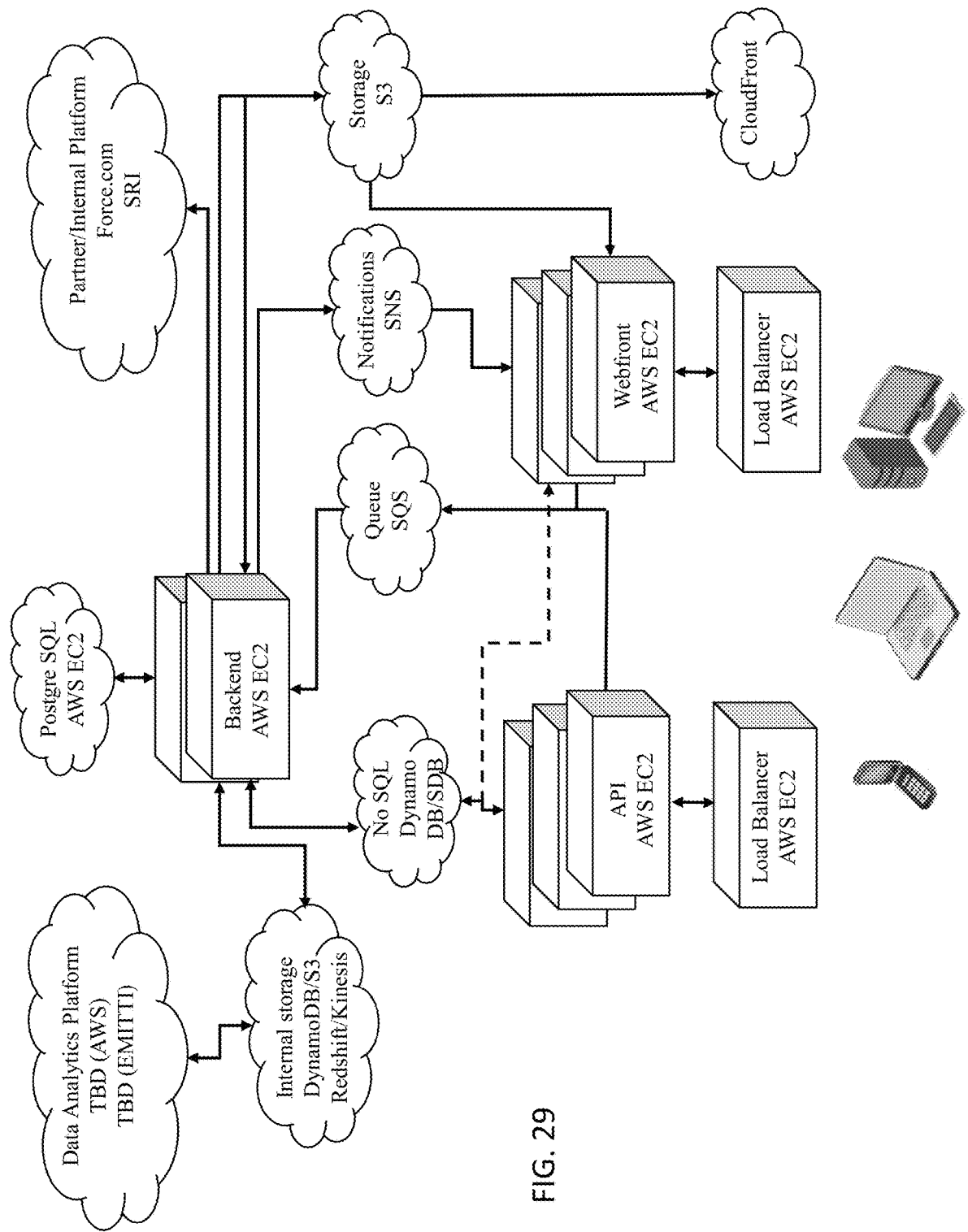
FIG. 29 shows a diagram of a cloud enterprise.

The library includes functions, such as file storage, security, extensions, utilities, scheduling, messaging, persistence, cache, and logging. FIG. 29 shows a cloud enterprise, wherein a cloud computing platform receives data from application users and processes it for internal and partner use. The software code that resides in a cloud-based computer system of the present invention is designed, constructed, and configured to handle the unique data in unique ways. It automatically validates data (to determine if it is reasonable/useable data) and triggers a series of workflows based on the type, date/time stamps, and scope of data to correlate and identify trends. It further includes correlation and trending tags for subsequent user alerts/analysis. The code has an open framework built on web service concepts to interact and integrate with other $3^{rd}$ party analytics. These web service calls are a series of open Application Programming Interfaces (APIs) aggregated into a Software Development Kit (SDK) which enables authorized $3^{rd}$ party developers to create and maintain $3^{rd}$ party user apps that leverage the cloud infrastructure to access/share data, correlations, trends, and other analytic results.

The two-way communication between the apparatus and the remote transceiver device is significant for the fullness of system functionality. As shown in FIG. 16, the remote transceiver device may communicate with the apparatus to provide, by way of example and not limitation, commands, electrode calibration, microcontroller software updates, new or updated algorithms, and/or new or updated modifying variables for algorithms. Communication may be manually or audibly activated. The apparatus may communicate with the remote transceiver device to provide, by way of example and not limitation, output data, microcontroller health properties, error codes, electrode maintenance or malfunction. At the transceiver device, the one or more users may separately or simultaneously view selected session tables, full history session tables, sensor or multi-sensor chronology, and external sensor correlation. Further, selected biomarker or multi-biomarker histories may be viewed.

Figure 20:
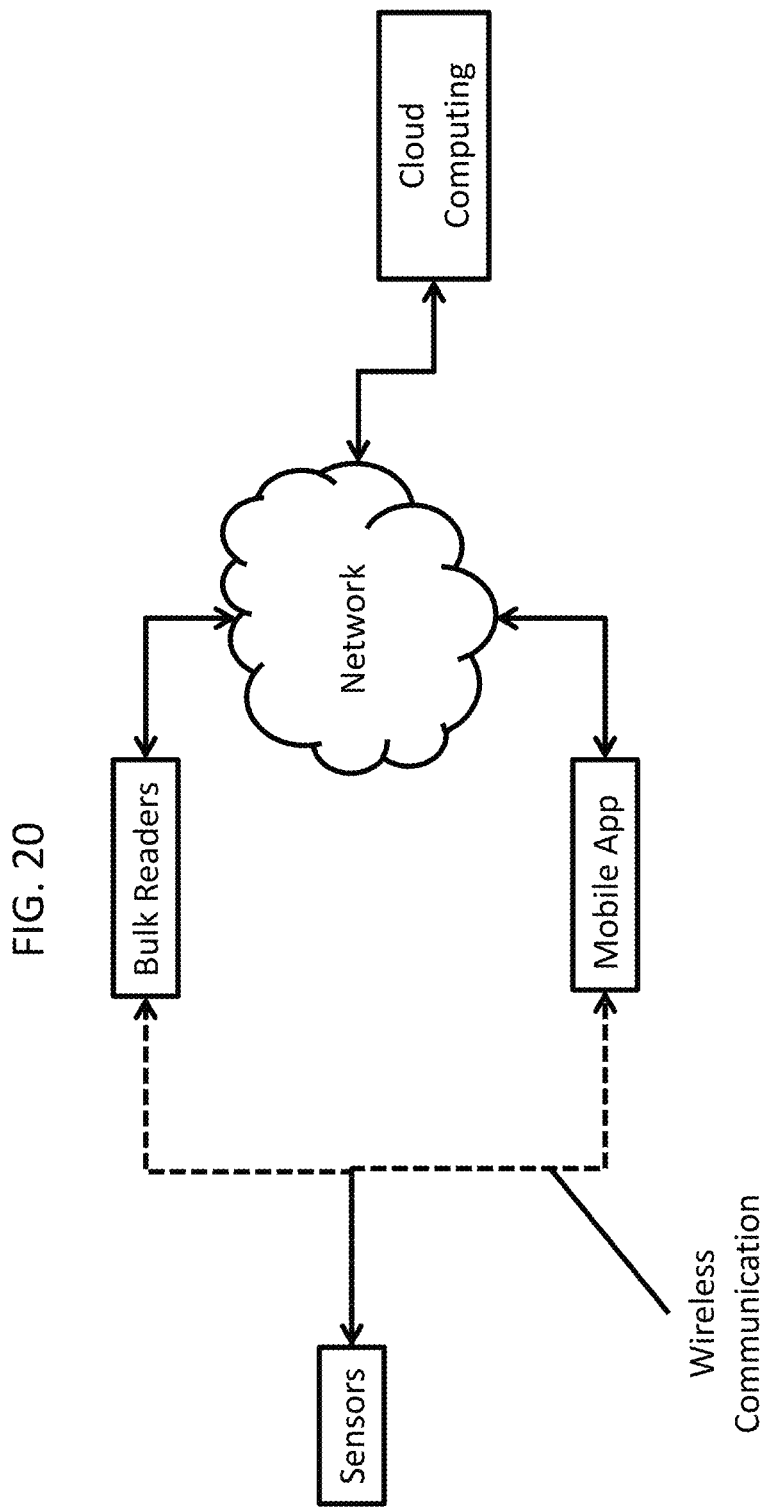
FIG. 20 shows a diagram of the system architecture.
Figure 21:
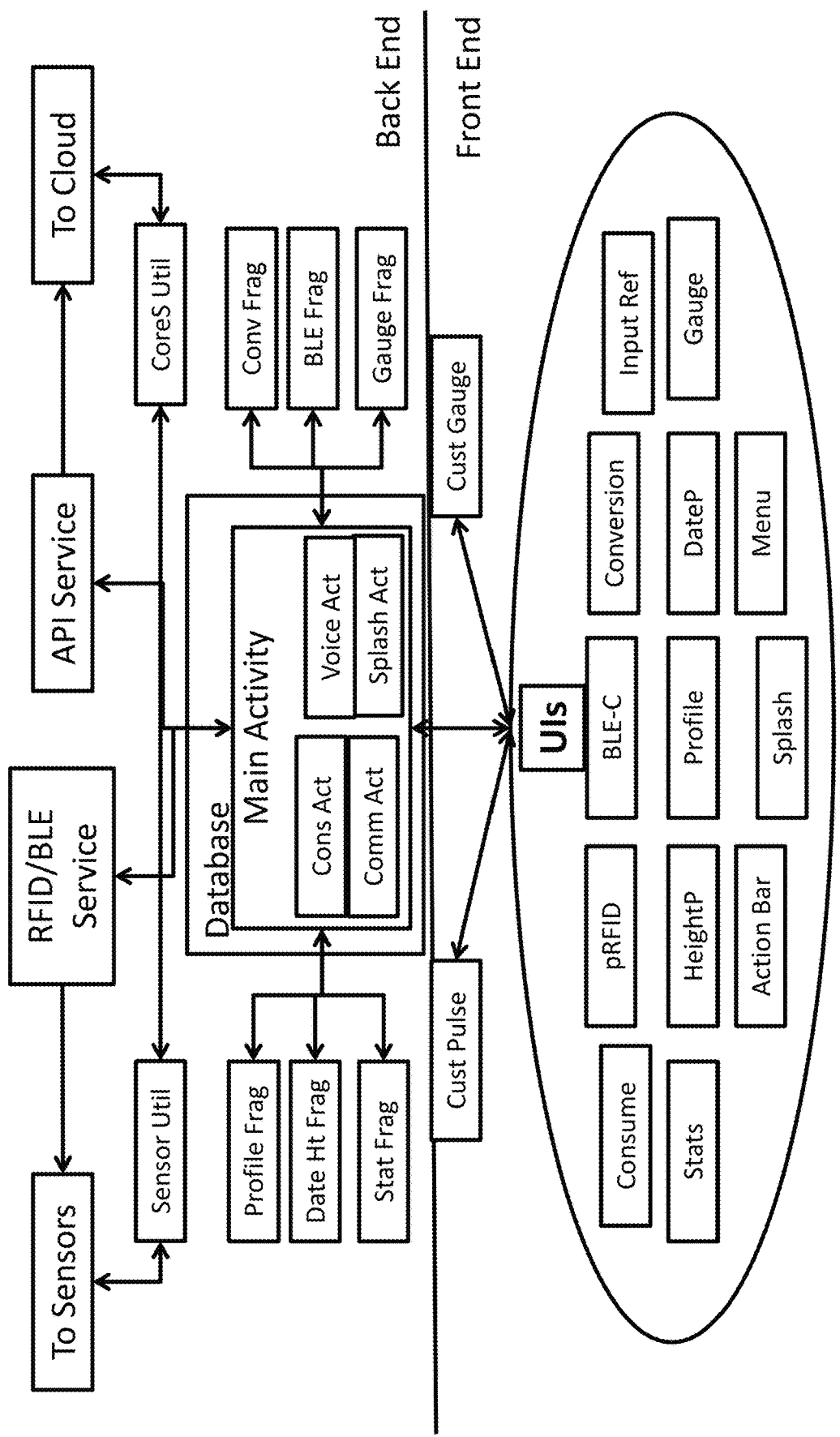
FIG. 21 shows a diagram of the controls within the user mobile app of the wireless remote transceiver.
Figure 22:
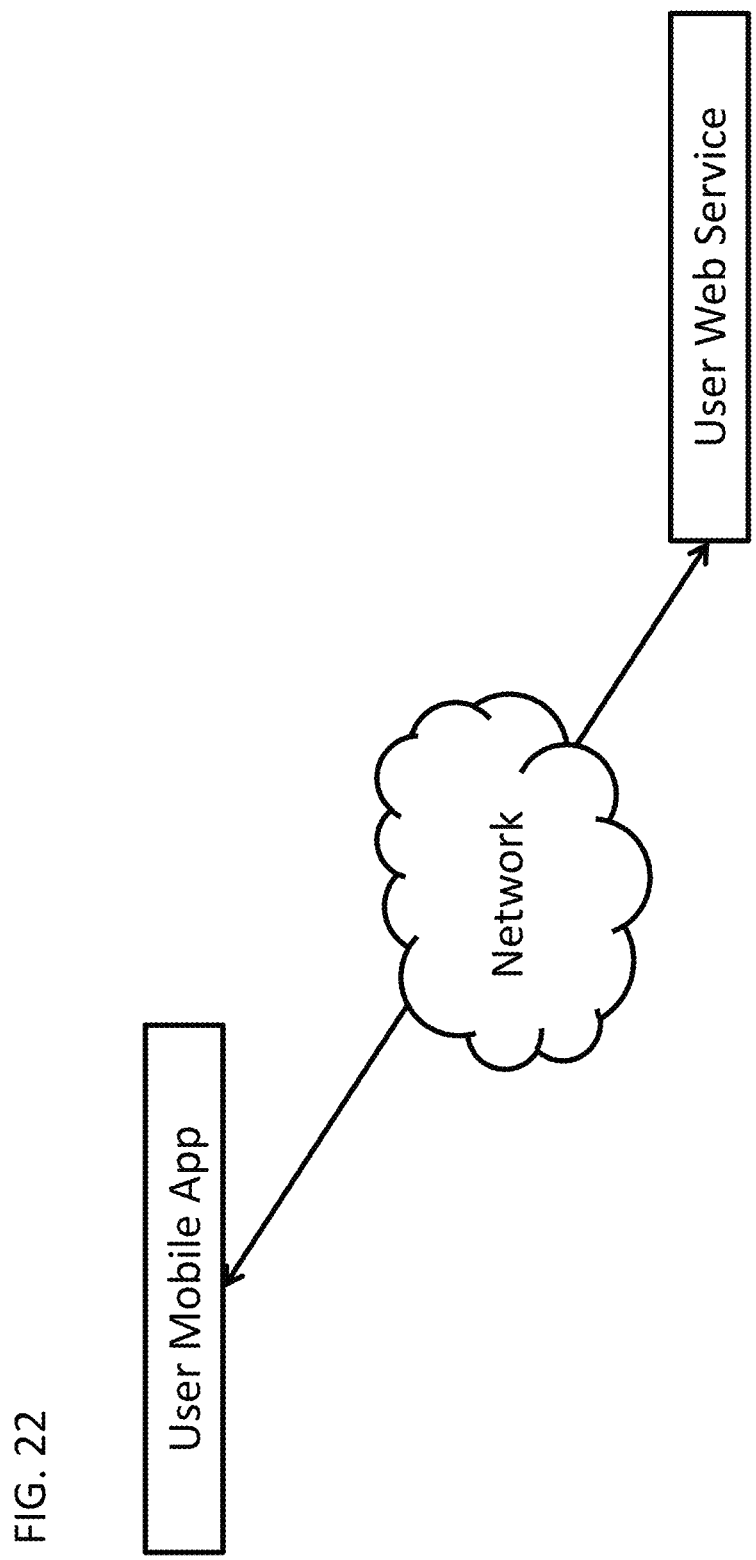
FIG. 22 shows a diagram of the network connection between the user mobile app and the user web service.
Figure 23:
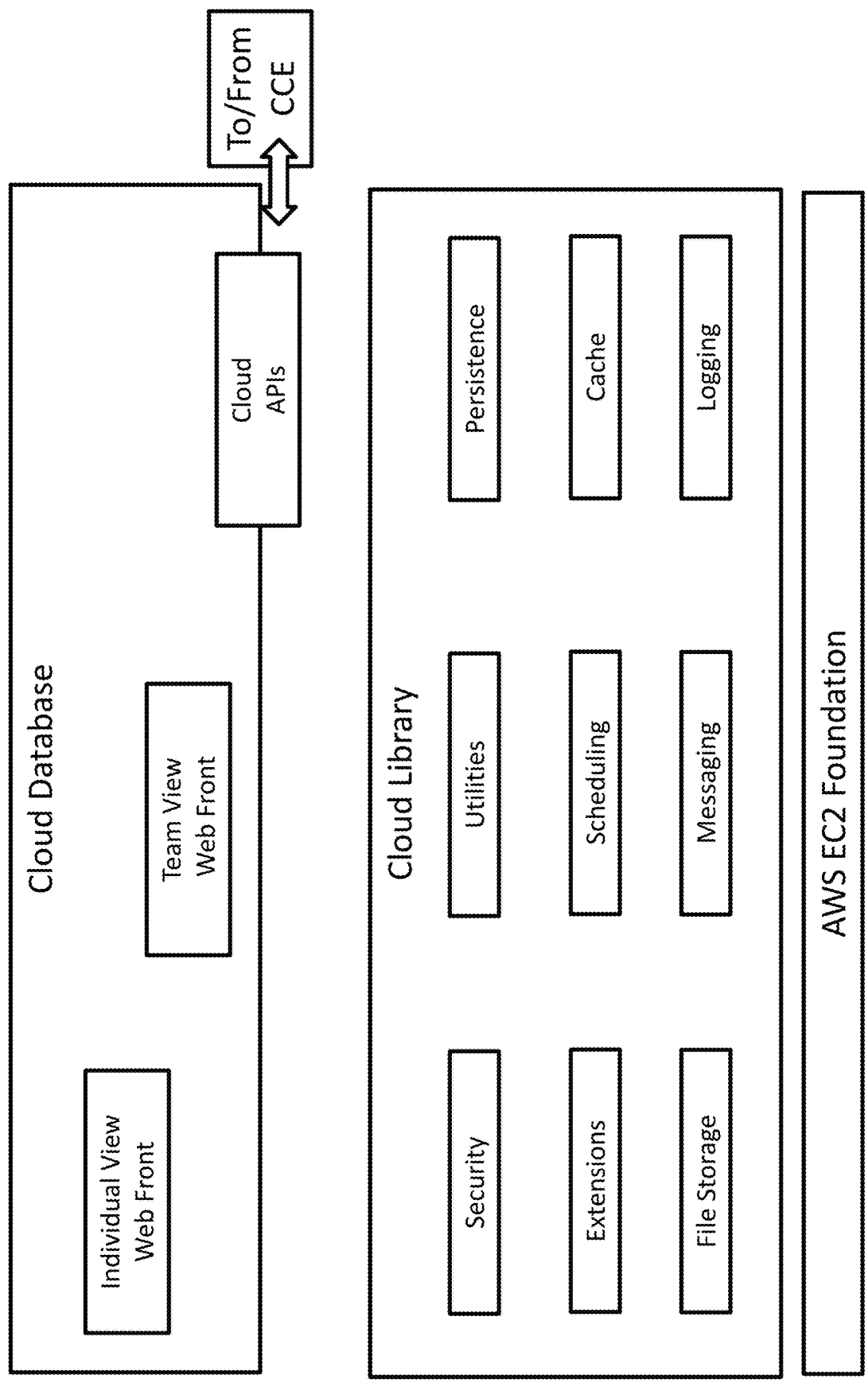
FIG. 23 shows a diagram of the controls within the cloud database and library, which are part of the user web service.
Figure 24:
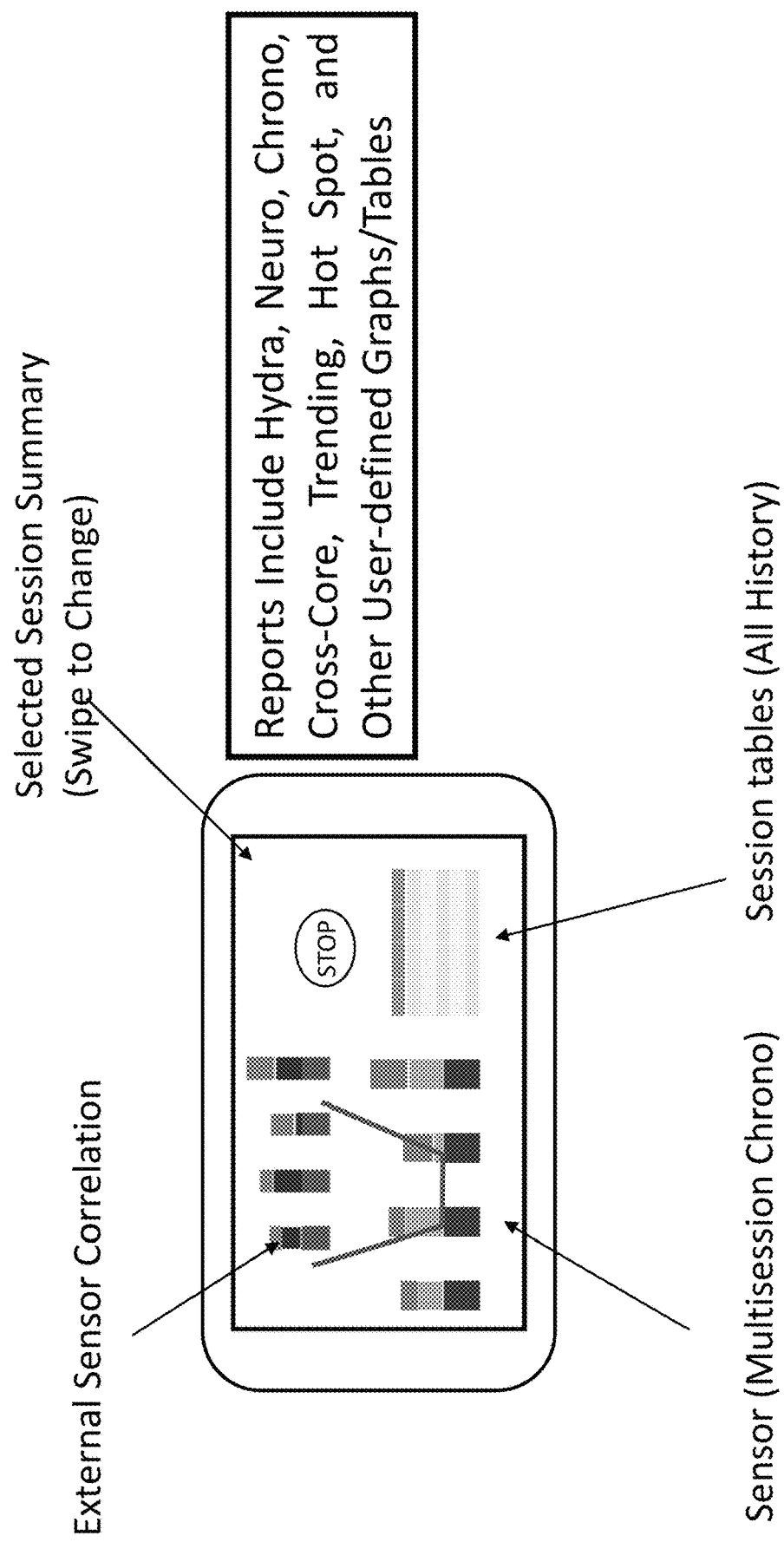
FIG. 24 shows an individual view of the user web front.
Figure 25:
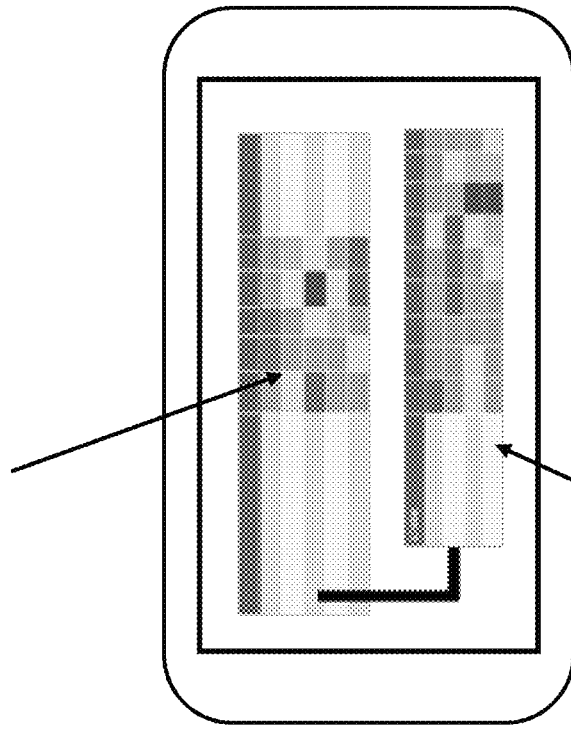
FIG. 25 shows a multi-user view of the user web front.
Figure 26:
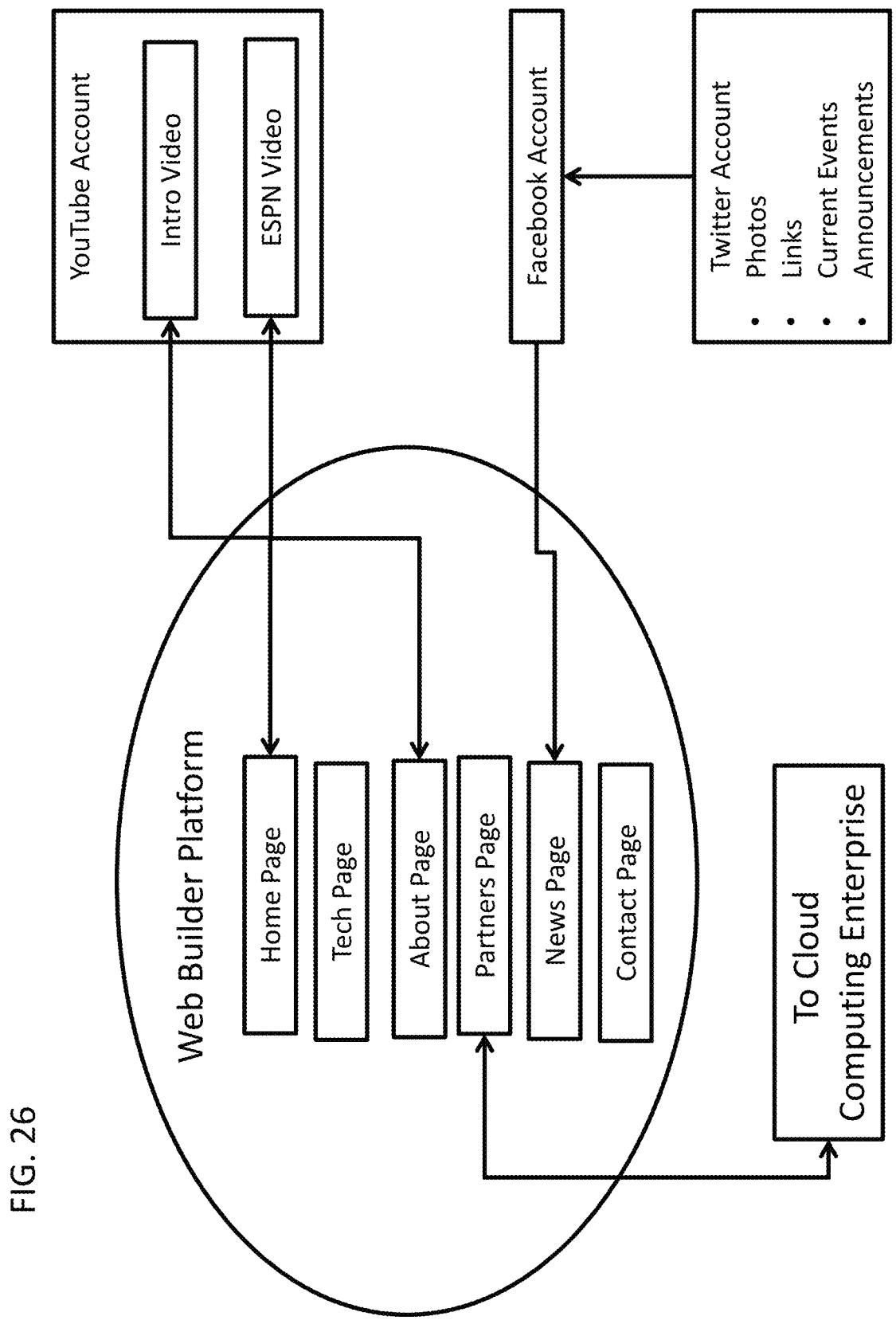
FIG. 26 shows a diagram of the controls within the present invention's website.
Figure 28:
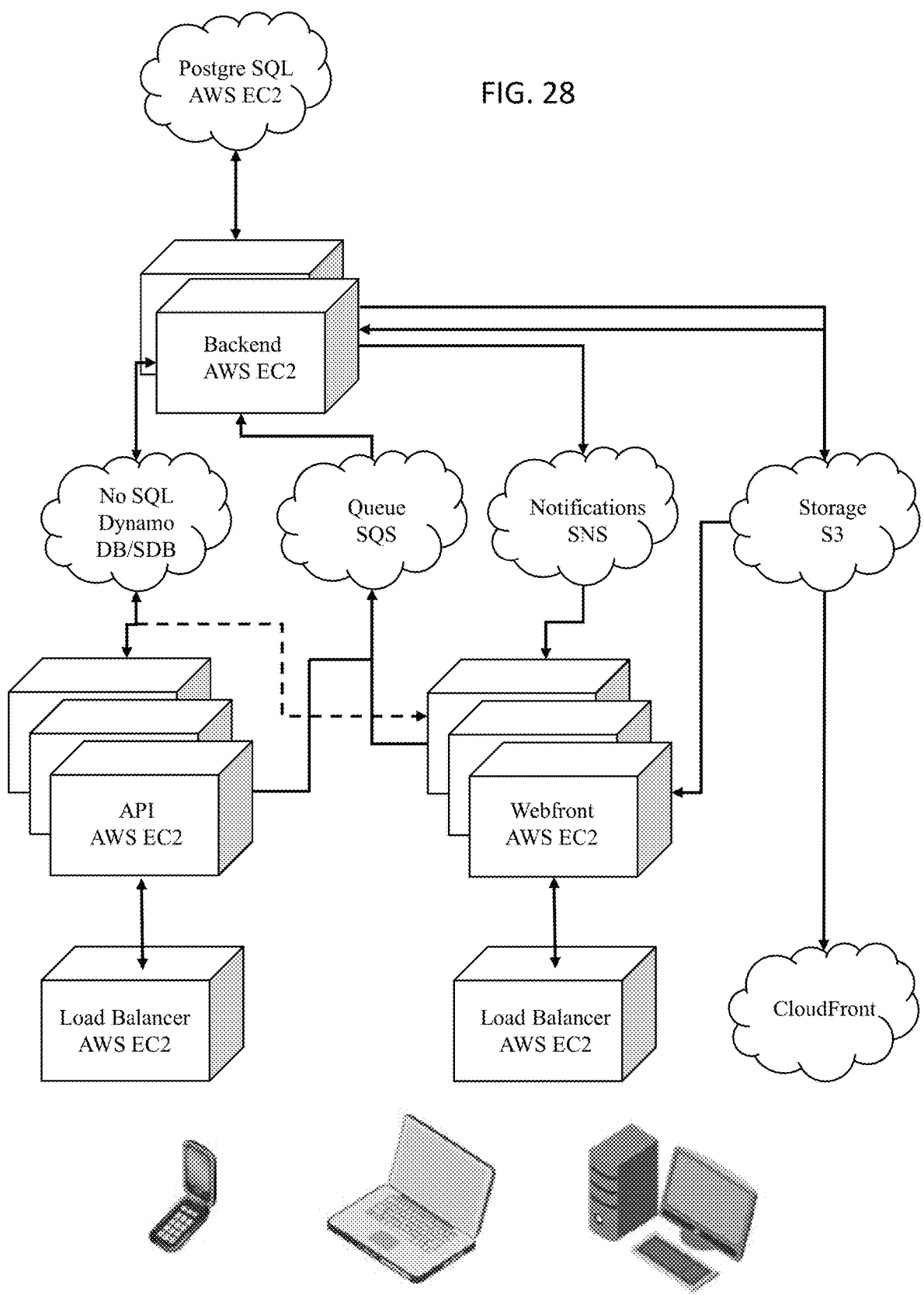
FIG. 28 shows a diagram of the generic cloud architecture.
Figure 30:
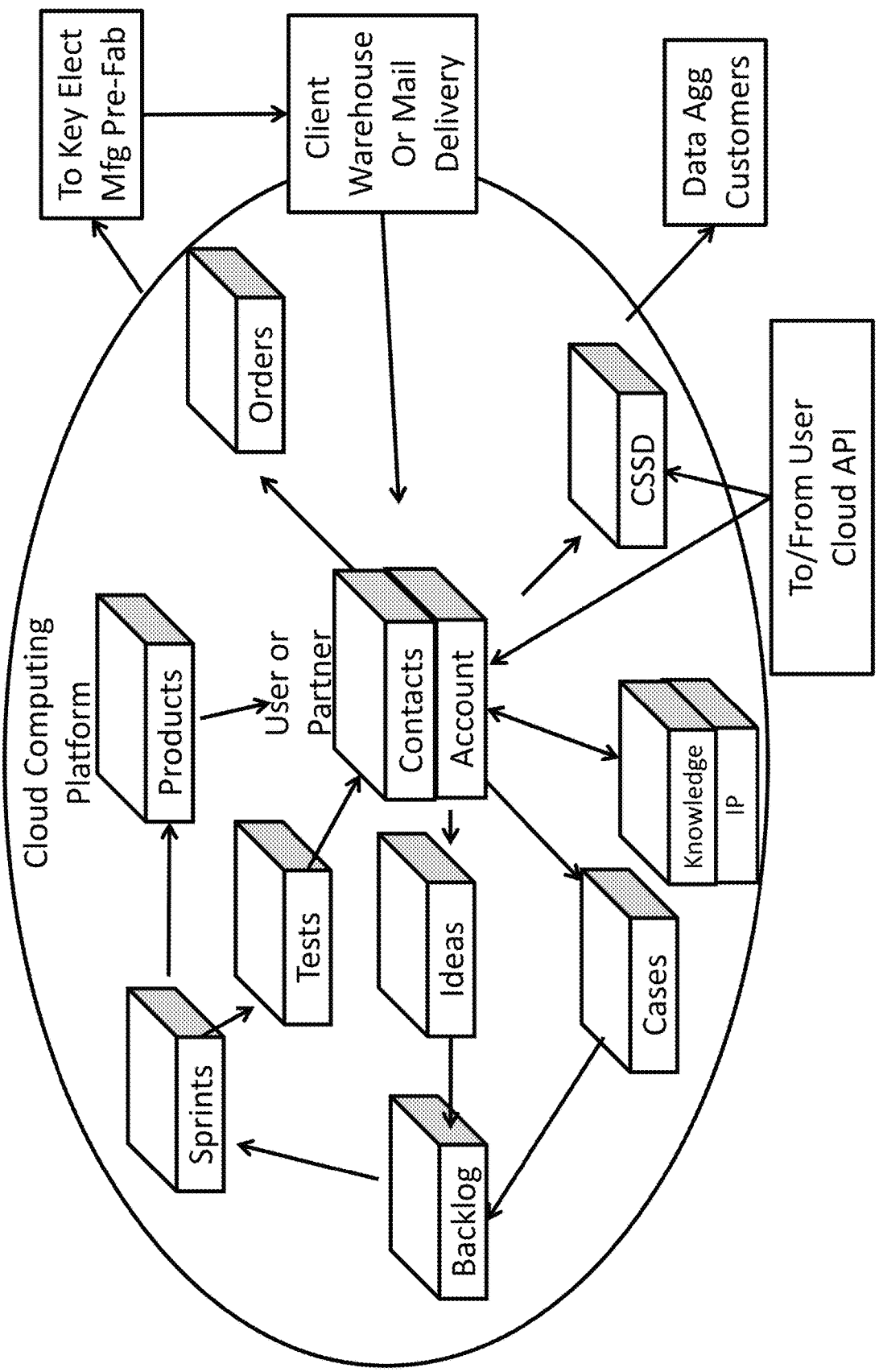
FIG. 30 shows a diagram of another embodiment of a cloud enterprise.

The system architecture is diagrammed in FIG. 20. Here, the remote transceiver device is characterized as a Mobile App, preferably on a smartphone, which is in communication with the sensor apparatus via wireless communication. Mobile App controls and commands are diagrammed in FIG. 21. The Mobile App may network with the user web service, as shown in FIG. 22, to access the cloud database and library, as shown in FIG. 23. An example cloud platform operable with the present invention is the EMITTI platform (ex: Amazon Web Services, Microsoft Azure, or any other similar commercial or private cloud platform); cloud architecture is more specifically detailed in FIG. 28. The web service allows the user to access, analyze, and manipulate user output data that was transmitted from the sensor apparatus. FIG. 24 shows an individual user web front including features such as external sensor correlation, selected session summary, and session tables. FIG. 25 shows the user web front for multiple users. The complete website builder platform is shown in FIG. 26. The website may connect to the cloud computing enterprise, which is diagrammed in FIGS. 29 and 30, or link to social media sites.

Figure 31:
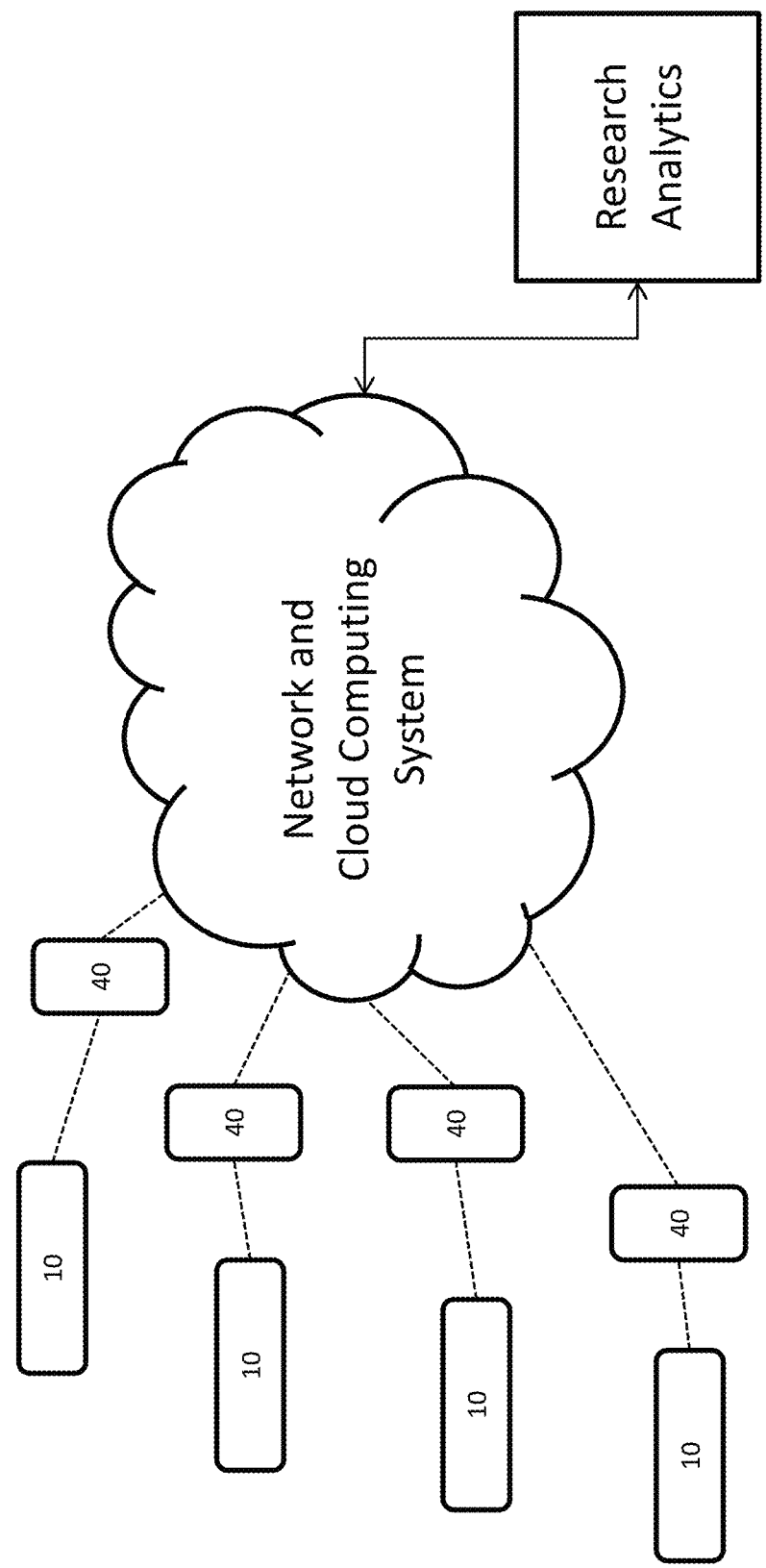
FIG. 31 shows a diagram of a system for epidemiological research.

From the cloud computing system, data from multiple users may be stored, as diagrammed in FIG. 31. Access to these data may be acquired by researchers and epidemiologists to perform a variety of research analytics. The captured data will preferably be from the same sweat detection model, providing greater reliability to the pool of data. The ability to collect these specific biomarker data from such a large population of subjects creates an invaluable real-time, continuous epidemiological research system and method.

The preferred embodiment of the system includes an apparatus that intimately adheres to mammalian skin, more specifically to human skin. The sweat from the skin is moved into the apparatus for detection of sweat biomarkers and analytes. Where on the mammal the apparatus is positioned is dependent upon, by way of example and not limitation, user preference, sweat collection patterns, or sweat production amounts at a given location.

The apparatus is operable to determine a measured amount of transepidermal sweat and/or a measured amount of evaporative sweat and an estimated amount of transepidermal sweat and/or an estimated amount of evaporative sweat. In one embodiment, estimated amounts are determined based on body surface area, mass, gender, fitness level, weight, and/or age. In another embodiment, the apparatus is operable to compare the estimated amount of transepidermal sweat and/or the estimated amount of evaporative sweat to the measured amount of transepidermal sweat and/or the measured amount of evaporative sweat and provide a status based on the comparison of the estimated amount of transepidermal sweat and/or the estimate amount of evaporative sweat to the measured amount of transepidermal sweat and/or the measured amount of evaporative sweat. In another embodiment, the apparatus uses a tangible/quantifiable fitness level in combination with sweat biomarker ratios in order to calculate real-time sweat rates. In another embodiment, the apparatus uses gender factors in order to improve sweat flow rate accuracy. In another embodiment, the apparatus uses consumption refresh models, exact custom formula to return to start condition.

The apparatus is also operable to model losses and consumption of sweat in order to estimate blood serum characteristics at a time before use, at the start of use, in real-time, or at a time after use. In one embodiment, the apparatus is operable to predict performance erosion and injury probability based on the analysis of at least one biological fluid biomarker. In another embodiment, the apparatus is operable to use the analysis of sweat to provide corrective action recommendations.

Figure 32:
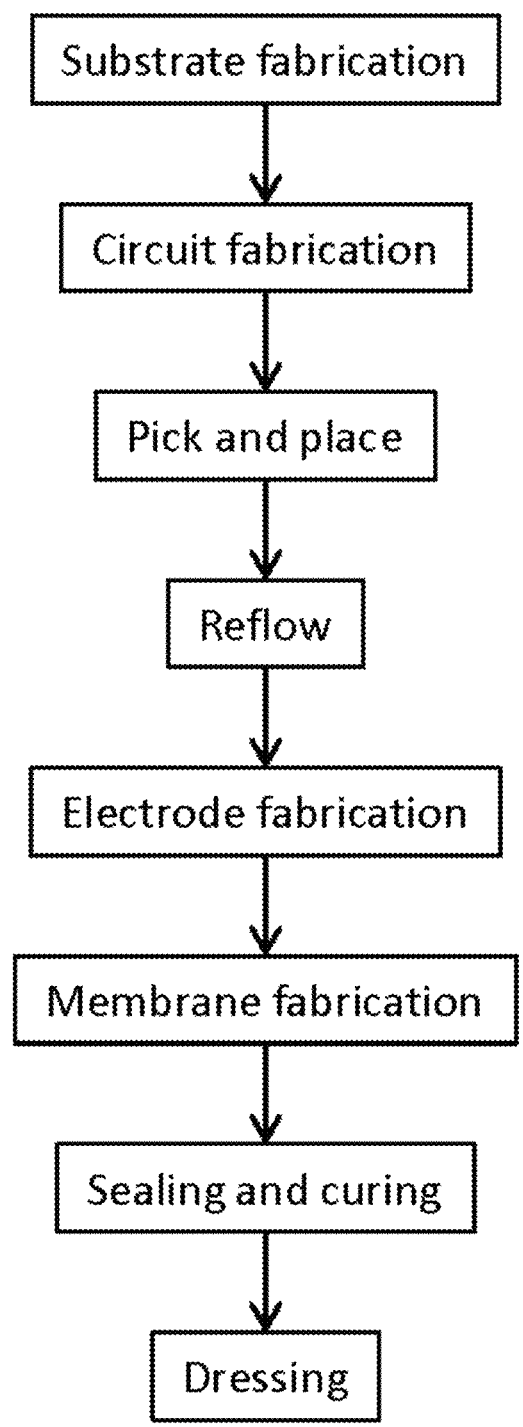
FIG. 32 shows a diagram of a manufacturing process for the sensor apparatus.

The basic fabrication process, as shown in FIG. 32, includes the following steps: substrate fabrication, circuit fabrication, pick and place, reflow soldering, electrode fabrication, circuit board programming, membrane fabrication, sealing and curing, and dressing.

Electrode fabrication includes the described novel metallization paste and sequence for the reference probe; novel metallization application and sequence for active probes; novel line and space characteristics for sweat flow rate and small protein probes.

Membrane fabrication entails the described novel precision ionophore application and cure processes.

Dressing entails the described novel laser cutting, bonding, and assembly steps for fabricating the microfluidic components and the dressing.

Figure 33:
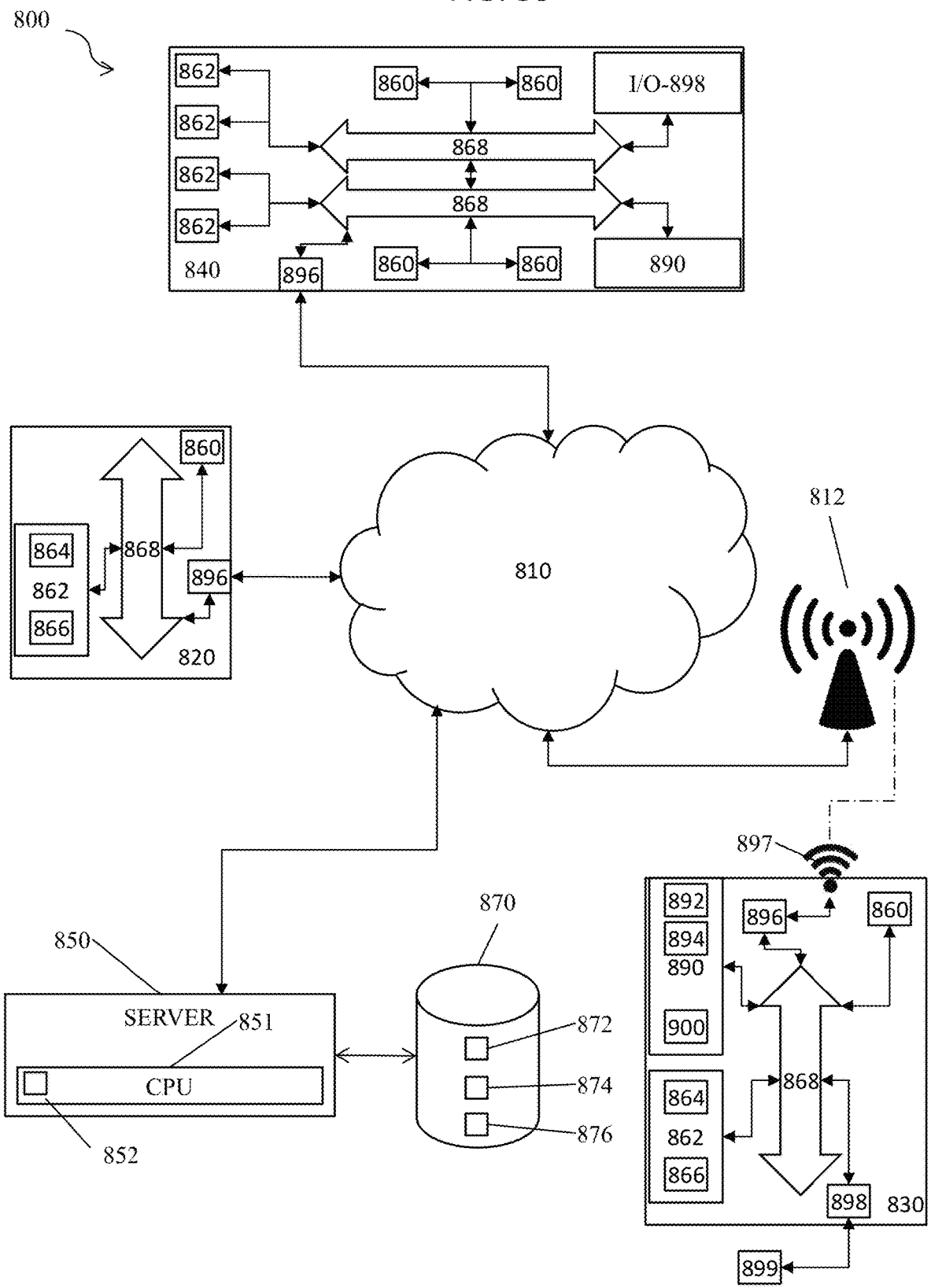
FIG. 33 shows a schematic diagram illustrating general components of a cloud-based computer system.

FIG. 33 is a schematic diagram of an embodiment of the invention illustrating a cloud-based computer system, generally described as 800, having a network 810, a plurality of computing devices 820, 830, 840, a server 850 and a database 870.

The server 850 is constructed, configured and coupled to enable communication over a network 810 with a computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by a plurality of mobile communication computing devices 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, a personal digital assistant (PDA), a smart phone, a desktop computer, a netbook computer, a tablet computer, a workstation, a laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers) or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 33, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to the bus 868. Computing devices may communicate communication media through wired networks, direct-wired connections or wirelessly such as acoustic, RF or infrared through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory or other solid state memory technology, disks or discs (e.g., digital versatile discs (DVD), HD-DVD, BLU-RAY, compact disc (CD), CD-ROM, floppy disk) or other optical storage, magnetic cassettes, magnetic tape, magnetic disk storage or other magnetic storage devices, or any other medium that can be used to store the computer readable instructions and which can be accessed by the computer system 800.

It is also contemplated that the computer system 800 may not include all of the components shown in FIG. 33, may include other components that are not explicitly shown in FIG. 33, or may utilize an architecture completely different than that shown in FIG. 33. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

By way of definition and description supporting the claimed subject matter, preferably, the present invention includes communication methodologies for transmitting data, data packets, messages or messaging via a communication layer. Wireless communications over a network are preferred. Correspondingly, and consistent with the communication methodologies for transmitting data or messaging according to the present invention, as used throughout this specification, figures and claims, wireless communication is provided by any reasonable protocol or approach, by way of example and not limitation, Bluetooth, Wi-Fi, cellular, ZigBee, near field communication, or other similar commercially utilized standards; the term "ZigBee" refers to any wireless communication protocol adopted by the Institute of Electronics & Electrical Engineers (IEEE) according to standard 802.15.4 or any successor standard(s), the term "Wi-Fi" refers to any communication protocol adopted by the IEEE under standard 802.11 or any successor standard(s), the term "WiMax" refers to any communication protocol adopted by the IEEE under standard 802.16 or any successor standard(s), and the term "Bluetooth" refers to any short-range communication protocol implementing IEEE standard 802.15.1 or any successor standard(s). Additionally or alternatively to WiMax, other communications protocols may be used, including but not limited to a "1G" wireless protocol such as analog wireless transmission, first generation standards based (IEEE, ITU or other recognized world communications standard), a "2G" standards based protocol such as "EDGE or CDMA 2000 also known as 1×RTT", a 3G based standard such as "High Speed Packet Access (HSPA) or Evolution for Data Only (EVDO), any accepted 4G standard such as "IEEE, ITU standards that include WiMax, Long Term Evolution "LTE" and its derivative standards, any Ethernet solution wireless or wired, or any proprietary wireless or power line carrier standards that communicate to a client device or any controllable device that sends and receives an IP based message. The term "High Speed Packet Data Access (HSPA)" refers to any communication protocol adopted by the International Telecommunication Union (ITU) or another mobile telecommunications standards body referring to the evolution of the Global System for Mobile Communications (GSM) standard beyond its third generation Universal Mobile Telecommunications System (UMTS) protocols. The term "Long Term Evolution (LTE)" refers to any communication protocol adopted by the ITU or another mobile telecommunications standards body referring to the evolution of GSM-based networks to voice, video and data standards anticipated to be replacement protocols for HSPA. The term "Code Division Multiple Access (CDMA) Evolution Date-Optimized (EVDO) Revision A (CDMA EVDO Rev. A)" refers to the communication protocol adopted by the ITU under standard number TIA-856 Rev. A.

It will be appreciated that embodiments of the invention described herein may be comprised of one or more conventional processors and unique stored program instructions that control the one or more processors to implement, in conjunction with certain non-processor circuits, some, most, or all of the functions for the systems and methods as described herein. The non-processor circuits may include, but are not limited to, radio receivers, radio transmitters, antennas, modems, signal drivers, clock circuits, power source circuits, relays, current sensors, and user input devices. As such, these functions may be interpreted as steps of a method to distribute information and control signals between devices. Alternatively, some or all functions could be implemented by a state machine that has no stored program instructions, or in one or more application specific integrated circuits (ASICs), in which each function or some combinations of functions are implemented as custom logic. Of course, a combination of the two approaches could be used. Thus, methods and means for these functions have been described herein. Further, it is expected that one of ordinary skill in the art, notwithstanding possibly significant effort and many design choices motivated by, for example, available time, current technology, and economic considerations, when guided by the concepts and principles disclosed herein, will be readily capable of generating such software instructions, programs and integrated circuits (ICs), and appropriately arranging and functionally integrating such non-processor circuits, without undue experimentation.

Certain modifications and improvements will occur to those skilled in the art upon a reading of the foregoing description, by way of example, a device having at least one microprocessor for storing data may be operable in the device before data transmission. Another example includes other advanced sensors, as well as being incorporated into smart fabrics and protective wear. Advanced sensors include advanced sweat biomarkers, pulse rate, breath rate, micro EKG, micro O2, picture log, voice log, voice translate, tissue safe X-ray, blood pressure, and combinations thereof. Smart fabrics incorporate the present invention and include active heat/cooling, kinetic energy generation, electromagnetic energy harvesting, wearable energy storage, wearable data storage, wearable processing, wearable communications, elastomeric actuators, and combinations thereof. More generally, the apparatus may be part of apparel and material for lower body clothing and upper body clothing. The present invention is also incorporated into enhanced protective wear such as enhanced helmets, gloves and footwear. Specifically, sensors, conductors and/or ionophores are utilized on moisture management fabrics, such as by way of example and not limitation, Under Armour fabrics. Microfluidic moisture transport is also utilized in fabric and other material which directly contacts human skin when worn. Enhanced helmets include those with MRI, 3D audio, visual enhancement, mixed reality, breath sensors, aerosol nutrition and combinations thereof. Enhanced gloves include touch communications, elastomeric grip, gesture control and combinations thereof. Enhanced footwear includes power generation boots, 3D tracking, tactile alerts, communication transceivers, and combinations thereof.

The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

What is claimed is:

1. A method of fabrication for a biological fluid sensor for analyzing at least one analyte in human biological fluid, said biological fluid sensor comprising electronic components, electrochemical components, and chemical components, the method comprising:
    fabricating at least one substrate;
    fabricating at least one circuit on the at least one substrate;
    picking and placing the electronic components onto the at least one circuit, wherein the electronic components include at least one microcontroller and at least one transceiver;
    reflow soldering of the at least one circuit;
    fabricating at least two electrodes, wherein the at least two electrodes are comprised of at least one active electrode and at least one reference electrode;
    applying an ionophore coating on the at least one active electrode;
    sealing the at least one active electrode to create an electronic layer; and
    integrating the electronic layer with a top cover layer, a microfluidic management layer, and a double-sided adhesive layer;
wherein the step of fabricating the at least two electrodes further comprises:
    fabricating a metallization paste;
    constructing the least one reference electrode by applying the metallization paste on top of at least one first trace metal of the at least one circuit and annealing; and
    constructing the least one active electrode by applying the metallization paste on top of at least one second trace metal of the at least one circuit and annealing; and
wherein the step of integrating the electronic layer with the top cover layer, the microfluidic management layer, and the double-sided adhesive layer further comprises:
    cutting the top cover layer, wherein the top cover layer has an adhesive side;
    placing the electronic layer on top of the adhesive side of the top cover layer, wherein the at least two electrodes are facing up;
    cutting the microfluidic management layer;
    surrounding the at least two electrodes with the microfluidic management layer;
    cutting a sheet of double-sided adhesive to create the double-sided adhesive layer;
    placing the double-sided adhesive layer on top of the electronic layer such that the double-sided adhesive layer covers the electronic layer; and
    pressing the top cover layer, the microfluidic management layer, the electronic layer, and the double-sided adhesive layer for permanent bond;
wherein the at least one substrate includes an active electrode substrate and a reference electrode substrate,
wherein the active electrode substrate includes the at least one active electrode and the reference electrode substrate includes the at least one reference electrode, and
wherein the step of applying the ionophore coating on the at least one active electrode is performed using a multilayer substrate approach comprising:
    casting an ionophore in a well of the reference electrode substrate;
    placing an adhesive layer or a bonding film layer on top of the active electrode substrate; and
    attaching the reference electrode substrate to the active electrode substrate using the adhesive layer or the bonding film layer.

2. The method of claim 1, wherein the biological fluid is sweat.

3. The method of claim 1, wherein the metallization paste is made of at least one stable metal selected from the group consisting of silver, gold, platinum, and palladium.

4. The method of claim 1, wherein the at least one reference electrode and the at least one active electrode include silver, zinc, copper, gold, platinum, rhodium, carbon, and a combination thereof.

5. The method of claim 1, wherein applying the ionophore coating on the at least one active electrode is performed via an automated dispenser.

6. The method of claim 1, further including curing the ionophore coating using heat and light.

7. The method of claim 1, wherein a conductive trace is in a ring around the well, wherein the conductive trace does not contact the well, wherein the at least one active electrode is within the well.

8. The method of claim 1, wherein the ionophore coating is fabricated by dissolving an ion selective material in a polyvinylchloride (PVC) solution.

9. The method of claim 1, wherein the ionophore coating is cast in a shape and placed on a carrier or a film to facilitate application on the at least one active electrode.

10. The method of claim 9, wherein the carrier or the film becomes an integral part of the biological fluid sensor.

11. The method of claim 1, wherein the ionophore coating has an embedded glass or plastic fiber.

12. The method of claim 1, wherein the microfluidic layer is comprised of one or more of wicking paper, fabric, and crystal fibers.

13. The method of claim 1, wherein the at least one analyte is one or more of sodium, potassium, chloride, oxygen, glucose, calcium, ammonium, copper, magnesium, iron, zinc, lactate, creatinine, uric acid, urea, ethanol, amino acids, hormones, steroids, proteins, catecholamines, and interleukins.

14. The method of claim 1, wherein the double-sided adhesive layer further contains laser cut macrofluidic pores.

15. The method of claim 1, wherein the step of integrating the electronic layer with the top cover layer, the microfluidic management layer, and the double-sided adhesive layer further includes:
   mechanically separating an individual unit; and
   automatically packaging the individual unit into an individualized wrapper to create an individually wrapped unit.

16. A method of fabrication for a biological fluid sensor for analyzing at least one analyte in human biological fluid, said biological fluid sensor comprising electronic components, electrochemical components, and chemical components, the method comprising:
   fabricating at least one substrate;
   fabricating at least one circuit on the at least one substrate;
   picking and placing the electronic components onto the at least one circuit, wherein the electronic components include at least one microcontroller and at least one transceiver;
   reflow soldering of the at least one circuit;
   fabricating at least two electrodes, wherein the at least two electrodes are comprised of at least one active electrode and at least one reference electrode;
   applying an ionophore coating on the at least one active electrode;
   sealing the at least one active electrode to create an electronic layer; and
   integrating the electronic layer with a top cover layer, a microfluidic management layer, and a double-sided adhesive layer;
wherein the step of fabricating the at least two electrodes further comprises:
   fabricating a metallization paste;
   constructing the least one reference electrode by applying the metallization paste on top of at least one first trace metal of the at least one circuit and annealing; and
   constructing the least one active electrode by applying the metallization paste on top of at least one second trace metal of the at least one circuit and annealing; and
wherein the step of integrating the electronic layer with the top cover layer, the microfluidic management layer, and the double-sided adhesive layer further comprises:
   cutting the top cover layer, wherein the top cover layer has an adhesive side;
   placing the electronic layer on top of the adhesive side of the top cover layer, wherein the at least two electrodes are facing up;
   cutting the microfluidic management layer;
   surrounding the at least two electrodes with the microfluidic management layer;
   cutting a sheet of double-sided adhesive to create the double-sided adhesive layer;
   placing the double-sided adhesive layer on top of the electronic layer such that the double-sided adhesive layer covers the electronic layer; and
   pressing the top cover layer, the microfluidic management layer, the electronic layer, and the double-sided adhesive layer for permanent bond;
wherein a conductive trace is in a first ring around the at least one active electrode, wherein the conductive trace in the first ring around the at least one active electrode does not contact the at least one active electrode, and wherein the step of applying the ionophore coating on the at least one active electrode is performed using a surface tension dam approach comprising:
   printing, depositing, or adhering a soldermask, a printed ink, or a non-conductive material on the at least one substrate in a second ring around the at least one active electrode, wherein the second ring around the at least one active electrode is inside the first ring around the at least one active electrode, and wherein the first ring around the at least one active electrode does not contact the second ring around the at least one active electrode; and
   applying the ionophore coating on the at least one active electrode via liquid deposition such that the ionophore coating completely covers the at least one active electrode and is contained within the second ring formed by the soldermask, the printed ink, or the non-conductive material; and
   wherein the non-conductive material is a different material than the at least one substrate.

17. The method of claim 16, wherein the biological fluid is sweat.

18. The method of claim 16, wherein the double-sided adhesive layer further contains laser cut macrofluidic pores.

19. The method of claim 16, wherein the ionophore coating is fabricated by dissolving an ion selective material in a polyvinylchloride (PVC) solution.

* * * * *